United States Patent [19]
Ali-Osman et al.

[11] Patent Number: 5,968,737
[45] Date of Patent: Oct. 19, 1999

[54] METHOD OF IDENTIFYING INHIBITORS OF GLUTATHIONE S-TRANSFERASE (GST) GENE EXPRESSION

[75] Inventors: Francis Ali-Osman, Missouri City; Gabriel Lopez-Berestein, Bellaire, both of Tex.; John K. Buolamwini, Oxford, Miss.; Gamil Antoun, Houston, Tex.; Hui-Wen Lo, Sugarland, Tex.; Charles Keller; Olanike Akande, both of Houston, Tex.

[73] Assignees: The University of Mississippi, University, Miss.; The Board of Regents, The University of Texas System, Austin, Tex.

[21] Appl. No.: 08/747,536

[22] Filed: Nov. 12, 1996

[51] Int. Cl.$^6$ .............................. C12Q 1/48; C12Q 1/68; C07H 21/02; C07H 21/04
[52] U.S. Cl. .......................... 435/6; 435/15; 435/91.31; 435/193; 435/375; 536/24.5
[58] Field of Search .................................. 435/6, 7.1, 7.2, 435/7.21, 15, 91.1, 91.31, 193, 325, 375; 514/23, 44, 183, 359, 364, 374, 378; 536/24.5; 935/33, 34, 36

[56] References Cited

PUBLICATIONS

Aoyama et al. Benstatins C and D, new inhibitors of glutathione S–transferase, produced by Streptomyces sp. MI384–DF12, J. Antibiot. 46(5): 712–718, May 1993.

Aoyama et al. Bequiosnstatins A and B, new inhibitors of glutathione S–transferase, produced by Streptomyces sp. MI384–DF12. J. Antibiot. 46(6): 914–920, Jun. 1993.

Christoffersen et al. Ribozymes as human therapeutic agents. J. Med. Chem. 38(12): 2023–2037, Jun. 1995.

Ban et al, Transfection of glutathione S–transferase (GST)–pi antisense complementary DNA increases the sensitivity of a colon cancer cell line to adriamycin, cisplatin, melphalan, and etoposide. Cancer Res. 56: 3577–3582, Aug. 1996.

Ahmad et al., "Primary and Secondary Structural Analyses of Glutathione S–Transferase π from Human Placenta", *Archives of Biochemistry and Biophysics*, vol. 278:2,.398–408, 1990.

Ali–Osman et al., "Molecular Cloning, Characterization and Expression of Novel Functionally Different Human Gluthathione S–Transferase–P1 Gene Variant", ISSX Proceedings, vol. 7, 1995.

Ali–Osman et al., "Glutathione Content and Glutathione–S–transferase Expression in 1,3–Bis(2–chloroethyl)–l–nitrosourea–resistant Human Malignant Astrocytoma Cell Lines", *Cancer Research* 50, 6979–6980, 1990.

Asono and Ali–Osman, "Pattern of Expression of Glutathione S–transferase Subclasses in Human Malignant Astrocytoma Cells Determined by Immunocytochemistry and In Situ Hybridization", Proceedings of the American Association For Cancer Research, vol. 34, 341, 1993.

Blaber et al., "Structural Basis of Amino Acid α Helix Propensity", *Science*, vol. 260, 1637–1640, 1993.

Board et al., Isolation of a cDNA Clone and Localization of the Human Glutathione S–Transferase 3 Genes to Chromosome Bands 11q13 and 12q13–14, *Ann. Hum. Genet.*, 53, 205–213, 1989.

Boylan and Gudas, Overexpression of the Cellular Retinoic Acid Binding Protein–I (CRABP–I) Results in a Reduction in Differentiation–Specific Gene Expression in F9 Teratocarcinoma Cells, *Journal of Cell Biology*, vol. 112:5, 965–979, 1991.

Boyland and Chasseaud, "The Role of Glutathione and Glutathione S–Transferases in Mercapturic Acid Biosynthesis", In: Advances in Enzymology, Ed. F.F. Nord, vol. 32, 173–219, 1969.

Burger et al., "Glioblastoma Multiforme and Anaplastic Astrocytoma", *Cancer* 56:1106–111, 1985.

Chen et al., "The Second Intron of the K–ras Gene Contains Regulatory Elements Associated with Mouse Lung Tumor Susceptibility", *Proc. Nat'l. Acad. Sci. USA* vol. 91, 1589–1593, 1994.

Chomczynski and Sacchi, "Single–Step Method of RNA Isolation by Acid Guanidinium Thiocyanate–Phenol–Chloroform Extraction", *Analytical Biochemistry* 162, 156–159, 1987.

Chrysogelos, "Chromatin Structure of the EGFR Gene Suggests a Role For Intron 1 Sequences in its Regulation in Breast Cancer Cells", *Nucleic Acids Research* vol. 21:24, 5736–5741, 1993.

Coles and Ketterer, "The Role of Glutathione and Glutathione Transferases in Chemical Carcinogenesis", *Biochemistry and Molecular Biology,*, vol. 25:1, 47–70, 1990.

Cowell et al., "The Structure of the Human Glutathione S–transferase π Gene", *Biochem. J.* 255, 79–83, 1988.

Duester et al., "Retinoic Acid Response Element in the Human Alcohol Dehydrogenase Gene ADH3: Implications for Regulation of Retinoic Acid Synthesis", *Molecular and Cellular Biology*, vol. 11:3, 1638–1646, 1991.

Durand et al., "All–Trans and 9–Cis Retinoic Acid Induction of CRABPII Transcription is Mediated by RAR–RXR Heterodimers Bound to DR1 and DR2 Repeated Motifs", *Cell*, vol. 71, 73–85, 1992.

(List continued on next page.)

*Primary Examiner*—George C. Elliott
*Assistant Examiner*—Thomas G. Larson
*Attorney, Agent, or Firm*—Arnold, White & Durkee

[57] ABSTRACT

Complementary DNA and genomic clones for three variants of GST-π are disclosed. It is demonstrated that certain of these variants are overexpressed in gliomas, thereby indicating an involvement with that form of cancer. This permits the detection and treatment of certain classes of tumors using new compositions such as GST-π genes, oligonucleotides, peptides and antibodies.

11 Claims, 26 Drawing Sheets

(3 of 26 Drawing Sheet(s) Filed in Color)

OTHER PUBLICATIONS

Fanjul et al., "A New Class of Retinoids with Selective Inhibition of AP–1 Inhibits Proliferation", *Nature* vol. 372, 107–110, 1994.

Favreau and Pickett, "Transcriptional Regulation of the Rat NAD(P)H:Quinone Reductase Gene", *The Journal of Biological Chemistry* vol. 266:7, 4556–4561, 1991.

Glass et al., "Regulation of Gene Expression by Retinoic Acid Receptors", *DNA and Cell Biology* vol. 10:9, 623–638, 1991.

Gubler and Hoffman, "A Simple and Very Efficient Method for Generating cDNA Libraries", *Gene* 25, 263–269, 1983.

Habig et al., "Glutathione S–Transferases", *The Journal of Biological Chemistry*, vol. 249:22, 7130–7139, 1974.

Hayes and Pulford, "The Glutathione S–Transferase Supergene Family: Regulation of GST* and the Contribution of the Isoenzymes to Cancer Chemoprotection and Drug Resistance", *Critical Reviews in Biochemistry and Molecular Biology*, 30(6):445–600, 1995.

Hess et al., "Cooperation of Glycoloytic Enzymes", In: Advances in Enzyme Regulation, vol. 7, 149–167, Ed. George Weber, 1968.

Hitzeman et al., "Isolation and Characterization of the Yeast 3–Phosphoglycerokinase Gene (PGK) by an Immunological Screening Technique", *The Journal of Biological Chemistry*, vol. 255:24, 12073–12080, 1980.

Jung et al., "Identification of Multiple Repeat Sequences and Transcription–Related Elements Within Introns 4, 8 and 9 of Human RAF–1", *Biochemical and Biophysical Research Communications*, vol. 190:2, 462–469, 1993.

Kano et al., "Structure and Expression of a Human Class π Glutathione S–Transferase Messenger RNA", *Cancer Research*, 47, 5626–5630, 1987.

Kutluk and Ali–Osman, "Glutathione S–transferase and P–glycoprotein Gene Expression: Association with the Drug Resistance Phenotype in a Human Medulloblastoma Cell Line", Proceedings of the American Association for Cancer Research, vol. 34, 341, 1993.

Izawa and Ali–Osman, "Structure of the Glutathione S–Transferase–π Gene Cloned From a Human Malignant Glioma Cell Line", Proceedings of the American Association for Cancer Research, vol. 34, 341, 1993.

Lammie and Peters, "Chromosome 11q13 Abnormalities in Human Cancer", *Cancer Cells*, vol. 3:11, 413–420, 1991.

Lehmann et a l., "RARγ2 Expression is Regulated Through a Retinoic Acid Response Element Embedded in Sp1 Sites", *Molecular and Cellular Biology*, vol. 12:7, 2976–2985, 1992.

Leroy et al., "Mouse Retinoic Acid Receptor α2 Isoform is Transcribed from a Promoter that Contains a Retinoic Acid Response Element", *Proc. Nat'l. Acad. Sci. USA*, vol. 88, 10138–10142, 1991.

Li and Jaiswal, "Regulation of Human NAD(P)H:Quinone Oxidoreductase Gene", *The Journal of Biological Chemistry*, vol. 267:21, 15907–15104, 1992.

Lozano and Levine, "Tissue–Specific Expression of p53 in Transgenic Mice is Regulated by Intron Sequences", *Molecular Carcinogenesis* 4:3–9, 1991.

Mangelsdorf et al., "A Direct Repeat in the Cellular Retinol–Binding Protein Type II Gene Confers Differential Regulation by RXR and RAR", *Cell*, vol. 66, 555–561, 1991.

Mannervik et al., "Nomenclature for Human Glutathione Transferases", *Biochem. J.*, 282, 305–308, 1992.

Mannervik and Danielson, "Glutathione Transferases—Structure and Catalytic Activity", *CRC Critical Reviews in Biochemistry*, vol. 23:3, 283–337, 1988.

Mannervik, "The Isoenzymes of Glutathione Transferase", In: Advances in Enzymology, vol. 57, 357–417, Ed. Alton Meister, 1985.

Maugard–Louboutin et al., Glutathione S–transferase π Expression in Human Astrocytomas Determined by RT–PCR, Proceedings of the American Association for Cancer Research, vol. 36, 213, 1995.

Morrow and Cowan, "Glutathione S–Transferases and Drug Resistance", *Cancer Cells*, vol. 2:1, 15–22, 1990.

Morrow et al., "Structure of the Human Genomic Glutathione S–transferase–π Gene", *Gene* 75, 3–11, 1989.

Moscow et al., "Isolation of the Human Anionic Glutathione S–transferase cDNA and the Relation of its Gene Expression to Estrogen–Receptor Content in Primary Breast Cancer", *Proc. Nat'l. Acad. Sci. USA*, vol. 85, 6518–6522, 1988.

Mosmann, "Rapid Colorimetric Assay for Cellular Growth and Survival: Application to Proliferation and Cytotoxicity Assays", *Journal of Immunological Methods* 65, 55–63, 1983.

Nasrin et al., "An Insulin Response Element in the Glyceraldehyde–3–phosphate Dehydrogenase Gene Binds a Nuclear Protein Induced by Insulin in Cultured Cells and by Nutritional Manipulations In Vivo", *Proc. Nat'l. Acad. Sci. USA* vol. 87, 5273–5277, 1990.

Okuda et al., "The Structure of the Rat Glutathione S–Transferase P Gene and Related Pseudogenes", *The Journal of Biological Chemistry*, vol. 262:8, 3858–3863, 1987.

Pickett and Lu, "Glutathione S–Transferases: Gene Structure, Regulation, and Biological Function", *Annu. Rev. Biochem.* 58:743–64, 1989.

Reinemer et al., "Three–dimensional Structure of Class π Glutathione S–Transferase from Human Placenta in Complex with S–Hexylglutathione at 2–8 A Resolution", *J. Mol. Biol.* 227, 214–226, 1992.

Saint–Ruf et al, "GST π Gene is Frequently Coamplified with INT2 and HSTF1 Proto–Oncogenes in Human Breast Cancers" *Oncogene*, 6, 403–406, 1991.

Sato "Glutathione Transferases as Markers of Preneoplasia and Neoplasia", *Advances in Cancer Research*, vol. 52, 205–255, 1989.

Schule et al., "Retinoic Acid is a Negative Regulator of AP–1 Responsive Genes" *Proc. Nat'l. Acad. Sci. USA* vol. 88, 6092–6096, 1991.

"Glutathione Conjugation" Academic Press Limited, Edited by Helmut Sies and Brian Ketterer, Academic Press Limited, 1988.

Stumpo et al., "Identification of c–fos Sequences Involved in Induction by Insulin and Phorbol Esters" *The Journal of Biological Chemistry*, vol. 263:4, 1611–1614, 1988.

Taub et al., "Insulin as a Growth Factor in Rat Hepatoma Cells", *The Journal of Biological Chemistry* vol. 262:22, 10893–10897, 1987.

Tew, "Glutathione–associated Enzymes in Anticancer Drug Resistance", *Cancer Research* 54, 4313–4320, 1994.

Tidefelt et al., "Expression of Glutathione Transferase π as a Predictor for Treatment Results at Different Stages of Acute Nonlymphoblastic Leukemia", *Cancer Research*, 52, 3281–3285, 1992.

Tsuchida and Sato, "Glutathione Transferases and Cancer", *Critical Reviews in Biochemistry and Molecular Biology*, 27(4,5):337–384, 1992.

Vasios et al., "A Retinoic Acid–Responsive Element is Present in the 5' Flanking Region of the Laminin B1 Gene", *Proc. Nat'l. Acad. Sci. USA*, vol. 86, 9099–9103, 1989.

Waxman, "Glutathione S–Transferases: Role in Alkylating Agent Resistance and Possible Target for Modulation Chemotherapy—A Review", *Cancer Research*, 50, 6449–6454, 1990.

Xia et al., "Glutathione Transferase π Its Minimal Promoter and Downstream Cis–Acting Element", *Biochemical and Biophysical Research Communications*, vol. 176:1, 233–240, 1991.

Xia et al., "The Human Glutatione S–Transferase P1–1 Gene: Modulation of Expression by Retinoic Acid and Insulin", *Biochem. J.*, 292, 845–850, 1993.

Xia et al., "The Organization of the Human GSTP1–1 Gene Promoter and Its Response to Retinoic Acid and Cellular Redox Status", *Biochem. J.*, 313, 155–161, 1996.

Zimniak et al., "Naturally Occurring Human Glutathione S–Transferase GSTP1–1 Isoforms with Isoleucine and Valine in Position 104 Differ in Enzymic Properties", *Eur. J. Biochem.*, 224, 893–899, 1994.

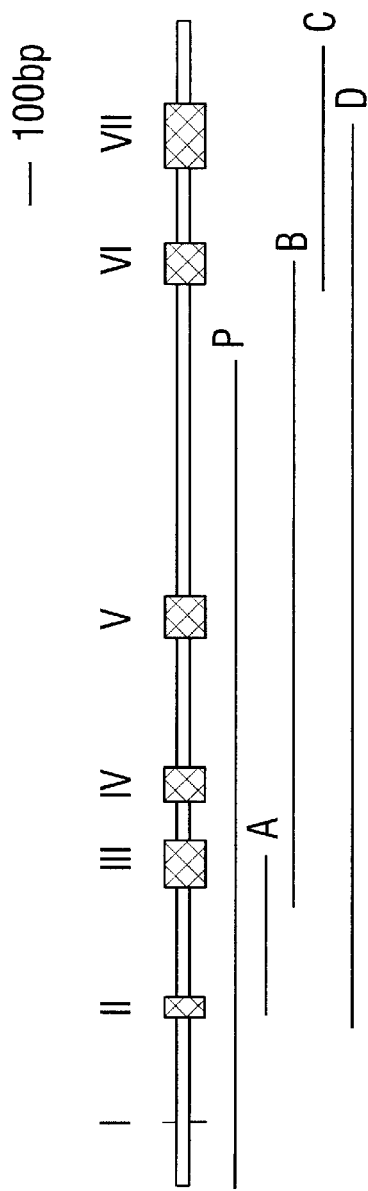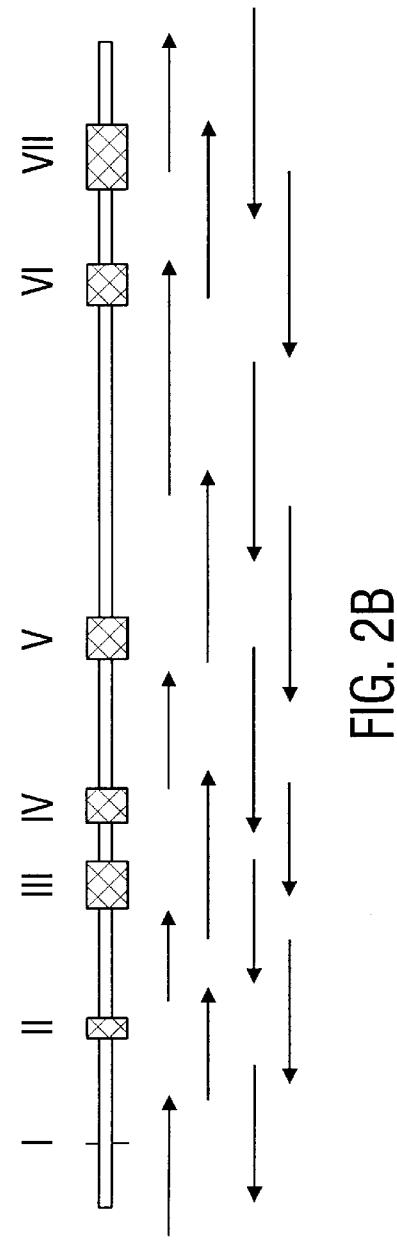

```
   1
   TTCGCCACCATG CCG CCC TAC ACC GTG GTC TAT TTC CCA GTT CGA GGC CGC    GSTP1*A
   GTCTTCGCCACC  -   -   -   -   -   -   -   -   -   -   -   -   -    GSTP1*B
   AGTCTTCGCCACC -   -   -   -   -   -   -   -   -   -   -   -   -    GSTP1*C
                 Met Pro Pro Tyr Thr Val Val Tyr Phe Pro Val Arg Gly Arg

TGC GCG GCC CTG CGC ATG CTG CTG GCA                                 GSTP1*A
    -   -   -   -   -   -   -   -   -                                  GSTP1*B
    -   -   -   -   -   -   -   -   -                                  GSTP1*C
   Cys Ala Ala Leu Arg Met Leu Leu Ala

70
   GAT CAG GGC CAG AGC TGG AAG GAG GAG GTG GTG ACC GTG GAG ACG TGG CAG  GSTP1*A
    -   -   -   -   -   -   -   -   -   -   -   -   -   -   -   -   -  GSTP1*B
    -   -   -   -   -   -   -   -   -   -   -   -   -   -   -   -   -  GSTP1*C
   Asp Gln Gly Gln Ser Trp Lys Glu Glu Val Val Thr Val Glu Thr Trp Gln

GAG GGC TCA CTC AAA GCC TCC TGC                                     GSTP1*A
    -   -   -   -   -   -   -   -                                      GSTP1*B
    -   -   -   -   -   -   -   -                                      GSTP1*C
   Glu Gly Ser Leu Lys Ala Ser Cys
```

FIG. 6B

```
145
CTA TAC GGG CAG CTC CCC AAG TTC CAG GAC GGA GAC CTC ACC CTG TAC CAG    GSTP1*A
 -   -   -   -   -   -   -   -   -   -   -   -   -   -   -   -   -    GSTP1*B
 -   -   -   -   -   -   -   -   -   -   -   -   -   -   -   -   -    GSTP1*C
Leu Tyr Gly Gln Leu Pro Lys Phe Gln Asp Gly Asp Leu Thr Leu Tyr Gln

TCC AAT ACC ATC CTG CGT CAC CTG                                        GSTP1*A
 -   -   -   -   -   -   -   -                                         GSTP1*B
 -   -   -   -   -   -   -   -                                         GSTP1*C
Ser Asn Thr Ile Leu Arg His Leu

220
GGC CGC ACC CTT GGG CTC TAT GGG AAG GAC CAG CAG GAG GCA GCC CTG GTG    GSTP1*A
 -   -   -   -   -   -   -   -   -   -   -   -   -   -   -   -   -    GSTP1*B
 -   -   -   -   -   -   -   -   -   -   -   -   -   -   -   -   -    GSTP1*C
Gly Arg Thr Leu Gly Leu Tyr Gly Lys Asp Gln Gln Glu Ala Ala Leu Val

GAC ATG GTG AAT GAC GGC GTG GAG                                        GSTP1*A
 -   -   -   -   -   -   -   -                                         GSTP1*B
 -   -   -   -   -   -   -   -                                         GSTP1*C
Asp Met Val Asn Asp Gly Val Glu
```

FIG. 6C

```
295
GAC CTC CGC TGC AAA TAC ATC TCC CTC ATC TAC ACC AAC TAT GAG GCG GGC    GSTP1*A
--- --- --- --- --- --- Ile --- --- --- --- --- --- --- --- Ala ---    GSTP1*B
--- --- --- --- --- --- GTC --- --- --- --- --- --- --- --- GCG ---    GSTP1*C
--- --- --- --- --- --- Val --- --- --- --- --- --- --- --- Ala ---    GSTP1*A
--- --- --- --- --- --- GTC --- --- --- --- --- --- --- --- GTG ---    GSTP1*B
Asp Leu Arg Cys Lys Tyr Val Ser Leu Ile Tyr Thr Asn Tyr Glu Val Gly    GSTP1*C

AAG GAT TAT GTG AAG GCA CTG
--- --- --- --- --- --- ---
--- --- --- --- --- --- ---
--- --- --- --- --- --- ---
Lys Asp Tyr Val Lys Ala Leu
```

FIG. 6D

```
370
CCC GGG CAA CTG AAG CCT TTT GAG ACC CTG AAG CCT TTT GAG ACC CTG TCC CAG AAC CAG GGA GGC    GSTP1*A
---     ---     ---     ---     ---     ---     ---     ---     ---     ---     ---     ---     ---    GSTP1*B
---     ---     ---     ---     ---     ---     ---     ---     ---     ---     ---     ---     ---    GSTP1*C
Pro Gly Gln Leu Lys Pro Phe Glu Thr Leu Ser Gln Asn Gln Gly Gly

AAG ACC TTC ATT GTG GGA GAC CAG    GSTP1*A
---     ---     ---     ---     ---     ---     ---     ---    GSTP1*B
---     ---     ---     ---     ---     ---     ---     ---    GSTP1*C
Lys Thr Phe Ile Val Gly Asp Gln

445
ATC TCC TTC GCT GAC TAC AAC CTG CTG GAC TTG CTG CTG ATC CAT GAG GTC    GSTP1*A
---     ---     ---     ---     ---     ---     ---     ---     ---     ---     ---     ---     ---     ---     ---     ---    GSTP1*B
---     ---     ---     ---     ---     ---     ---     ---     ---     ---     ---     ---     ---     ---     ---     ---    GSTP1*C
Ile Ser Phe Ala Asp Tyr Asn Leu Leu Asp Leu Leu Ile His Glu Val

CTA GCC CCT GGC TGC CTG GAT GCG    GSTP1*A
---     ---     ---     ---     ---     ---     ---     ---    GSTP1*B
---     ---     ---     ---     ---     ---     ---     ---    GSTP1*C
Leu Ala Pro Gly Cys Leu Asp Ala
```

FIG. 6E

```
520
TTC CCC CTG CTC TCA GCA TAT GTG GGG CGC CTC AGC GCC CGG CCC AAG CTC    GSTP1*A
 -   -   -   -   -   -   -   -   -   -   -   -  AGT  -   -   -   -    GSTP1*B
 -   -   -   -   -   -   -   -   -   -   -   -  AGC  -   -   -   -    GSTP1*C
Phe Pro Leu Leu Ser Ala Tyr Val Gly Arg Leu Ser Ala Arg Pro Lys Leu

AAG GCC TTC CTG GCC TCC CCT GAG                                        GSTP1*A
 -   -   -   -   -   -   -   -                                         GSTP1*B
 -   -   -   -   -   -   -   -                                         GSTP1*C
Lys Ala Phe Leu Ala Ser Pro Glu

595
TAC GTG AAC CTC CCC ATC AAT GGC AAC GGG AAA CAG TGAGGGTTGGGGGGACTCTG    GSTP1*A
 -   -   -   -   -   -   -   -   -   -   -   -  ------------------    GSTP1*B
 -   -   -   -   -   -   -   -   -   -   -   -  ------------------    GSTP1*C
Tyr Val Asn Leu Pro Ile Asn Gly Asn Gly Lys Gln STOP

AGCGGGAGGCAGAGTTTGCCTTC                                                GSTP1*A
-----------------------                                                GSTP1*B
-----------------------                                                GSTP1*C
```

FIG. 6F

```
625
CTTTCTCCAGGACCAATAAAAATTTCTAAGA                    GSTP1*A
--------------------------------GAGC               GSTP1*B
--------------------------------GAGCTAC            GSTP1*C
```

FIG. 6G

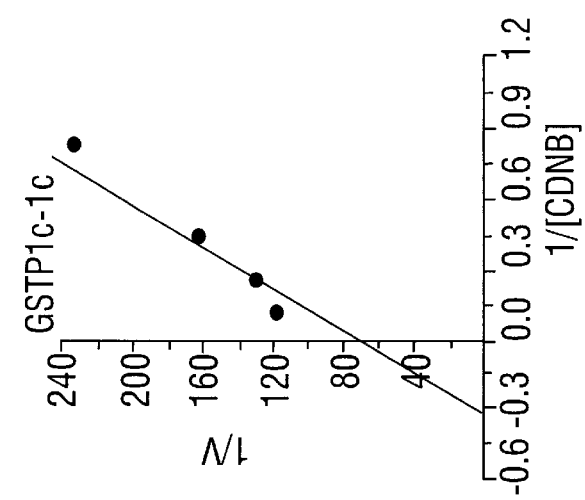
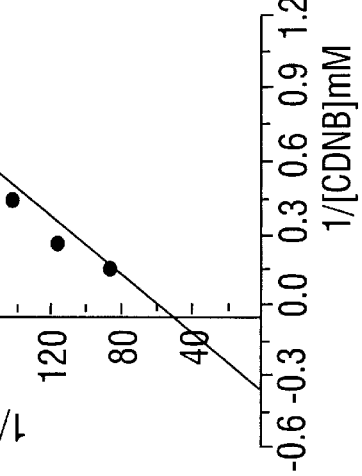
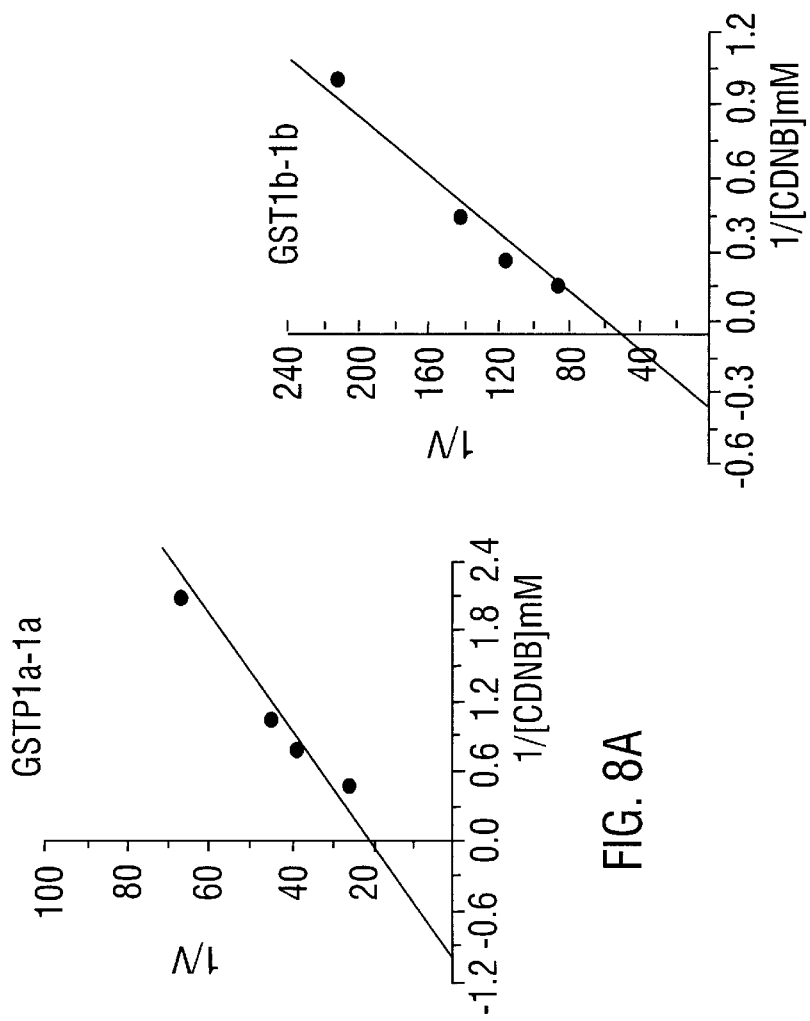
FIG. 8A
FIG. 8B
FIG. 8C

METHOD OF IDENTIFYING INHIBITORS OF GLUTATHIONE S-TRANSFERASE (GST) GENE EXPRESSION

This work was supported in part by grants CA55835 and POI CA 55261 from National Cancer Institute, National Institutes of Health, USA, and by a research grant award from the Kleberg Foundation.

BACKGROUND OF THE INVENTION

A. Field of the Invention

The present invention involves the field of cancer diagnosis and treatment. More specifically, the present invention relies on the identification and targeting of polymorphic forms of glutathione S-transferases (GSTs) in tumor cells.

B. Related Art

The glutathione S-transferases, or GSTs are a family of proteins whose best known function is the catalysis of the neutrophilic attack of the sulfur atom of glutathione by electrophilic groups of a variety of endogenous and exogenous compounds, including many mutagens, carcinogens, alkylating anticancer agents and electrophilic products of xenobiotic metabolism (Mannervik and Danielson, 1988; Pickett and Lu, 1989; Hayes and Pulford, 1995; Commandeur et al., 1995). The currently known human soluble GSTs are classified into four groups, α, μ, π and θ according to their N-terminal amino acid sequence homology, enzymatic substrate specificity, and antigenicity (Mannervik et al., 1992).

GSTs are involved in many cellular functions, the best characterized of which is their role as phase II enzymes in which they catalyze the S-conjugation of glutathione (GSH) with a wide variety of electrophilic compounds, including many mutagens, carcinogens, anticancer agents and their metabolites (Mannervik, 1985; Mannervik and Danielson, 1988; Pickett and Lu, 1989; Daniel, 1993; Boyland and Chasseaud, 1969; Coles and Ketterer, 1980; Ketterer and Sies, 1987; Sato, 1989; Morrow and Cowan, 1990; Waxman, 1990; Tsuchida and Sato, 1992; Commandeur et al., 1995).

Significant over-expression of the GST-π gene is associated with malignant transformation, tumor drug resistance, and poor patient survival (Sato, 1989; Morrow and Cowan, 1990; Waxman, 1990; Tsuchida and Sato, 1992; Commandeur et al., 1995; Tidefelt et al., 1992; Muramatsu et al., 1993; Gilbert et al., 1993; Tew, 1994), and in many human tumors and pre-neoplastic lesions, the GST-π protein is over-expressed, even though, in the corresponding normal tissues the protein is either absent or expressed at very low levels.

The GST-π gene has been mapped to a relatively small region of chromosome 11q13 which contains a number of cancer-associated genes and proto-oncogenes, including, bcl1/prad1, int2 and hstf1, some of which have been reported to be co-amplified with the GST-π gene in some tumors (Lammie and Peters, 1991; Saint-Ruf et al., 1991). In human malignant gliomas, a positive correlation has been demonstrated between the level of GST-π expression (by immunocytochemistry) as well as both the histological grade of the tumor and patient survival (Saint-Ruf et al., 1991; Hara et al., 1990). An association between high GST-π protein expression and 2-chloroethylnitrosourea resistance in some human glioma cell lines also has been demonstrated (Ali-Osman et al., 1990).

The nucleotide sequences of the complete human GST-π cDNA and GST-π gene reported to date from a variety of sources (Kano et al., 1987; Moscow et al., 1988; Cowell et al., 1988; Morrow et al., 1989) suggest that only one human GST-π gene exists (Mannervik et al., 1992). The isolation of two different GST-π proteins (Ahmad et al., 1990) from human placenta, however, strongly suggests that genetic polymorphism may exist in the human GST-π gene locus. Whether or not this putative polymorphic nature plays a role in tumorigenesis remains unclear, and thus it is important to explore both the structural and functional variation in this gene locus.

SUMMARY OF THE INVENTION

It is, therefore, a goal of the present invention to exploit the association of GST-π with certain forms of malignancy. More specifically, it is a goal of the present invention to provide methods of diagnosis and treatment for cancers based on the differential involvement of variant forms of GST-π. It also is, therefore, a goal to provide compositions that facilitate such diagnostic and therapeutic endeavors including genes, polypeptides, oligonucleotides, peptide fragments and antibodies.

In accordance with these objectives, there is provided a method for inhibiting growth of a tumor cell comprising reducing the activity level of at least one of hGSTP1*B protein or hGSTP1*C protein in said tumor cell.

In preferred embodiments, the reduction in the activity of hGSTP*B or of hGSTP*C protein is achieved by reducing the expression of said hGSTP1*B or hGSTP1*C protein. In certain embodiments, this reduction in expression is effected by contacting the tumor cell with an antisense nucleic acid that hybridizes to an hGSTP1*B or hGSTP1*C nucleic acid under intracellular conditions, but does not hybridize substantially to an hGSTP1*A nucleic acid under intracellular conditions.

In other embodiments, the hGSTP1*B or hGSTP1*C nucleic acid is an mRNA. In particular embodiments, the antisense nucleic acid is an mRNA expressed from a vector construct comprising at least a portion of said hGSTP1*B or hGSTP1*C nucleic acid. In yet other embodiments, the vector construct comprises at least a portion of the coding region of said hGSTP1*B or hGSTP1*C nucleic acid. In preferred embodiments, the coding region is derived from a cDNA. In other embodiments the vector construct including at least base +313 or +341 of SEQ ID NO:4.

In still further embodiments, the vector construct comprises at least a portion of transcribed but non-translated region of said hGSTP1*B or hGSTP1*C nucleic acid. In those embodiments where the vector construct comprises a portion of transcribed but non-translated region of the hGSTP1*B or hGSTP1*C nucleic acid, the region may be an intron.

In other embodiments, the vector construct comprises at least a portion of a translated region. In preferred embodiments the portion of a translated region comprises at least a portion of exons 5 and 6 from said hGSTP1*C nucleic acid.

The present invention also provides methods where the antisense nucleic acid may be a DNA molecule. In preferred embodiments, the DNA molecule is a cDNA molecule. In other aspects of the invention the DNA includes at least base +313 or +341 of SEQ ID NO:4.

The present invention further provides a method of reducing the expression of at least one of hGSTP1*B protein or hGSTP1*C protein in the tumor cell, wherein reducing the expression comprises contacting said tumor cell with a ribozyme that cleaves an hGSTP1*B or hGSTP1*C nucleic acid under intracellular conditions. In preferred embodiments, the ribozyme cleaves at least at about base +313 or +341 of SEQ ID NO:4.

In other aspects the present invention, there is provided a method of reducing the expression of hGSTP1*B protein or hGSTP1*C protein in tumor cells, wherein reducing the activity comprises contacting the tumor cells with an antibody that binds immunologically to an hGSTP1*B or hGSTP1*C protein, but that does not bind substantially to an hGSTP1*A protein. In one such embodiment the antibody binds to an epitope that includes residue 104 or 113 of SEQ ID NO:3. In certain embodiments in which the expression of hGSTP1*B protein or hGSTP1 *C protein in a tumor cell is reduced, the tumor cell is in a human subject.

Another aspect of the present invention provides a method for increasing the growth inhibitory activity of an alkylating agent in a tumor cell comprising reducing the activity level of at least one of hGSTP1*B protein or hGSTP1*C protein in said tumor cell.

In yet another embodiment, the present invention provides an isolated polypeptide having the sequence of hGSTP1*B (SEQ ID NO:1). In still another embodiment the present invention provides an isolated polypeptide having the sequence of hGSTP1*C (SEQ ID NO:3). In preferred embodiments the present invention provides an isolated nucleic acid encoding hGSTP1*B (SEQ ID NO:1). An isolated nucleic acid encoding hGSTP1*C (SEQ ID NO:3) is provided in another aspect of the present invention In those embodiments that provide an isolated nucleic acid encoding hGSTP1*B, a preferred sequence is that of SEQ ID NO:2. In those embodiments that provide an isolated nucleic acid encoding hGSTP1*C, a preferred sequence is that of SEQ ID NO:4.

The present invention provides an expression vector comprising a nucleic acid encoding at least a portion of hGSTP1*B (SEQ ID NO:1). The present invention further provides an expression vector comprising a nucleic acid encoding at least a portion of hGSTP1*C (SEQ ID NO:3).

In certain embodiments where the expression vector comprises a nucleic acid encoding at least a portion of hGSTP1*B (SEQ ID NO:1), the sequence may be that of SEQ ID NO:2. In other embodiments where the expression vector comprises a nucleic acid encoding at least a portion of hGSTP1*C (SEQ ID NO:3), the sequence may be that of SEQ ID NO:4. In some embodiments, the nucleic acid is positioned antisense to, and under the control of, a promoter active in eukaryotic cells.

The present invention further provides an antibody that binds immunologically to at least one of an hGSTP1*B or hGSTP1*C protein, but does not bind to an hGSTP1*A protein. In preferred embodiments, the antibody binds to an epitope that includes at least residue 104 or 113 of SEQ ID NO:3.

Other embodiments of the present invention provide an antisense nucleic acid that hybridizes to an hGSTP1*B or hGSTP1*C nucleic acid under intracellular conditions, but does not hybridize substantially to an hGSTP1*A nucleic acid under intracellular conditions.

Also provided by the present invention is a ribozyme that cleaves an hGSTP1*B or hGSTP1*C nucleic acid under intracellular conditions, but does not substantially cleave an hGSTP1*A nucleic acid under intracellular conditions.

The present invention further provides a method of preparing a molecule that binds to an hGSTP1*B or hGSTP1*C protein but does not substantially bind to an hGSTP1*A protein. The method may comprise determining a three-dimensional structure of an hGSTP1*B or hGSTP1*C protein and designing a molecule that binds to an hGSTP1*B or hGSTP1*C protein, but that does not bind substantially to an hGSTP1*A protein. In some embodiment the method further comprises testing the designed molecule for binding to said hGSTP1*B or hGSTP1*C protein. In yet other embodiment the method may comprise testing the designed molecule for binding to said hGSTP1*A protein.

In another aspect, the present invention discloses methods for the identification of a candidate inhibitor substance that inhibits GST-π activity comprising the steps of: contacting a cell expressing a GST-π protein with a candidate inhibitor substance; and comparing the growth of said cell with the growth of said cell in the absence of said candidate inhibitor substance; wherein an increase in growth is indicative of said substance being an inhibitor of GST-π activity. In certain embodiments, the GST-π protein being expressed is GSTP*B. In other embodiments the GST-π protein being expressed is GSTP*C. In yet other embodiments the GST-π protein being expressed is not GSTP*A.

In some embodiments, the candidate inhibitor substance is an antisense molecule to an hGSTP1*B or hGSTP1*C nucleic acid under intracellular conditions. In other preferred embodiments the candidate substance is a ribozyme that cleaves an hGSTP1*B or hGSTP1*C nucleic acid under intracellular conditions. In certain other embodiments, the candidate substance is a small molecule inhibitor. In those embodiments where the candidate substance is a small molecule inhibitor, the candidate substance may be a substituted isoxazole, heterocyclic aromatic compound; or a sugar-linked aromatic compound.

The present invention further discloses a method for the identification of a candidate inhibitor substance that inhibits GST-π expression. In preferred embodiments, the method comprises the steps of: contacting a cell expressing a GST-π protein with a candidate inhibitor substance and comparing the expression of GST-π of said cell with the expression of GST-π of said cell in the absence of said candidate inhibitor substance; wherein a decrease in the expression of GST-π is indicative of said substance being an inhibitor of GST-π expression. In particular embodiments, the candidate substance for the inhibition of expression of GST-π proteins is an antisense molecule to an hGSTP1*B or hGSTP1*C nucleic acid under intracellular conditions. In other embodiments of the present invention, the candidate substance is a ribozyme that cleaves an hGSTP1*B or hGSTP1*C nucleic acid under intracellular conditions.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein:

FIGS. 2A and 2B. FIG. 2A: Subclones of SuperCos-GSTpi for DNA sequencing of entire GST-π gene. PBS.GST-π/A (exons 2 and 3, and intron 2), pBS.GST-π/B (exons 3 to 6 and introns 3 to 5), pBS.GST-π/C (exons 6 and 7, intron 6, and 3'-untranslated region) and pBS.GST-π/D (exons 2 to 7 and introns 2 to 6). FIG. 2B: DNA sequencing strategy used to obtain the complete GST-π gene nucleotide sequence. Arrows indicate the sequencing directions of the primers. Sequencing was performed at least twice in both directions.

FIGS. 6A, 6B, 6C, 6D, 6E, 6F, and 6G. Strategy used to obtain the entire nucleotide sequences of the three GST-π cDNA variants. The arrows indicate both the directions and the regions sequenced.

FIG. 6B. Nucleotide and predicted amino acid sequence for GSTPI*A, GSTPI*B and GSTPI*C.

FIGS. 8A–C. Lineweaver-Burke plots for the catalysis of the conjugation of GSH with CDNB by GSH-affinity chromatography purified recombinant GSTP1a-1a (FIG. 8A), GSTP1b-1b (FIG. 8B) and GSTP1c-1c (FIG. 8C). Reaction rates were determined with 2.5 mM GSH and 0.015 unit of each enzyme.

(FIG. 10A: GSTPI*A; FIG. 10B: GSTPI*B; FIG. 10C: GSTPI*C);

FIG. 12A) all glioma patients; FIG. 12B) glioblastoma multiforme patients.

FIG. 13A) all glioma patients; FIG. 13B) glioblastoma multiforme patients.

DETAILED DESCRIPTION OF THE PREFERRED EMBODIMENTS

A. The Present Invention

Figure 1:
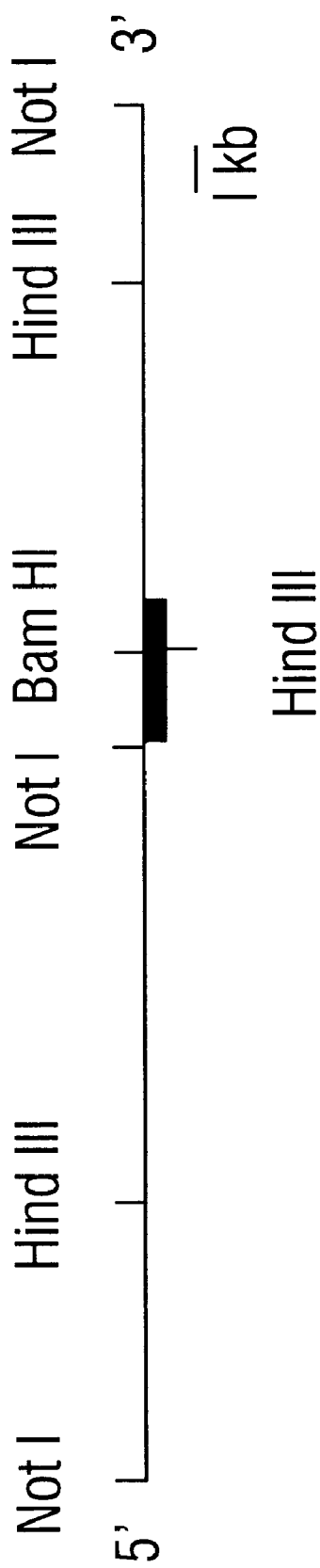
FIG. 1. A simplified restriction map of SuperCos-GSTpi. The solid box corresponds to the position of the isolated GST-π gene.

The human GST-π gene and its cDNA (Kano et al., 1987; Moscow et al., 1988) have been previously described, and based on the identical nucleotide sequences observed in four different reports, it has been generally accepted that only one human GST-π gene exists (Mannervik et al., 1992). However, as described herein, three different full-length GST-π cDNAs (hGSTP1*A, hGSTP1*B, and hGSTP1*C SEQ ID NO:3, SEQ ID NO:5 AND SEQ ID NO:7, respectively) were isolated from λgt11 libraries prepared from human malignant glioma cells. hGSTP1*A, was identical to the GST-π gene described in previous reports (Kano et al., 1987; Moscow et al., 1988); the other two cDNAs were, however, new. Their respective encoded peptides, GSTP1a, GSTP1b and GSTP1c, are closely related and arise from two nucleotide transitions of A→G and C→T at positions +313 and +341, respectively, of the cDNAs.

Intracellular stabilities of the variant mRNAs were determined and the proteins encoded by the GST-π cDNAs were expressed in *E. coli*, purified by GSH-affinity chromatography, and used in enzyme kinetic analyses to determine the functional consequences of the structural differences. To further examine the structural consequences of the amino acid alterations in the encoded GST-π peptides, computer modeling was used to introduce the amino acid changes into the three-dimensional structure of the placental GST-π proteins that had been previously isolated and co-crystallized with S-hexylglutathione (Reindeer et al., 1992). The expression of each of the gene variants in primary specimens, cell lines of malignant gliomas, normal brain, normal placenta and peripheral blood lymphocytes was investigated and the concordance of the observed genotype and phenotype was determined by DNA-PCR and RNA-PCR of representative specimens. Preliminary analysis of the distribution frequency of the gene variants in tumor and normal specimens were performed. The results are summarized below.

The presence and expression of the variant GST-π mRNA in both normal and malignant specimens indicate allelopolymorphism of the GST-π gene locus, rather than mutations. One of the placental tissues examined here expressed hGSTP1*B exclusively. In a prior report (Ahmad et al., 1990), a GST-π protein isolated from human placenta was shown to have the $Ile_{104} \rightarrow Val_{104}$ substitution caused by the A→G transition at +313 in hGSTP1*B. However, since neither the gene encoding this GST-π peptide nor the cDNA corresponding to its mRNA had been previously described, the results were inconclusive as to whether this protein was a new GST-π gene, or emanated from a naturally-occurring polymorphism of a known GST-π gene. Similarly, until now, there has been no report of the isolation of the full-length hGSTP1*C cDNA or gene. A truncated cDNA encoding 176 amino acids (83.8%) of the N-terminus of hGSTP1*C has previously been isolated from a human lung λgt11 cDNA library (Board et al., 1989). Comparison of the nucleotide sequences of the human GST-π cDNAs reported here with that of the rat orthologue, GSTP (Sakai et al., 1987) showed codons 104 and 113 to be among those altered in the GST-π cDNAs of the two species, with changes from human to rat of $Ile_{104} \rightarrow Gly_{104}$ and $Ala_{113} \rightarrow Asn_{113}$. This suggested that these positions are among the least conserved in the GST-π gene from an evolutionary standpoint.

The nucleotide transitions giving rise to the GST-π variants also altered several restriction endonuclease recognition sites in the variant cDNAs, thus allowing characterization of the cDNAs by restriction endonuclease mapping using the restriction enzymes, Mae II and Xcm I. This technique of determining GST-π subtype is simple, rapid and specific, and is suitable for screening large numbers of specimens. Alternatively, the GST-π phenotype/genotype can be determined by southern or northern hybridizations with oligonucleotide probes specific for the different variants, as was demonstrated in this study. However, because of cross-hybridization, the specificity of the latter procedure is limited, particularly, for differentiating hGSTP1*B from the other two GST-π variants. Furthermore, it does not allow conclusive detection of mixtures of GST-π genes or mRNAs in a single specimen. This is best achieved by restriction mapping and nucleotide sequencing.

Following transcriptional block with actinomycin D, the present inventors observed only a modest difference in the intracellular half-lives of the mRNA transcripts between the variant GST-π genes. hGSTP1*A transcripts were least stable ($t_{1/2}$ of 9.4 hrs), while transcripts of hGSTP1*B were most stable, with a half-life of 14.1 hrs. Overall, the observed half-lives were longer than the 3.8 hrs to 8.6 hrs (after ethacrynic acid treatment) previously reported for GST-π transcripts in other cell types (She et al., 1995).

Using computer modeling, the inventors have created the three-dimensional structures of the peptides encoded by the genes, hGSTP1*B and hGSTP1*C, namely, GSTP1b and GSTP1c, from the previously determined X-ray crystallographic structure of GSTP1a (Reindeer et al., 1992; Reinemer et al., 1993). Energy minimizations of the resulting structures showed significant deviations in atomic coordinates and inter-side chain distances of five of the six key H-site amino acid residues caused by the amino acid changes. Of the affected residues, $Tyr_{108}$ was the most altered, particularly, with respect to its distances to $Val_{10}$, $Val_{35}$ and $Tyr_7$. The changes are much larger as one progresses from GSTP1a to either GSTP1b or GSTP1c than from GSTP1b to GSTP1c, indicating a greater impact on active site structure and function by the +313 transition than by the change at +341.

Predictions from the structural modeling data are supported by the enzyme kinetic differences the inventors observed between the three variant GST-π enzymes. In catalyzing the conjugation of GSH with CDNB, the Km for CDNB of GSTP1a-1a was approximately 3-fold lower than that of either GSTP1b-1b or GSTP1c-1c. The Vmax values also differed similarly between the three enzymes. These results are in agreement with those in a previous study (Zimniak et al., 1994), at least for GSTP1b, in which a 4-fold lower Km value for CDNB was observed for recombinant GSTP1a-1a relative to GSTP1b-1b, produced from a GSTP1*c cDNA, created artificially by site-directed mutagenesis. The data suggest that the observed enzyme kinetic effects of the $Val_{140}$ substitution are, at least in part, the result of steric effects caused by substituting $Val_{104}$ for $Ile_{104}$ in the GST-π active (H-) site.

The computer modeling study showed that the $Ile_{104} \rightarrow Val_{104}$ substitution in GSTP1b-1b and GSTP1c-1c significantly affected 5 of the 6 amino acids lining the H-site, and caused significant shifts in the side chains of the residues sterically restricted the region of the H-site bordered by $Tyr_{108}$, $Val_{35}$, $Val_{10}$ and, to a lesser extent $Phe_8$, while opening up the region bordered by $Tyr_7$ and $Val_{10}$. These findings suggest that bulky substrates may fit better in the space lined by these residues and $Ile_{104}$, while less bulky ones may bind better in the larger space lined by $Val_{104}$ and might explain previous findings that the Km of GSTP1a-1a for CDNB was lower than that for GSTP1b-1b, while the opposite was true for the bulkier bromosulphthalein (Zimniak et al., 1994).

An additional basis for the functional differences observed between the variant GST-π proteins could reside in the fact that domain II of the GST-π peptide, in which the H-site resides, contains five α-helices, two of which (αD [$AA_{81-107}$] and αE [$AA_{109-132}$]) contain the amino acid substitutions of $Ile_{104} \rightarrow Val_{104}$ and $Ala_{113} \rightarrow Val_{113}$ (Reindeer et al., 1992; Reinemer et al., 1993). A right-handed super-helix exists in this region, generated, in part, by an up-down arrangement of αD and αE and a cross-over connection between αE and a third helix, αF to form a superhelix (Reindeer et al., 1992; Reinemer et al., 1993). In a previous study, it has been shown that the thermodynamic propensities of Ile, Ala and Val to contribute to the α-helical structure in a protein differ significantly (Blaber et al., 1993), as indicated by the computed free energy ($\Delta\Delta G$) when the protein folds to the native α-helix structure. Consequently, the changes of Ile or Ala to Val could result in subtle alterations in the α-helical or super-helical structure that can affect H-site architecture, and ultimately, result in differences in substrate binding affinities and catalytic activities between the GST-π enzymes.

This, indeed, was found in this study for all three proteins, using the substrate CDNB, and for GSTP1a-1a and GSTP1b-1b with other substrates (Zimniak et al., 1994). Interestingly, recombinant GSTP1a-1a lost its activity at 45° C. at twice the rate of GSTP1b-1b or GSTP1c-1c. A similar difference in thermostability between GSTP1a and GSTP1b has been previously reported (Zimniak et al., 1994). The inventors speculate that this might be due to differential changes in H-site stability induced by the increased temperature, and differences in the free energy of the α-helix formed with the different amino acids at codons 104 and 113.

An important implication of the observed differences between the variant GST-π proteins with respect to their Km values for CDNB is that the use of CDNB to determine GST activity in cells or tissues containing different GST-π variant proteins will yield results that underestimate the contribution of GSTP1b-1b and GSTP1c-1c, relative to GSTP1a-1a.

However, the present inventors have shown that such a quantitative determination can be made with an ELISA assay using placental GST-π antibodies, which, as shown herein, cross-react with all three GST-π proteins.

The results of the distribution frequencies of the different GST-π gene variants among the specimens showed hGSTP1*C to be present at a 4-fold higher frequency in malignant gliomas than in normal tissues, primarily lymphocytes. Conversely, hGSTP1*A is more frequently present in normal cells and tissues than in gliomas. Further studies will clarify whether the higher frequency of GSTP1*C in tumors represents a clonal selection or a loss of heterozygosity associated with the malignant process. In contrast to the other two GST-π genes, hGSTP1*B appears to be a relatively rare allele, and homozygously, was not present in any of the tumor specimens or cell lines studied. It is also intriguing that none of the specimens examined was heterozygous for hGSTP1*B and hGSTP1*C. It may be that the functionally different GST-π proteins provide a mechanism for fine-tuning/regulation of GST-π activity in cells and tissues and, as such, because of the similar catalytic properties of GSTP1b-1b and GSTP1c-1c, no biological advantage exists in co-expressing these two GST-π's in a single cell or tissue. Future studies will determine whether the different GST-π peptides dimerize to equal degrees with each other and yield GST-π proteins with different catalytic activities for different substrates.

It is reasonable to expect that the differences in H-site structure of the variant GST-π proteins will result in differences in the binding affinity for different mutagens, carcinogens and alkylating anticancer agents to this site, and subsequently, in a differential ability of the enzymes to catalyze the conjugation of these compounds to GSH. This will have significant implications with respect to the risk of individuals, having different GST-π genotypes and/or phenotypes, to develop cancer. It also should provide a basis for rationally designing novel GST-π-targeted anticancer therapies, as described in the examples.

Extending the above studies to the genomic level, an isolated hGSTP1*C gene was localized within 2.1 kB Not I/HinD III and 11.5 kB HinD III fragments of a cosmid vector clone designated SuperCos-GSTpi. The 3116 base pairs included 161 bp upstream of the initiating methionine ATG codon and 222 nucleotides downstream of the TGA stop codon, and encodes 210 amino acids in seven exons. Exon-intron organization was determined by identification of the AG/GT splicing signals and by comparison of the sequence with the sequence of the previously described GST-π cDNA from this cell line (Ali-Osman et al., 1990). The promoter region of the isolated gene was similar to that previously described by Cowell et al. (1988) and Morrow et al. (1989), and contained all the regulatory elements, TATA box and both the AP1 and two SP1 sites, previously reported. In addition, however, an anti-oxidant response element (ARE) was identified in the AP1 site of the gene. This ARE has subsequently been identified in the previously described GST-π gene. The sequence is identical to the ARE core sequence (GTGACTCAGC) of the human NAD(P) H:quinone oxidoreductase gene (Hayes and Pulford, 1995; Xia et al., 1991), and has a high degree of homology to the ARE (GTGACAAAGC SEQ ID NO:32) in the rat GST Ya gene (Hayes and Pulford, 1995; Li and Jaiswal, 1992).

The major differences between the "c" variant GST-π gene described here and the gene previously reported are the nucleotide transitions of A→G at +1404 and C→T at +2294, which confirmed the isolated gene to be the hGSTP1*C variant of the GST-π. The ATC (Ile)→GTC (Val) and GCC (Ala)→GTC (Val) changes in codons 104 and 113, respectively, caused by these transitions were both in the electrophile binding (H-) site of the GST-π peptide.

Other structural differences between the isolated hGSTP1*C and the GST-π gene previously described included transitions in introns 5 and 6, which, although altering restriction cleavage sites useful in structural characterization of the gene, do not involve known regulatory motifs. A structural difference of potential functional significance, however, was the guanine insertion at +51 in the conserved IRE (CCCGCGTC) in intron 1. This IRE is highly homologous to the IRE-A (CCCGCCTC) in the human glyceraldehyde-3-phosphate dehydrogenase gene (Nasrin et al., 1990), and to the IRE in the GST-π gene isolated from both the HPB-ALL and MCF-7 cell lines (Cowell et al., 1988, Morrow et al., 1989), and may account for the activation of the GST-π gene by insulin (Ahmad et al., 1990). It remains to be established whether the single guanine insertion in the IRE of the hGSTP1*C gene described here is a common feature of glioma cells and whether it significantly alters insulin-binding, and ultimately insulin-responsiveness of the GST-π gene.

The identification, for the first time, of functional RAREs in the GST-π gene is a particularly important finding of this study. The identified sequences are highly homologous to the RARE half site, 5'-A(G)GG(T)TC(G)A-3' present in other RA-responsive genes, such as, those encoding RAR types α2, β2 and γ2 (Xia et al., 1996; Board et al., 1989; Hoffnan, 1990; Favreau and Pickett, 1990; Leroy et al., 1991; Lehmann et al., 1992; Smith et al., 1991; Mangelsdorf et al., 1991; Pikarsky et al., 1994), and the cellular retinoic acid and retinol binding proteins (CRABPs and CRBPs) (Mangelsdorf et al., 1991; Pikarsky et al., 1994; Boylan and Gudas, 1991; Durand et al., 1992; , 1992; Yang-Yen et al.; Schule et al., 1991). In the hGSTP1*C gene, the four repeats of RARE consensus half sites and the one palindromic halfsite are all located in intron 5, in contrast to the majority of previously described RARES, which are cis-acting and occur in the promoter regions of the genes regulated. It is, however, not unusual for regulatory motifs to be present within introns. Indeed, in a variety of genes, including oncogenes, tumor suppressor genes, growth-factor and growth factor receptor genes (Vasios et al., 1989; Stumpo et al., 1988; Taub et al., 1987; Lozano and Levine, 1991; Jung et al., 1993; Takimoto and Kuramoto, 1993; Chrysogelos, 1993; Chen et al., 1994), functional intronic regulatory elements are located distant in primary structure from the transcription start site of the regulated genes. In the GST-π gene, the RARE motif is approximately 1,500 bp from the transcription start site, a distance similar to that of the tissue-specific regulatory element in the p53 gene (Taub et al., 1987) and the two negative regulatory elements of the PDGF-A chain gene (Lozano and Levine, 1991) from their transcription start sites.

Two of the RAREs in hGSTP1*C are separated by five nucleotides and two others by 13 nucleotides, which correspond to the minimal nucleotide spacer required for RARE functionality (Xia et al., 1996). These two RAREs are therefore likely to be the functional RAREs in the hGSTPI*C gene. Using a gel mobility shift assay, it was showed that nuclear protein extracts from MGR-3 cells in which RAR-β had been induced by prior treatment with all-trans RA, contained a fraction that bound specifically to the RAREs in the hGSTP1*C gene. Furthermore, following all-trans RA treatment, expression of the GST-π gene was increased significantly in MGR-3 cells. Since functionality of RAREs requires binding to RA-RAR complexes (Glass et al., 1991), these data provide strong evidence that the RAREs in the hGSTP1*C gene are functional, and suggest that the RA-RAR-RARE binding may contribute, at least in part, to the observed activation of the GST-π gene by alltrans retinoic acid in the MGR-3 cell line. The results contrast with those of a previous study in which a down-regulation of the GST-π gene was observed in a GST-π-CAT fusion gene construct following exposure to all-trans retinoic acid (Xia et al., 1993). Recent evidence, using CAT plasmid deletion constructs, also showed that the AP1 site in the GST-π promoter is required for RA-mediated gene suppression (Xia et al., 1996).

Based on these observations, the data shown here, and the known RA-mediated up- and down-regulation of RA responsive genes (Lehmann et al., 1992), a model is proposed in which activation and suppression of the GST-π gene by RA occurs by two separate mechanisms. In this model, the GST-π gene is activated by the binding of the RA-RAR complex to RAREs in the gene. Suppression of the GST-π gene, on the other hand, occurs via competitive inhibition of the binding of AP1-binding proteins, such as jun and fos, to the AP1 DNA site by the RA-RAR complex, as has been previously suggested (Xia et al., 1996; Schule et al., 1991). Such a model is consistent with a proposed general mechanism for RA-mediated gene regulation by ligand-activated RARs (Lehmann et al., 1992; Durand et al., 1992; Fanjui et al., 1994). The latter mechanism of RA induction of GST-π gene expression, may constitute part of the molecular basis for the cancer preventive action of long-term administration of retinoic acid (Lipman et al., 1987). The activation of the GST-π gene by all-trans RA in MGR-3 cells observed in this study was a delayed process, similar to the late transcriptional induction of the laminin B1 gene by RA (Vasios et al., 1991), and consistent with a mechanism involving RAR-ligand binding to RARES.

These results and observations are exploited, according to the present invention, as described in detail in the following sections.

B. Polypeptides and Peptides

The present invention, in one embodiment, encompasses the new GST-π amino acid sequences discussed above. The present invention also encompasses hybrid molecules containing portions from one GST-π fused with portions of another. Alternatively, a fusion of this sort could be generated with sequences all three variants in a single polypeptide molecule. Also encompassed are fragments of the disclosed molecules, as well as insertion, deletion or replacement mutants in which non-GST-π sequences are introduced, GST-π sequences are removed, or GST-π sequences are replaced with non-GST-π sequences, respectively.

GST-π's, according to the present invention, may be advantageously cleaved into fragments for use in further structural or functional analysis, or in the generation of reagents such as GST-π-related polypeptides and GST-π-specific antibodies. This can be accomplished by treating purified or unpurified GST-π's with a peptidase such as endoproteinase glu-C (Boehringer, Indianapolis, Ind.). Treatment with CNBr is another method by which GST-π fragments may be produced from natural GST-π. Recombinant techniques also can be used to produce specific fragments of GST-π.

More subtle modifications and changes may be made in the structure of the encoded GST-π polypeptides of the present invention and still obtain a molecule that encodes a protein or peptide with characteristics of the natural GST-π polypeptides, including the variants described above. The following is a discussion based upon changing the amino acids of a protein to create an equivalent, or even an improved, second-generation molecule. The amino acid changes may be achieved by changing the codons of the DNA sequence, according to the following codon table, Table A:

TABLE A

| Amino Acid Names and abbreviations | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG CUA | CUC CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG CGA | CGC CGG | CGU |
| Serine | Ser | S | AGC | AGU UCA | UCC UCG | UCU |
| Threonine | Thr | T | ACA | ACC ACG | ACU | |
| Valine | Val | V | GUA | GUC GUG | GUU | |
| Tryptophan | Trp | W | UGG | | | |
| Tyrosine | Tyr | Y | UAC | UAU | | |

It is known that certain amino acids may be substituted for other amino acids in a protein structure in order to modify or improve its antigenicity or activity (see, e.g., Kyte & Doolittle, 1982; Hopp, U.S. Pat. No. 4,554,101, incorporated herein by reference). For example, through the substitution of alternative amino acids, small conformational changes may be conferred upon a polypeptide which result in increased activity or stability. Alternatively, amino acid substitutions in certain polypeptides may be utilized to provide residues which may then be linked to other molecules to provide peptide-molecule conjugates which retain enough antigenicity of the starting peptide to be useful for other purposes. For example, a selected GST-π peptide bound to a solid support might be constructed which would have particular advantages in diagnostic embodiments.

The importance of the hydropathic index of amino acids in conferring interactive biological function on a protein has been discussed generally by Kyte & Doolittle (1982), wherein it is found that certain amino acids may be substituted for other amino acids having a similar hydropathic index or core and still retain a similar biological activity. As displayed in Table B below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules. Preferred substitutions which result in an antigenically equivalent peptide or protein will generally involve amino acids having index scores within ±2 units of one another, and more preferably within 1 unit, and even more preferably, within ±0.5 units.

TABLE B

| Amino Acid | Hydropathic Index |
|---|---|
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, for example, isoleucine, which has a hydropathic index of +4.5, will preferably be exchanged with an amino acid such as valine (+4.2) or leucine (+3.8). Alternatively, at the other end of the scale, lysine (−3.9) will preferably be substituted for arginine (−4.5), and so on.

Substitution of like amino acids may also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with an important biological property of the protein.

As detailed in U.S. Pat. No. 4,554,101, each amino acid has also been assigned a hydrophilicity value. These values are detailed below in Table C.

TABLE C

| Amino Acid | Hydrophilic Index |
|---|---|
| arginine | +3.0 |
| lysine | +3.0 |
| aspartate | +3.0 ± 1 |
| glutamate | +3.0 ± 1 |
| serine | +0.3 |
| asparagine | +0.2 |
| glutamine | +0.2 |
| glycine | 0 |
| threonine | −0.4 |
| alanine | −0.5 |
| histidine | −0.5 |
| proline | −0.5 ± 1 |
| cysteine | −1.0 |
| methionine | −1.3 |
| valine | −1.5 |

TABLE C-continued

| Amino Acid | Hydrophilic Index |
|---|---|
| leucine | −1.8 |
| isoleucine | −1.8 |
| tyrosine | −2.3 |
| phenylalanine | −2.5 |
| tryptophan | −3.4 |

It is understood that one amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

Accordingly, these amino acid substitutions are generally based on the relative similarity of R-group substituents, for example, in terms of size, electrophilic character, charge, and the like. In general, preferred substitutions which take various of the foregoing characteristics into consideration will be known to those of skill in the art and include, for example, the following combinations: arginine and lysine; glutamate and aspartate; serine and threonine; glutamine and asparagine; and valine, leucine and isoleucine.

In addition, peptides derived from these polypeptides, including peptides of at least about 6 consecutive amino acids from these sequences, are contemplated. Alternatively, such peptides may comprise about 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 consecutive residues. For example, a peptide that comprises 6 consecutive amino acid residues may comprise residues 1 to 6, 2 to 7, 3 to 8 and so on of the GST-π protein. Such peptides may be represented by the formula $x$ to $(x+n)$=5' to 3' the positions of the first and last consecutive residues where x is equal to any number from 1 to the full length of the GST-π protein and n is equal to the length of the peptide minus 1. Where the peptide is 10 residues long (n=10−1), the formula represents every 10-mer possible for each antigen. For example, where x is equal to 1 the peptide would comprise residues 1 to (1+[10−1]), or 1 to 10. Where x is equal to 2, the peptide would comprise residues 2 to (2+[10−2]), or 2 to 11, and so on.

Syntheses of peptides are readily achieved using conventional synthetic techniques such as the solid phase method (e.g., through the use of a commercially available peptide synthesizer such as an Applied Biosystems Model 430A Peptide Synthesizer). Peptides synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of 7.0 to 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptide(s) are stored in a lyophilized or powdered state, they may be stored virtually indefinitely, e.g., in metered aliquots that may be rehydrated with a predetermined amount of water (preferably distilled, deionized) or buffer prior to use.

Of particular interest are peptides that represent antigenic epitopes that lie within the GST-π polypeptides of the present invention. An "epitope" is a region of a molecule that stimulates a response from a T-cell or B-cell, and hence, elicits an immune response from these cells. An epitopic core sequence, as used herein, is a relatively short stretch of amino acids that is structurally "complementary" to, and therefore will bind to, binding sites on antibodies or T-cell receptors. It will be understood that, in the context of the present disclosure, the term "complementary" refers to amino acids or peptides that exhibit an attractive force towards each other. Thus, certain epitopic core sequences of the present invention may be operationally defined in terms of their ability to compete with or perhaps displace the binding of the corresponding GST-π antigen to the corresponding GST-π-directed antisera.

The identification of epitopic core sequences is known to those of skill in the art. For example U.S. Pat. No. 4,554,101 teaches identification and preparation of epitopes from amino acid sequences on the basis of hydrophilicity, and by Chou-Fasman analyses. Numerous computer programs are available for use in predicting antigenic portions of proteins, examples of which include those programs based upon Jameson-Wolf analyses (Jameson and Wolf, 1988; Wolf et al., 1988), the program PepPlot® (Brutlag et al., 1990; Weinberger et al., 1985), and other new programs for protein tertiary structure prediction (Fetrow & Bryant, 1993) that can be used in conjunction with computerized peptide sequence analysis programs.

In general, the size of the polypeptide antigen is not believed to be particularly crucial, so long as it is at least large enough to carry the identified core sequence or sequences. The smallest useful core sequence anticipated by the present disclosure would be on the order of about 6 amino acids in length. Thus, this size will generally correspond to the smallest peptide antigens prepared in accordance with the invention. However, the size of the antigen may be larger where desired, so long as it contains a basic epitopic core sequence.

C. Polynucleotides and Oligonucleotides

In addition to polypeptides, the present invention also encompasses nucleic acids encoding the GST-π's discussed above. Because of the degeneracy of the genetic code, many other nucleic acids also may encode a given GST-π. For example, four different three-base codons encode the amino acids alanine, glycine, proline, threonine and valine, while six different codons encode arginine, leucine and serine. Only methionine and tryptophan are encoded by a single codon. Table A provides a list of amino acids and their corresponding codons for use in such embodiments. In order to generate any nucleic acid encoding GST-π, one need only refer to the codon table provided herein. Substitution of the natural codon with any codon encoding the same amino acid will result in a distinct nucleic acid that encodes GST-90. As a practical matter, this can be accomplished by site-directed mutagenesis of an existing GST-π gene or de novo chemical synthesis of one or more nucleic acids.

The observations regarding site-directed mutagenesis and chemical synthesis, presented above with respect to substitutional mutants GST-π peptides and polypeptides, apply with equal force to the discussion of nucleic acids. More specifically, substitutional mutants generated by site-directed changes in the nucleic acid sequence that are designed to alter one or more codons of a given polypeptide or epitope may provide a more convenient way of generating large numbers of mutants in a rapid fashion. The nucleic acids of the present invention provide for a simple way to generate fragments (e.g., truncations) of GST-π, GST-π-GST-π fusion molecules (discussed above) and GST-π fusions with other molecules. For example, utilization of restriction enzymes, nucleases, linkers and ligases in the GST-π gene permits one to manipulate the structure of these genes, and the resulting gene products.

The nucleic acid sequence information provided by the present disclosure also allows for the preparation of relatively short DNA (or RNA) sequences that have the ability to specifically hybridize to gene sequences of the selected GST-π gene. In these aspects nucleic acid probes of an appropriate length are prepared based on a consideration of the coding sequence of the GST-π gene, or flanking regions near the GST-π gene, such as regions downstream and upstream in the GST-π gene in the chromosome. The ability of such nucleic acid probes to specifically hybridize to GST-π gene sequences lends them particular utility in a variety of embodiments. For example, the probes can be used in a variety of diagnostic assays for detecting of an inteact GST-π gene in a given sample. In addition, these oligonucleotides can be inserted, in frame, into expression constructs for the purpose of screening the corresponding peptides for reactivity with existing antibodies or for the ability to generate diagnostic or therapeutic reagents.

To provide certain of the advantages in accordance with the invention, the preferred nucleic acid sequence employed for hybridization studies or assays includes sequences that are complementary to at least a 10 to 20, or so, nucleotide stretch of the sequence, although sequences of 30 to 60 or so nucleotides are also envisioned to be useful. A size of at least 9 nucleotides in length helps to ensure that the fragment will be of sufficient length to form a duplex molecule that is both stable and selective. Though molecules having complementary sequences over stretches greater than 10 bases in length are generally preferred, in order to increase stability and selectivity of the hybrid, and thereby improve the quality and degree of the specific hybrid molecules obtained. Thus, one will generally prefer to design nucleic acid molecules having GST-π gene-complementary stretches of 15 to 20 nucleotides, or even longer, such as 30 to 60, where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

The probes that would be useful may be derived from any portion of the GST-π variants. Therefore, probes are specifically contemplated that comprise nucleotides 1 to 9, or 2 to 10, or 3 to 11 and so forth up to a probe comprising the last 9 nucleotides of the nucleotide sequence of each GST-π. Thus, each probe would comprise at least about 9 linear nucleotides of the nucleotide sequence, designated by the formula "n to n+8," where n is an integer from 1 to the number of nucleotides in the sequence. Longer probes that hybridize to the GST-π gene under low, medium, medium-high and high stringency conditions are also contemplated, including those that comprise the entire nucleotide sequence of the GST-π variants. This hypothetical may be repeated for probes having lengths of about 10, 11, 12, 13, 14, 15, 16, 17, 18, 19, 20, 25, 30, 35, 40, 45, 50, 60, 70, 80, 90, 100 and greater bases.

A variety of hybridization techniques and systems are known which can be used in connection with the hybridization aspects of the invention, including diagnostic assays such as those described in Falkow et al., U.S. Pat. No. 4,358,535. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15M–0.9M salt, at temperatures ranging from 20° C. to 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and the method of choice will generally depend on the desired results.

In certain embodiments, one may desire to employ nucleic acid probes to isolate variants from clone banks containing mutated clones. In particular embodiments, mutant clone colonies growing on solid media which contain variants of the GST-π sequence could be identified on duplicate filters using hybridization conditions and methods, such as those used in colony blot assays, to obtain hybridization only between probes containing sequence variants and nucleic acid sequence variants contained in specific colonies. In this manner, small hybridization probes containing short variant sequences of the GST-π gene may be utilized to identify those clones growing on solid media which contain sequence variants of the entire GST-π gene. These clones can then be grown to obtain desired quantities of the variant GST-π nucleic acid sequences or the corresponding GST-π antigen.

In diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, one will likely desire to employ an enzyme tag such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with nucleic acid-containing samples.

In general, it is envisioned that the hybridization probes described herein will be useful both as reagents in solution hybridizations as well as in embodiments employing a solid phase. In embodiments involving a solid phase, the test DNA (or RNA) from suspected clinical samples, such as exudates, body fluids (e.g., amniotic fluid, middle ear effusion, bronchoalveolar lavage fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

The nucleic acid encoding the variant sequences may be useful in conjunction with polymerase chain reaction (PCR) methodology to detect changes in the genomic make-up of cells, for example, of tumor cells. In general, by applying the PCR technology as set out, e.g., in U.S. Pat. No. 4,60,102, one may utilize various portions of the GST-π gene sequence as oligonucleotide probes for the PCR amplification of a defined portion of a GST-π nucleic acid in a sample. The amplified portion of the GST-π sequence may then be detected by hybridization with a hybridization probe containing a complementary sequence. In this manner, extremely small concentrations of nucleic acid may detected in a sample utilizing GST-π sequences.

Antisense Technology

In a specific application of a sequence that hybridizes to GST-π, the present invention contemplates the use of antisense constructs. The term "antisense" is intended to refer to polynucleotide molecules complementary to a portion of a RNA GST-π, or the DNA corresponding thereto. "Complementary" polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

The intracellular concentration of monovalent cation is approximately 160 mm (10 mm $Na^+$; 150 mM $K^+$). The intracellular concentration of divalent cation is approximately 20 mM (18 mM $Mg^+$; 2 mM $Ca^{++}$). The intracellular protein concentration, which would serve to decrease the volume of hybridization and, therefore, increase the effective concentration of nucleic acid species, is 150 mg/ml. Constructs can be tested in vitro under conditions that mimic these in vivo conditions.

Antisense constructs may be designed to bind to the promoter and other control regions, exons, introns or even exon-intron boundaries of a gene. It is contemplated that the most effective antisense constructs. for the present invention will include regions complementary to the mRNA start site. One can readily test such constructs simply by testing the constructs in vitro to determine whether levels of the target protein are affected. Similarly, detrimental non-specific inhibition of protein synthesis also can be measured by determining target cell viability in vitro.

As used herein, the terms "complementary" or "antisense" mean polynucleotides that are substantially complementary over their entire length and have very few base mismatches. For example, sequences of fifteen bases in length may be termed complementary when they have a complementary nucleotide at thirteen or fourteen nucleotides out of fifteen. Naturally, sequences which are "completely complementary" will be sequences which are entirely complementary throughout their entire length and have no base mismatches.

Other sequences with lower degrees of homology also are contemplated. For example, an antisense construct which has limited regions of high homology, but also contains a non-homologous region (e.g., a ribozyme) could be designed. These molecules, though having less than 50% homology, would bind to target sequences under appropriate conditions.

The polynucleotides according to the present invention may encode an GST-π gene or a portion of thereof that is sufficient to effect antisense inhibition of protein expression. The polynucleotides may be derived from genomic DNA, i.e., cloned directly from the genome of a particular organism. In other embodiments, however, the polynucleotides may be complementary DNA (cDNA). cDNA is DNA prepared using messenger RNA (mRNA) as template. Thus, a cDNA does not contain any interrupted coding sequences and usually contains almost exclusively the coding region(s) for the corresponding protein. In other embodiments, the antisense polynucleotide may be produced synthetically.

It may be advantageous to combine portions of the genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

As stated above, although the antisense sequences may be full length genomic or cDNA copies, or large fragments thereof, they also may be shorter fragments, or "oligonucleotides," defined herein as polynucleotides of 50 or less bases. Although shorter oligomers (8–20) are easier to make and increase in vivo accessibility, numerous other factors are involved in determining the specificity of base-pairing. For example, both binding affinity and sequence specificity of an oligonucleotide to its complementary target increase with increasing length. It is contemplated that oligonucleotides of 8, 9, 10, 11, 12, 13, 14, 15, 16, 17, 18, 19, 20, 25, 30, 35, 40, 45 or 50 base pairs will be used. While all or part of the gene sequence may be employed in the context of antisense construction, statistically, any sequence of 17 bases long should occur only once in the human genome and, therefore, suffice to specify a unique target sequence.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

Ribozymes

As an alternative to targeted antisense delivery, targeted ribozymes may be used. The term "ribozyme" is refers to an RNA-based enzyme capable of targeting and cleaving particular base sequences in both DNA and RNA. Ribozymes can either be targeted directly to cells, in the form of RNA oligonucleotides incorporating ribozyme sequences, or introduced into the cell as an expression vector encoding the desired ribozymal RNA. Ribozymes may be used and applied in much the same way as described for antisense polynucleotide. Ribozyme sequences also may be modified in much the same way as described for antisense polynucleotide. For example, one could incorporate non-Watson-Crick bases, or make mixed RNA/DNA oligonucleotides, or modify the phosphodiester backbone, or modify the 2'-hydroxy in the ribose sugar group of the RNA.

Alternatively, the antisense oligo- and polynucleotides according to the present invention may be provided as RNA via transcription from expression constructs that carry nucleic acids encoding the oligo- or polynucleotides. A general discussion of expression constructs and vectors is provided below.

Screening for Antisense and Ribozyme Inhibitors of GST-p Expression

The rationale of the antisense oligonucleotide or ribozyme therapeutic agents in this invention is that they can be used to down-regulate the expression of specific variants of the human GST-π gene by hybridizing with the mRNA transcripts of these genes and thereby preventing their translation into protein. By so doing the defense against therapy that the GST-π protein offers the tumor cell is blocked and the tumor becomes more sensitive to subsequent therapy. Additionally, by suppressing the expression of the GST-π gene in the tumor cell, the contribution of the GST-π protein to the rapid growth and progression of the tumor is diminished. In the rational design the antisense molecules to hybridize with relatively small regions (15 bases) of the GST-π mRNA. Such small region targeting has a distinct advantage over full-length antisense polynucleotide strategies because it allows for higher selectivity in the targeting of different regions of the gene, and enables us to specifically and differentially down-regulate expression of the different GST-π gene variants.

In certain embodiments the present invention provides Accordingly, in screening assays to identify antisense molecules which alter the expression of GST-π gene in for example cancer cells, are provided by the present invention. In these embodiments, the present invention is directed to a method for determining the ability of a candidate antisense or ribozyme molecule to decrease the GST-π expression of cancer cells, the method including generally the steps of:

(a) obtaining a cell with GST-π expression;

(b) admixing a candidate molecule with the cell; and (c) determining the ability of the candidate substance to inhibit the GST-π content of the cell.

To identify a candidate substance as being capable of decreasing GST-π expression, one would measure or determine the basal GST-π status of, for example a cancer cell prior to any additions or manipulation. One would then add the candidate molecule to the cell and redetermine the GST-π activity in the presence of the candidate molecule. A candidate antisense or ribozyme which decreases the GST-π expression or content of a cell relative to the composition in its absence is indicative of a candidate substance being an inhibitor of GST-π expression.

A significant decrease in GST-π expression, is represented by a decrease in GST-π protein levels of at least about 30%–40%, and most preferably, by decreases of at least about 50%, with higher values of course being possible. Assays that measure GST-π content in cells are well known in the art and may be conducted in vitro or in vivo, and have been described elsewhere in the specification.

Alternatively, it may be desirable simply to measure inhibition of growth of cancer cells, for example, by measuring growth according to the MTT assay. A significant inhibition in growth is represented by decreases of at least about 30%–40% as compared to uninhibited, and most preferably, of at least about 50%, with more significant decreases also being possible. Growth assays as measured by the MTT assay are well known in the art. Assays may be conducted as described by Mosmann et al., 1983; Rubinstein et al., 1990 (incorporated herein by reference). Therefore, if a candidate molecule exhibited inhibition of growth of cancer cells in this type of study, it would likely be a suitable compound for use in the present invention.

Quantitative in vitro testing of the antisense or ribozyme molecules is not a requirement of the invention as it is generally envisioned that the agents will often be selected on the basis of their known properties or by structural and/or functional comparison to those agents already demonstrated to be effective. Therefore, the effective amounts will often be those amounts proposed to be safe for administration to animals in another context.

D. Expression Vectors

In order to express a GST-π polypeptide or antisense construct, it is necessary to provide an GST-π nucleic acid in an expression cassette. The expression cassette contains a GST-π nucleic acid under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. Those promoters most commonly used in prokaryotic recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1980; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (EPO Appl. Publ. No. 0036776).

The appropriate expression cassette can be inserted into a commercially available expression vector by standard subcloning techniques. Throughout this application, the terms "expression construct" or "expression vector" are meant to include any type of genetic construct containing a nucleic acid encoding an antisense product in which part or all of the nucleic acid sequence is capable of being transcribed. For example, the E. coli vectors pUC or pBluescript™ may be used according to the present invention to produce recombinant GST-π polypeptide in vitro. The manipulation of these vectors is well known in the art. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species (Bolivar et al., 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as a transforming vector in connection with these hosts. For example, the phage lambda GEM™-11 may be utilized in making recombinant phage vector which can be used to transform host cells, such as E. coli LE392.

In one embodiment, the protein is expressed as a fusion protein with β-gal, allowing rapid affinity purification of the protein. Examples of such fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.). Some of these fusion systems produce recombinant protein bearing only a small number of additional amino acids, which are unlikely to affect the functional capacity of the recombinant protein. For example, both the FLAG system and the 6×His system add only short sequences, both of which are known to be poorly antigenic and which do not adversely affect folding of the protein to its native conformation. Other fusion systems produce proteins where it is desirable to excise the fusion partner from the desired protein. In another embodiment, the fusion partner is linked to the recombinant protein by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

E. coli is a preferred prokaryotic host. For example, E. coli strain RR1 is particularly useful. Other microbial strains which may be used include E. coli strains such as E. coli LE392, E. coli B, and E. coli X 1776 (ATCC No. 31537). The aforementioned strains, as well as E. coli W3 110 (F-, lambda-, prototrophic, ATCC No. 273325), bacilli such as Bacillus subtilis, or other enterobacteriaceae such as Salmonella typhimurium or Serratia marcescens, and various Pseudomonas species may be used. These examples are, of course, intended to be illustrative rather than limiting. Recombinant bacterial cells, for example E. coli, are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents such as β-mercaptoethanol or DTT (dithiothreitol).

Under some circumstances, it may be advantageous to incubate the polypeptide for several hours under conditions suitable for the protein to undergo a refolding process into a conformation which more closely resembles that of the native protein. Such conditions generally include low protein concentrations less than 500 µg/ml, low levels of reducing agent, concentrations of urea less than 2M and often the presence of reagents such as a mixture of reduced and oxidized glutathione which facilitate the interchange of disulphide bonds within the protein molecule.

The refolding process can be monitored, for example, by SDS-PAGE or with antibodies which are specific for the native molecule (which can be obtained from animals vaccinated with the native molecule isolated from parasites). Following refolding, the protein can then be purified further and separated from the refolding mixture by chromatography on any of several supports including ion exchange resins, gel permeation resins or on a variety of affinity columns.

In preferred another embodiment, the expression system used is one driven by the baculovirus polyhedron promoter. The gene encoding the protein can be manipulated by standard techniques in order to facilitate cloning into the baculovirus vector. A preferred baculovirus vector is the pBlueBac vector (Invitrogen, Sorrento, Calif.). The vector carrying the α4 gene is transfected into *Spodoptera frugiperda* (Sf9) cells by standard protocols, and the cells are cultured and processed to produce the recombinant protein.

There are a variety of other eukaryotic vectors that provide a suitable vehicle in which recombinant GST-π can be produced. In various embodiments of the invention, the expression construct may comprise a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986) and adeno-associated viruses. Retroviruses also are attractive gene transfer vehicles (Nicolas and Rubenstein, 1988; Temin, 1986) as are vaccina virus (Ridgeway, 1988) adeno-associated virus (Ridgeway, 1988) and HSV (Glorioso et al., 1995). Such vectors may be used to (i) transform cell lines in vitro for the purpose of expressing proteins of interest or (ii) to transform cells in vitro or in vivo to provide therapeutic polypeptides in a gene therapy scenario.

With respect to eukaryotic vectors, the term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Preferred promoters include those derived from HSV, including the α4 promoter. Another preferred embodiment is the tetracycline controlled promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. Tables 2 and 3 list several elements/promoters which may be employed, in the context of the present invention, to regulate the expression of a transgene. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Host cells include eukaryotic microbes, such as yeast cultures may also be used. *Saccharomyces cerevisiae*, or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to eukaryotic microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (*Tissue Culture*, 1973). Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

E. Non-Viral Delivery Systems

In addition to the use of the viral expression vectors described above, expression vectors containing genes encoding GST-π's of the present invention may be delivered to cells using a variety of other methods. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), polycations (Boussif et al., 1995) and receptor-mediated transfection (Wu and Wu, 1987; Wu and Wu, 1988). Some of these techniques may be successfully adapted for in vivo or ex vivo use.

In one embodiment of the invention, expression vector (viral or non-viral) may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding an GSTπ construct may also be transferred in a similar manner in vivo.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ. DNA encoding a GST-π construct may be delivered via this method.

In a preferred embodiment of the invention, the antisense oligo- or polynucleotides and expression vectors may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-nucleic acid complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacterial promoter is employed in the DNA construct, it also will be desirable to include within the liposome an appropriate bacterial polymerase.

"Liposome" is a generic term encompassing a variety of single and multilamellar lipid vehicles formed by the generation of enclosed lipid bilayers. Phospholipids are used for preparing the liposomes according to the present invention and can carry a net positive charge, a net negative charge or are neutral. Dicetyl phosphate can be employed to confer a negative charge on the liposomes, and stearylamine can be used to confer a positive charge on the liposomes.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Other lipids for liposomal transfection, include but are not limited to phosphatidylcholine (PC), phosphatidylserine (PS), cholesterol (Chol), N-[1-(2,3-dioleyloxy)propyl]-N,N-trimethylammonium chloride (DOTMA), dioleoylphosphatidylethanolamine (DOPE), and/or 3β[N-(N'N'-dimethylaminoethane)-carbarmoyl cholesterol (DC-Chol), as well as other lipids known to those of skill in the art. Those of skill in the art will recognize that there are a variety of liposomal transfection techniques which will be useful in the present invention. Among these techniques are those described in Nicolau et al., 1987, Nabel et al., 1990, and Gao et al., 1991. Stock solutions of lipids in chloroform or chloroform/methanol can be stored at about −20° C. Preferably, chloroform is used as the only solvent since it is more readily evaporated than methanol.

Phospholipids from natural sources, such as egg or soybean phosphatidylcholine, brain phosphatidic acid, brain or plant phosphatidylinositol, heart cardiolipin and plant or bacterial phosphatidylethanolamine are preferably not used as the primary phosphatide, i.e., constituting 50% or more of the total phosphatide composition, because of the instability and leakiness of the resulting liposomes.

Liposomes used according to the present invention can be made by different methods. The size of the liposomes varies depending on the method of synthesis. A liposome suspended in an aqueous solution is generally in the shape of a spherical vesicle, having one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present both within and without the liposome, the lipid molecules will form a bilayer, known as a lamella, of the arrangement XY-YX.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

Dried lipids can be hydrated at approximately 25–50 mM phospholipid in sterile, pyrogen-free water by shaking until all the lipid film is resuspended. The aqueous liposomes can be then separated into aliquots, each placed in a vial, lyophilized and sealed under vacuum.

In the alternative, liposomes can be prepared in accordance with other known laboratory procedures: the method of Bangham et al. (1965), the contents of which are incorporated herein by reference; the method of Gregoriadis, as described in DRUG CARRIERS IN BIOLOGY AND MEDICINE, G. Gregoriadis ed. (1979) pp. 287–341, the contents of which are incorporated herein by reference; the method of the contents of which are incorporated by reference; and the reverse-phase evaporation method. The aforementioned methods differ in their respective abilities to entrap aqueous material and their respective aqueous space-to-lipid ratios.

The dried lipids or lyophilized liposomes prepared as described above may be dehydrated and reconstituted in a solution of inhibitory peptide and diluted to an appropriate concentration with an suitable solvent, e.g., DPBS. The mixture is then vigorously shaken in a vortex mixer. Unencapsulated nucleic acid is removed by centrifugation at 29,000×g and the liposomal pellets washed. The washed liposomes are resuspended at an appropriate total phospholipid concentration, e.g., about 50–200 mM. The amount of nucleic acid encapsulated can be determined in accordance with standard methods. After determination of the amount of nucleic acid encapsulated in the liposome preparation, the liposomes may be diluted to appropriate concentrations and stored at 4° C. until use.

In a preferred embodiment, the lipid dioleoylphosphatidylchoine is employed. Nuclease-resistant oligonucleotides were mixed with lipids in the presence of excess t-butanol. The mixture was vortexed before being frozen in an acetone/dry ice bath. The frozen mixture was lyophilized and hydrated with Hepes-buffered saline (1 mM Hepes, 10 mM NaCl, pH 7.5) overnight, and then the liposomes were sonicated in a bath type sonicator for 10 to 15 min. The size of the liposomal-oligonucleotides typically ranged between 200–300 nm in diameter as determined by the submicron particle sizer autodilute model 370 (Nicomp, Santa Barbara, Calif.).

Liposomes may be introduced into contact with cells to be transfected by a variety of methods. In cell culture, the liposomes can simply be dispersed in the cell culture solution. For application in vivo, liposomes are typically injected. Intravenous injection allow liposome-mediated transfer of DNA complex to the liposomes to, for example, the liver and the spleen. In order to allow transfection of DNA into cells which are not accessible through intravenous injection, it is possible to directly inject the liposome-DNA complexes into a specific location in an animal's body. For example, Nabel et al. teach injection via a catheter into the arterial wall. In another example, the inventors have used intraperitoneal injection to allow for gene transfer into mice.

The present invention also contemplates compositions comprising a liposomal complex. This liposomal complex will comprise a lipid component and a DNA segment encoding a GST-π gene or an antisense construct thereof. The gene employed in the liposomal complex can be, for example, GSTP1*B, GSTP1*C or any variant thereof. Liposomal complexes comprising antisense constructs may have distinct advantages as described herein. It is proposed that one may employ any gene product outlined herein in liposomal delivery, or alternatively two or more gene products together may be used in the practice of the invention.

It is proposed that it will ultimately be preferable to employ the smallest region needed to elicit the necessary therapeutic effect so that one is not introducing unnecessary DNA into cells which receive a GST-π gene construct. Techniques well known to those of skill in the art, such as the use of restriction enzymes, will allow for the generation of small regions of GST-π for such purposes. The ability of these regions to inhibit tumors can easily be determined by the assays reported in the Examples.

Another mechanism for transferring expression vectors into cells is receptor-mediated delivery. This approach takes advantage of the selective uptake of macromolecules by receptor-mediated endocytosis in almost all eukaryotic cells. Because of the cell type-specific distribution of various receptors, the delivery can be highly specific (Wu and Wu, 1993). Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1993). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that an adenoviral expression vector also may be specifically delivered into a cell type such as lung, epithelial or tumor cells, by any number of receptor-ligand systems, with or without liposomes. For example, epidermal growth factor (EGF) may be used as the receptor for mediated delivery of GST-π construct in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a polynucleotide into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods. During ex vivo culture, the expression vector can express the GST-π construct. Finally, the cells may be reintroduced into the original animal, or administered into a distinct animal, in a pharmaceutically acceptable form by any of the means described below.

F. Antibodies

Antibodies to GST-π peptides or polypeptides may be readily prepared through use of well-known techniques, such as those exemplified in U.S. Pat. No. 4,196,265. Typically, this technique involves immunizing a suitable animal with a selected immunogen composition, e.g., purified or partially purified protein, synthetic protein or fragments thereof, as discussed in the section on polypeptides. Animals to be immunized are mammals such as cats, dogs and horses, although there is no limitation other than that the subject be capable of mounting an immune response of some kind. The immunizing composition is administered in a manner effective to stimulate antibody producing cells. Rodents such as mice and rats are preferred animals, however, the use of rabbit, sheep or frog cells is possible. The use of rats may provide certain advantages, but mice are preferred, with the BALB/c mouse being most preferred as the most routinely used animal and one that generally gives a higher percentage of stable fusions.

For generation of monoclonal antibodies (MAbs), following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer removed. Spleen lymphocytes are obtained by homogenizing the spleen with a syringe. Typically, a spleen from an immunized mouse contains approximately $5 \times 10^7$ to $2 \times 10^8$ lymphocytes.

The antibody-producing B cells from the immunized animal are then fused with cells of an immortal myeloma cell line, generally one of the same species as the animal that was immunized. Myeloma cell lines suited for use in hybridoma-producing fusion procedures preferably are non-antibody-producing, have high fusion efficiency and enzyme deficiencies that render them incapable of growing in certain selective media which support the growth of only the desired fused cells, called "hybridomas."

Any one of a number of myeloma cells may be used and these are known to those of skill in the art. For example, where the immunized animal is a mouse, one may use P3-X63/Ag8, X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell line is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler & Milstein (1975; 1976), and those using polyethylene glycol (PEG), such as 37% (v/v) PEG, by Gefter et al. (1977). The use of electrically induced fusion methods is also appropriate.

Fusion procedures usually produce viable hybrids at low frequencies, from about $1 \times 10^{-6}$ to $1 \times 10^{-8}$. This does not pose a problem, however, as the viable, fused hybrids are differentiated from the parental, unfused cells (particularly the unfused myeloma cells that would normally continue to divide indefinitely) by culture in a selective medium. The selective medium generally is one that contains an agent that blocks the de novo synthesis of nucleotides in the tissue culture media. Exemplary and preferred agents are aminopterin, methotrexate and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide MAbs. The cell lines may be exploited for MAb production in two basic ways. A sample of the hybridoma can be injected, usually in the peritoneal cavity, into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Monoclonal antibodies of the present invention also include anti-idiotypic antibodies produced by methods well-known in the art. Monoclonal antibodies according to the present invention also may be monoclonal heteroconjugates, i.e., hybrids of two or more antibody molecules. In another embodiment, monoclonal antibodies according to the invention are chimeric monoclonal antibodies. In one approach, the chimeric monoclonal antibody is engineered by cloning recombinant DNA containing the promoter, leader, and variable-region sequences from a mouse antibody producing cell and the constant-region exons from a human antibody gene. The antibody encoded by such a recombinant gene is a mouse-human chimera. Its antibody specificity is determined by the variable region derived from mouse sequences. Its isotype, which is determined by the constant region, is derived from human DNA.

In another embodiment, monoclonal antibodies according to the present invention is a "humanized" monoclonal antibody, produced by techniques well-known in the art. That is, mouse complementary determining regions ("CDRs") are transferred from heavy and light V-chains of the mouse Ig into a human V-domain, followed by the replacement of some human residues in the framework regions of their murine counterparts. "Humanized" monoclonal antibodies in accordance with this invention are especially suitable for use in in vivo diagnostic and therapeutic methods for treating Moroxella infections.

As stated above, the monoclonal antibodies and fragments thereof according to this invention can be multiplied according to in vitro and in vivo methods well-known in the art. Multiplication in vitro is carried out in suitable culture media such as Dulbecco's modified Eagle medium or RPMI 1640 medium, optionally replenished by a mammalian serum such as fetal calf serum or trace elements and growth-sustaining supplements, e.g., feeder cells, such as normal mouse peritoneal exudate cells, spleen cells, bone marrow macrophages or the like. In vitro production provides relatively pure antibody preparations and allows scale-up to give large amounts of the desired antibodies. Techniques for large scale hybridoma cultivation under tissue culture conditions are known in the art and include homogenous suspension culture, e.g., in an airlift reactor or in a continuous stirrer reactor or immobilized or entrapped cell culture.

Large amounts of the monoclonal antibody of the present invention also may be obtained by multiplying hybridoma cells in vivo. Cell clones are injected into mammals which are histocompatible with the parent cells, e.g., syngeneic mice, to cause growth of antibody-producing tumors. Optionally, the animals are primed with a hydrocarbon, especially oils such as Pristane (tetramethylpentadecane) prior to injection.

In accordance with the present invention, fragments of the monoclonal antibody of the invention can be obtained from monoclonal antibodies produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer, or they may be produced manually using techniques well known in the art.

The monoclonal conjugates of the present invention are prepared by methods known in he art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents, or by reaction with an isothiocyanate. Conjugates with metal chelates are similarly produced. Other moieties to which antibodies may be conjugated include radionuclides such as $^{3}H$, $^{125}I$, $^{131}I$ $^{32}P$, $^{35}S$, $^{14}C$, $^{51}Cr$, $^{36}Cl$, $^{57}Co$, $^{58}Co$, $^{59}Fe$, $^{75}Se$, $^{152}Eu$, and $^{99}mTc$, are other useful labels which can be conjugated to antibodies. Radioactively labeled monoclonal antibodies of the present invention are produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium- $^{99}$m by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as $SNCl_2$, a buffer solution such as sodium-potassium phthalate solution, and the antibody.

G. Diagnostic Applications

The present invention provides for the diagnosis of cancers by virtue of determining the presence of particular forms of GST-π. This can be done by examining the cellular phenotype at the nucleic acid level or at the protein level. At the nucleic acid level, several different formats are contemplated. First, one may perform a restriction fragment analysis of the gene of interest. This may be accomplished by isolating the gene and performing a restriction digest thereof. Alternatively, this can be accomplished by digesting genomic DNA and probing the cleaved DNA with an appropriate labeled probe. In either case, the probing experiments, called Southern blots, rely on the ability of a labeled nucleic acid, complementary to the target sequence, to hybridize thereto. Based on differences in restriction patterns, different sized nucleic acids will be produced. Generally, size fractionation is performed by electrophoresis, prior to probing. The nucleic acids are transferred or "blotted" on to a suitable support (.e.g., nitrocellulose), which is then probed with the labeled nucleic acid.

Second, one may perform a nucleic acid sequence analysis. Again, one may first clone the gene of interest but, more typically, one will sequence the genomic DNA prior to cloning, often employing a PCR approach with labeled primers. The primers are located upstream of the sequence of interest and are extended by a polymerase, e.g., Sequenase™. Using a series of naturation-denaturation steps, amplification of templates is achieved. Use of dideoxy nucleotides permits implementation of the Sanger dideoxy-chain termination sequencing protocol.

At the protein level, the examination will performed from an immunologic standpoint, employing GST-π-specific antibodies as described above. Thus, it is proposed that the monoclonal antibodies of the present invention will find useful diagnostic application in standard immunochemical procedures, such as ELISA and western blot methods, as well as other procedures which may utilize antibodies specific to GST-π epitopes. While ELISAs are preferred forms of immunoassays, it will be readily appreciated that assays also include RIAs and other non-enzyme linked antibody binding assays or procedures. Additionally, it is proposed that monoclonal antibodies specific to the particular GST-π epitope may be utilized in other useful applications. For example, their use in immunoabsorbent protocols may be useful in purifying native or recombinant GST-π species or variants thereof.

It also is proposed that the disclosed GST-π peptides and polypeptides will find use as antigens for raising antibodies and in immunoassays for the detection of anti-GST-π antigen-reactive antibodies and GST-π antigens (competitive assays). Alternatively, immunoassays may be exploited to determine the structural-antigenic relationship between certain GST-π mutant peptides. Such screening assays may involve (i) the generation of antisera or antibodies against peptides or (ii) the testing of mutant peptide reactivity with a battery of immunoreagents developed against GST-π antigens. In this way, a mutational analysis of various epitopes may be performed.

Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and radioimmunoassays (RIAs) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the anti-GST-π antibodies of the invention are immobilized onto a selected surface exhibiting protein affinity, such as a well in a polystyrene microtiter plate. Then, a test composition suspected of containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is a simple "sandwich ELISA." Detection also may be achieved by the addition of a second antibody specific for the desired antigen, followed by the addition of a third antibody that has binding affinity for the second antibody, with the third antibody being linked to a detectable label.

In another exemplary ELISA, the samples are immobilized onto the well surface and then contacted with the anti-GST-π antibodies. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs are also possible in which test samples compete for binding with known amounts of labeled antigens or antibodies. The amount of reactive species in the unknown sample is determined by mixing the sample with the known labeled species before or during incubation with coated wells. Peptide antigen or antibodies may also be linked to a solid support, such as in the form of beads, dipstick, membrane or column matrix, and the sample to be analyzed applied to the immobilized peptide or antibody. The presence of reactive species in the sample acts to reduce the amount of labeled species available for binding to the well, and thus reduces the ultimate signal.

Irrespective of the format employed, ELISAs have certain features in common, such as coating, incubating or binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

After binding of material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera is then allowed to incubate for from 2 to 4 hours, at temperatures preferably on the order of 25° to 27° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen or antibody, followed by subsequent washing, the occurrence and even amount of immunocomplex formation may be determined by subjecting same to a second antibody having specificity for the first or for a distinct epitope of the bound antigen. Of course, in a test sample suspected of containing antibodies of human origin, the second antibody will preferably be an antibody having specificity in general for human IgG. To provide a detecting means, the detecting antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween).

After incubation with the enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer. Alternatively, the label may be a chemiluminescent one. The use of such labels is described in U.S. Pat. Nos. 5,310,687, 5,238,808 and 5,221,605.

In competitive formats, one may use labeled or unlabeled peptide as a competitor for the antigen in a sample. Alternatively, competing antibodies will require that the binding of two different antibodies be distinguishable. This can be accomplished by labeling species and not the other, or by labeling both species with differential labels (e.g., rhodamine and fluorescein).

H. Small Molecule Inhibitors of GST-π Variant Proteins

The present invention provides methods for screening and identifying small molecule inhibitors of GST-π proteins and identifies such inhibitors (see Tables 14–17). The rationale behind the design of the small molecule GST-π protein inhibitors is that the structural differences between GST-π proteins, caused by the deviations in the interatomic distances of the amino acid residues in the active site of the protein, will be exploited to design chemical ligands that bind to the active site of the different variant proteins to yield complexes with sufficient thermodynamic stability to effectively inhibit the functional activity of the protein. The inhibited GST-π protein is thus unable to protect the tumor cell against the toxic action of the anticancer agent used to treat it. To obtain appropriate ligands that bind to the active sites of different GST-π variant proteins, the inventors utilize the technique of forcefield docking of chemical fragments from both commercially available chemical fragment libraries, as well as in-house generated libraries, into the active electrophile-binding (H-) site in the derived crystal structure of each variant protein. The docked fragments will be energy-minized and the binding energies computed and used to select candidate ligands.

Generation of GST-π inhibitors. Generation of inhibitors is accomplished by a rational drug development strategy involving force field docking and energy-minimization of chemical fragments and compounds into the active site of the variant GST-π proteins. The compounds and chemical fragments can be drawn from chemical fragment libraries, such as that available in the Leapfrog database. Additional chemical libraries will be generated as necessary. The active site and other structural components of the variant GST-π proteins will be derived from the published crystal structure of the GSTP1*A encoded protein. The protein encoded by GSTP1*B are obtained by substituting valine for isoleucine at amino acid 104; the protein encoded by GSTP1*C by substituting valine for isoleucine at amino acid 104, and valine for alanine at amino acid 113. Based on the resultant ΔΔH values obtained after energy minimization of chemical fragments/compounds, candidate inhibitors are selected and/ or newly constructed from chemical fragments for synthesis and further analyses for their inhibitory or other action on the variant GST-π proteins. Selection criteria for inhibitors for synthesis and further analysis includes lipophilicity, chemical stability and availability or ease of synthesis.

Candidate inhibitors of the present invention include such molecules as substituted isoxazole for example the molecules shown in Table 14; heterocyclic aromatic compounds, (Table 15); sugar-linked aromatic compounds (Table 16) and other aromatic compounds (Table 17). The substituted isoxazole compounds may have a generic structure such as that given below:

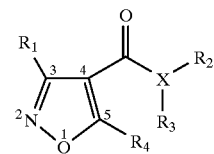

General Structure (Substituted Isoxazoles)

The substituted groups may vary between the different compounds and result in significant changes in binding energies of the compounds in the active site pocket of the GST-π protein. For example, $R_1$ substitutions of either $NH_2$ or OH, cause changes in binding energies of almost 10 kcals/mol. Other important substitutions are the alkyl or aminoalkyl substitutions of $R_3$, and the alkyl, phenyl or 2-pyridyl substitutions of $R_4$, some of which result in changes in binding energies of greater than 10 kcals/mol.

However it is conceivable that any of the R groups of the substituted isoxazoles may be a phenyl group, a benzyl group, an aryl group, an alkyl group, an aryl group linked to another aryl group through an ester linkage, an aryl group linked to an alkyl group with an ester linkage, an aryl group linked to another aryl group through an ether linkage and aryl group linked to an alkyl group with a thiolester linkage, an alkyl group linked to another alkyl group through an ester linkage, an alkyl group linked to another alkyl group through an ether linkage, an alkyl to alkyl linked through an amino group, an aryl to alkyl linked through an amino group. an alkyl alkyl group through a disulphide group, an aryl linked to an alkyl group through a disulphide group, an aryl linked to another aryl group through a disulphide group, an alkyl linked to another alkyl group through a thioester linkage, an aryl linked to an alkyl group through a polyester linkage, an aryl group linked to another aryl through a polyester linkage, an alkyl group linked to another alkyl group through a polyamine linkage, an aryl linked to an alkyl group through a polyamine linkage, an aryl group linked to another aryl through a polyamine linkage, an alkyl group linked to another alkyl group through a polythioester linkage, an aryl linked to an alkyl group through a polythioester linkage, an aryl group linked to another aryl through a polythioester linkage.

An individual skilled in the art of organic synthesis in light of the present disclosure is able to prepare or identify a large variety of substituted isoxazoles which would be expected to have GST-π inhibitory effects in the light of the present disclosure and may be used in the for inhibiting tumors and/or other diseases GST-π proteins play a prominent role.

Screening for modulators of GST-π. Within certain embodiments of the invention, methods are provided for screening for modulators of GST-π protein activity. Such methods may use labeled GST-π proteins or analogs, anti-GST-π proteins or anti-GST-π antibodies and the like as reagents to screen small molecule and peptide libraries to identify modulators of GST-π protein activity. Within one example, a modulator screening assay is performed in which cells expressing GST-π proteins are exposed to a test substance under suitable conditions and for a time sufficient to permit the agent to effect activity of GST-π proteins. The GST-π activity is then detected by incubating the reaction mixture with a GST-π protein-specific antibody, which antibody may be labeled directly or may be detected secondarily, e.g. using a labeled idiotypic or species specific antibody) under conditions that permit the formation of immune complexes between GST-π protein and its specific antibody. The test reaction is compared to a control reaction which lacks the test sample. To complete the modulator screening assay, the presence and/or amount of complexes formed between GST-π protein and the anti-GST-π antibody is detected in the test sample (e.g. by determining the presence or amount of label bound directly to the antibody or to a secondary antibody directed against the primary antibody). Within this exemplary assay, agents that inhibit activity of GST-π protein will demonstrate a reduced binding with GST-π protein-specific antibodies relative to the control sample and agents that induce activity of GST-π protein will demonstrate an increased binding with GST-π protein specific antibodies relative to the control sample.

Generally the test substance is added in the form of a purified agent, however it is also contemplated that test substances useful within the invention may include substances present throughout the handling of test sample components, for example host cell factors that are present in a cell lysate used for generating the test sample. Such endogenous factors may be segregated between the test and control samples for example by using different cell types for preparing lysates, where the cell type used for preparing the test sample expresses a putative test substance that is not expressed by the cell type used in preparing the control sample.

Useful compounds in this regard will not be limited to those mentioned in Tables 14–17. The active compounds may include fragments or parts of naturally-occurring compounds or may be only found as active combinations of known compounds which are otherwise inactive. However, prior to testing of such compounds in humans or animal models, it may be necessary to test a variety of candidates to determine which have potential.

Accordingly, in screening assays to identify agents which alter the activity of GST-π proteins in for example cancer cells, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

In these embodiments, the present invention is directed to a method for determining the ability of a candidate substance to decrease the GST-π activity of cancer cells, the method including generally the steps of:

(a) obtaining a cell with GST-π activity;

(b) admixing a candidate substance with the cell; and (c) determining the ability of the candidate substance to inhibit the GST-π activity of the cell.

To identify a candidate substance as being capable of decreasing GST-π activity, one would measure or determine the basal GST-π status of for example a cancer cell prior to any additions or manipulation. One would then add the candidate substance to the cell and redetermine the GST-π activity in the presence of the candidate substance. A candidate substance which decreases the GST-π activity relative to the composition in its absence is indicative of a candidate substance being an inhibitor of GST-π

The candidate screening assay is quite simple to set up and perform, and is related in many ways to the assay discussed above for determining GST-π content.

"Effective amounts", in certain circumstances, are those amounts effective at reproducibly decrease GST-π activity in an assay in comparison to their normal levels. Compounds that achieve significant appropriate changes in activity will be used. If desired, a battery of compounds may be screened in vitro to identify other agents for use in the present invention.

A significant decreases in GST-π activity, are represented by a decrease in GST-π protein activity levels of at least about 30%–40%, and most preferably, by decreases of at least about 50%, with higher values of course being possible. Assays that measure GST-π activity in cells are well known in the art and may be conducted in vitro or in vivo, and have been described elsewhere in the specification.

Alternatively, it may be desirable simply to measure inhibition of growth of cancer cells, for example, by measuring growth according to the MTT assay. A significant inhibition in growth is represented by decreases of at least about 30%–40% as compared to uninhibited, and most preferably, of at least about 50%, with more significant decreases also being possible. Growth assays as measured by the MTT assay are well known in the art. Assays may be conducted as described by Mosmann et al., 1983; Rubinstein et al., 1990 (incorporated herein by reference). Therefore, if a candidate substance exhibited inhibition of growth of cancer cells in this type of study, it would likely be a suitable compound for use in the present invention.

Quantitative in vitro testing of the GST-π inhibitors is not a requirement of the invention as it is generally envisioned that the agents will often be selected on the basis of their known properties or by structural and/or functional comparison to those agents already demonstrated to be effective. Therefore, the effective amounts will often be those amounts proposed to be safe for administration to animals in another context.

I. Therapeutic Methods

In the practice of the invention described in this application, several aspects are unique. For therapy, the invention will be used to modulate the response of the tumor to subsequent therapy. This approach will be to administer the small molecule inhibitor and/or antisense oligonucleotide or ribozyme, based on the GST-π variant present in the tumor and/or patient's cells. This treatment will reduce the tumors' ability to block the toxic action of any subsequent therapy. The initial treatment with the AS-ON or ribozyme will be followed some time later with the anticancer agent. Anticancer agents will include but not be limited to alkylating agents and cisplatin and other platinum analogs. Tumors against which this modulation will be used will include those tumors that have been shown to be associated with altered GST-π levels, including melanoma, leukemias and lymphomas, melanoma, as well as tumors of the brain, head and neck, stomach, liver, lung, ovary, breast, colon and bladder. Additionally in those tumors with elevated GST-π, the small molecule inhibitor and/or antisense oligonucleotide or ribozymes will be given with the goal of decreasing the malignant phenotype, reducing or inhibiting the growth, or killing the tumors. It is expected that the latter will involve longer term administration of these agents alone or in combination with other therapeutic agents.

A wide variety of chemotherapeutic agents may be used in combination with the therapeutic genes of the present invention. These can be, for example, agents that directly cross-link DNA, agents that intercalate into DNA, and agents that lead to chromosomal and mitotic aberrations by affecting nucleic acid synthesis.

Agents that directly cross-link nucleic acids, specifically DNA, are envisaged and are shown herein, to eventuate DNA damage leading to a synergistic antineoplastic combination. Agents such as cisplatin, and other DNA alkylating agents may be used.

Agents that damage DNA also include compounds that interfere with DNA replication, mitosis, and chromosomal segregation. Examples of these compounds include adriamycin (also known as doxorubicin), VP-16 (also known as etoposide), verapamil, podophyllotoxin, and the like. Widely used in clinical setting for the treatment of neoplasms these compounds are administered through bolus injections intravenously at doses ranging from 25–75 mg/m$^2$ at 21 day intervals for adriamycin, to 35–100 mg/m$^2$ for etoposide intravenously or orally.

It is contemplated that antibiotics such as Doxorubicin, Daunorubicin Mitomycin Actinomycin D Bleomycin Plant Alkaloids such as Taxol, Vincristine Vinblastine, Alkylating Agents such as Carmustine, Melphalan , Chlorambucil, Busulfan, Lomustine and miscellaneous agents such as Cisplatin, VP16 (etoposide), and Tumor Necrosis Factor will be useful in conjunction with the present invention. These are examples of some routinely used chemotherapeutic agents, these are only exemplary agents and the list is by no means exhaustive and the skilled artisan is referred to "Remington's Pharmaceutical Sciences" 15th Edition, chapter 61 regarding further information about these and other chemotherapeutic agents. The person responsible for administration of chemotherapeutic agent will, determine the appropriate doses for the individual subject.

In certain aspects the present invention provides antisense and other genetic constructs for delivery into tumor cells. The compositions of the present invention may thus be applied advantageously in the treatment of a cancer cell. The compositions may comprise a liposome in which a polynucleotide is encapsulated. Such a composition may advantageously be delivered to a subject in a volume of 0.50–10.0 ml per dose. It is envisioned that the dose of gene construct may be delivered in an amount of between about 5 to about 30 mg polynucleotide per m$^2$. Alternatively the dose may be between about 6 and 25 mg polynucleotide per m$^2$, between about 7 and about 20 mg polynucleotide per m$^2$, between about 10 to about 15 mg polynucleotide per m$^2$.

J. Pharmaceutical Compositions and Routes of Administration

The present invention provides pharmaceutical compositions for the generation of antibodies against GST-π and the prevention or treatment of cancers in which a GST-π is involved. Administration of antigens and generation of antibodies is discussed above. Administration of nucleic acids, including expression constructs, to cells in vivo may be adapted from currently available information. Those of skill in the art are well-versed in the treatment of tumors generally and, given the information provided here, the present invention may be exploited using various specific pharmaceuticals, doses and routes of administration for therapies.

Aqueous compositions of the present invention will have an effective amount of an antigen or therapeutic agent. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as analgesics and anti-inflammatory agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention may be formulated for parenteral administration, e.g., formulated for injection via the intravenous, intramuscular, subcutaneous, or even intraperitoneal routes. The preparation of an aqueous composition that contains active compounds of the present invention ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. Direct intratumoral injection or continuous perfusion of the resected tumor bed is a method of administration envisioned by the present invention.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

K. Kits

All the essential materials and reagents required for practice of various embodiments of the present invention may be assembled together in a kit. When the components of the kit are provided in one or more liquid solutions, the liquid solution preferably is an aqueous solution, with a sterile aqueous solution being particularly preferred.

For in vivo use, an antigen or therapeutic agent, the reagents may be formulated into a single or separate pharmaceutically acceptable syringeable composition. In this case, the container means may itself be an inhalant, syringe, pipette, eye dropper, or other such like apparatus, from which the formulation may be applied to an infected area of the body, injected into an animal, or even applied to and mixed with the other components of the kit.

The components of these kits may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the active compound, or explaining the assays for determining sebum formation in samples.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle. Other instrumentation includes devices that permit the reading or monitoring of reactions in vitro.

L. Examples

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1
Cloning and Characterization of Three Human GST Genes
1. Materials and Methods Materials. Restriction endonucleases, Klenow enzyme and T4 DNA ligase were purchased from Boehringer Maniihein, Indianapolis, Ind. Proteinase K, RNAse A, and all-trans retinoic acid (RA) were purchased from Sigma Chemical Co., St. Louis, Mo. SuperCos I cosmid vector, Bluescript phagemid 11, Gigapack 11 packaging System, calf intestinal alkaline phosphatase (CIAP), pBK-CMV expression vector, and the MSB mammalian transfection kit were purchased from Strategene, La Jolla, Calif. [$^{35}$S]dATP and [($\alpha$-$^{32}$P]dCTP were purchased from Amersham, Arlington Heights, Ill. Taq DNA polymerase was purchased from Perkin Elmer Cetus, Norwalk, Conn. Dulbecco's modified Eagle's medium (DMEM) and fetal calf serum (FCS) were purchased from Life Technology, Gaithersberg, Md. T7 DNA Sequenase 2.0 Dideoxy DNA Sequencing Kit was purchased from US Biochemicals, Cleveland, Ohio.

Tumor Cells. The MGR-3 human glioblastoma multiforme cell line was established in the laboratory of the inventors from a primary specimen, as previously described (Ali-Osman, 1996). It is glial fibrillary acidic protein positive by immunocytochemistry, and the cells show the typical pleomorphic features of neoplastic glial cells. It is routinely maintained in DMEM supplemented with 10% FCS, nonessential amino acids, and had undergone 11 in vitro passages prior to being used in these studies.

Southern and Northern blotting. These were performed using standard techniques (Sambrook et al., 1989). For the Southern analysis, genomic DNA was extracted from MGR-3 cells using the phenol/chloroform procedure, and for the Northern blots, total RNA was isolated with the acid guanidinium thiocyanate/phenol/chloroform method (Chomcznski and Saachi, 1987).

PCR. Where indicated, PCR was performed in a DNA thermocycler (Perkin-Elmer, Norwalk, Conn.). The 100 $\mu$l reaction mixture contained 50 ng SuperCos-GSTpi or other DNA template, 500 ng each of forward and reverse primers, 10×PCR buffer, 100 nM each of dATP, dCTP, dGTP and dTTP, 2.5 units Amplitaq polymerase overlaid with mineral oil. After 1 cycle of denaturing (95° C. for 90 secs), annealing (55° C. for 2 mins), and chain extension (72° C. for min), 35 cycles of 95° C. (1 min), 55° C. (2 min), and 72° C. (3 min) were performed.

Construction of cosmid genomic DNA library, screening and mapping. High molecular weight genomic DNA from MGR-3 cells was partially digested with Sau3A I and the fragments were ligated into SuperCos I cosmid vector that had been digested with BamH I and XbaI and dephosphorylated with calf intestinal alkaline phosphatase (CIAP). The constructs were packaged into bacteriophage lambda particles using the Gigapack 11 packaging system, and the resulting phage was used to infect the bacterial host strain XL-I Blue MR, amplified and plated onto LB/ampicillin plates at 50,000 cfus per 150 mm plate for a total of approximately 1×10$^6$ colonies. Colonies were pooled, titered, and the stock was stored at −80° C. in LB broth containing 20% glycerol. Aliquots were replated, lifted onto positively charged nylon filters and screened by hybridization with a [($\alpha$-$^{32}$P] labeled full-length GST-$\pi$ cDNA probe, using standard techniques (Sambrook et al., 1989). Following secondary and tertiary screenings, one positive clone, designated SuperCosGSTpi, was selected for further characterization. Restriction mapping of SuperCos-GSTpi was performed using standard methods and subsequently verified by computer analysis.

Subcloning of SuperCos-GSTpi. One-half $\mu$g of SuperCos-GSTpi DNA was digested with Not I and HinD III alone and in combination and electrophoresed in 1.2% agarose. GST-$\pi$ positive fragments, confirmed by Southern-blotting, were purified from the agarose gel, ligated into Not I and HinD III sites of the pBluescript 11 phagemid vector and transfected into competent XL-I Blue cells. After plating, GST-$\pi$-positive clones were identified by Southern hybridization and overlapping GST-$\pi$ gene fragments were amplified by PCR from the clones, using primers derived from published GST-$\pi$ sequences (Cowell et al., 1988; Morrow et al., 1989) and from the cosmid sequence (Table 1). The PCR products were electrophoresed in 1.2% agarose and fragments of appropriate sizes were excised, purified, blunt-ended with 0.05 unit/pmol DNA Klenow enzyme and ligated into EcoRV-digested and CIAP-treated pBluescript phagemid 11. Competent XL-I Blue cells were transfected with the vector constructs and GST-$\pi$ positive clones identified by Southern hybridization and used for sequencing.

DNA sequencing and structural analysis. Nucleotide sequencing was performed with the $^{35}$S-dideoxynucleotide chain termination method (Sanger et al., 1977), using T7 DNA Sequenase™, according to the manufacturer's protocols, with slight modifications. Each gene fragment was sequenced twice in both directions. Sequencing primers were designed from published GST-$\pi$ gene sequences and from the sequence of the cosmid. To ensure that sequences obtained from PCR products did not contain PCR artifacts, PCR and sequencing of each fragment was repeated at least once.

Computer-assisted analysis of the nucleotide sequence and structural organization of the isolated GST-$\pi$ gene were performed using a commercial DNA sequence analysis package (Macmolly Tetra, Berlin, Germany). The sequence was compared with those of the previously described GST-$\pi$ genes from the MCF-7 and the HPB-ALL cell lines (GenBank Accession Nos. X08058 and X0894-6, respectively). For further analysis of introns 5 and 6 of the isolated GST-$\pi$ gene, a 1 kB DNA fragment containing intron 5 and a 450 bp fragment containing intron 6, as well as the regions flanking these introns, were amplified using the primer pairs listed in Table 1. Following electrophoresis in 1.2% agarose gel, the PCR products were purified and digested with Spe I and Ava II to determine the presence of Spe I restriction sites in intron 5 and for Ava II sites in intron 6, both of which were predicted by the nucleotide sequence analysis to be present in these regions of the GST-$\pi$ gene. Because of previous data indicating that the GST-$\pi$ gene could be regulated by retinoic acid (Xia et al., 1993, 1996), we analyzed the cloned GST-$\pi$ gene for tile presence of sequences homologous with known retinoic acid response element (RARE) consensus sequences (Glass et al., 1991).

GST-$\pi$ vector construction and expression in COS-1 cells. The complete GST-$\pi$ gene was obtained by ligating a 2.2 kB Not I/BamH I pBS-GST-π fragment to a 0.9 kB BamH I/Kpn I pBS-GST-π fragment and subsequently ligating this into the Not I/Kpn I site of the PBK-CMV expression vector (Strategene, La Jolla, Calif.), in which eukaryotic expression is driven by the cytomegalovirus (CMV) immediate early promoter. The resulting GST-π expression construct, designated pGSTpi-CMV, contained the entire 3.1 kB GST-π gene, consisting of 131 bp of 5' promoter region, 109 bp of 3'-untranslated region including the polyadenylation signal, and 68 bp downstream of the polyadenylation signal.

pGSTpi-CMV vector was transfected into exponentially growing COS-1 cells using the calcium phosphate method (Sambrook et al., 1989) and, after 48 hrs, the cells were harvested, washed twice in PBS, homogenized and centrifuged at 20,000×g for 20 min at 4° C. Protein concentrations and total GST enzyme activity in the supernatants were determined as previously described (Ali-Osman et al., 1990; Habig et al., 1974), the latter using 1-chloro-2,4-dinitrobenzene as a substrate. Specific GST-π protein content was determined by Western blotting was performed, as we previously described (Ali-Osman et al., 1990).

DNA mobility shift assay forRA-RAR binding to RAREs in GST-π gene. The binding of the RARE sequences in the GST-π gene to RA-RAR complexes was examined using a gel mobility shift assay (Hupp et al., 1992) with nuclear extracts from MGR-3 cells treated with 1 μM all-trans RA for 48 hrs to induce retinoic acid receptor (RAR) expression, and to generate RA-RAR complexes. Immunoprecipitation with anti-RAR-β monoclonal antibodies (Santa Cruz, Santa Cruz, Calif.) showed a significant induction of RAR-β in the nuclear extracts of RA-treated MGR- cells used in the RARE binding studies. A 200 bp fragment was synthesized by DNA-PCR (for primers, see Table 2) from the isolated GST-π gene to cover the region in intron 5 containing the RARE consensus half-sites. 2.5 ug of nuclear proteins prepared from both control and RA-treated cells were incubated with $\gamma^{32}$P-dATP end-labeled RAREs in a buffer of 100 mM Tris-HCl (pH 7.4), 100 mM KCl, 5 mM $MgCl_2$, 10% glycerol, 1 mM DDT and 2 μg poly(dI-dC). After 30 mins at room temperature, the reaction mixture was electrophoresed in a 3% stacking and 10% separating non-denaturing polyacrylamide gel, after which the gel was fixed in 10% methanol/10% acetic acid, dried on Whatman filter paper and exposed to x-ray films. Binding competition experiments were performed by incubating the nuclear extracts with a 200 molar excess of unlabeled RAREs for 30 mins before addition of $^{32}$P-labeled RARES.

Retinoic acid effect on GST-π gene expression in tumor cells. To further determine the functionality of the RAREs in GST-π gene of MGR-3 cell line, we examined changes in GST-π gene transcripts in MGR-3 cells after exposure to RA. For this study, MGR-3 cells in exponential growth were treated with 1 μM all-trans RA. Another set cultures without RA treatment served as controls. After 24 and 48 hrs incubation at 37° C., total RNA was extracted and GST-π gene transcript levels were determined by Northern blotting, as described earlier. Alterations in GST-π protein content was determined in cells similarly treated with 1 μM all-trans RA. Cultures were harvested after 0, 12, 24 and 48 hrs post-RA exposure, cell extracts prepared from them, as previously described, and subjected to Western blotting with anti-GST-π antibodies.

2. Results

Construction and screening of a genomic library. Approximately $10^6$ colonies of the MGR-3 SuperCos I genomic library were initially screened with the GST-π cDNA probe. Twenty positive colonies were subjected to secondary screening after which two were selected for tertiary screening. One positive clone, designated SuperCos-GSTpi containing the intact GST-π gene was selected for further analysis.

Restriction endonuclease mapping of SuperCos-GSTpi. The results of Southern analysis of Not I and HinD III digested SuperCos-GSTpi with a GST-π cDNA probe were used to construct a simplified restriction map of the SuperCos-GSTpi clone (FIG. 1). The map shows the GST-π gene to be located between two Not I sites of the SuperCos-GSTpi clone, and to overlap two HinD III fragments. The entire gene is contained within a 2.1 kB Not I-HinD III fragment and an 11.5 kB HinD III fragment. This was subsequently verified by computer analysis of the final DNA sequence.

Nucleotide sequence and structural analysis. FIG. 2A shows the subclones of SuperCos-GSTpi used to sequence the complete GST-π gene, and FIG. 2B shows the sequencing strategy used. The nucleotide sequence of the isolated GST-π gene is shown as SEQ ID NO:1. The sequenced region is 3116 bp in size and contains the entire GST-π gene, consisting of 7 exons and 6 introns located within nucleotides +30 and +2762. Each of the exon-intron boundaries is characterized by the AG and GT splicing signals at the 5' and 3' ends, respectively. The coding region of the isolated GST-π gene consists of 211 codons including the ATG initiation and TGA termination codons. The 3' non-coding region of the gene covers nucleotides +2763 to +2984 and includes the polyadenylation signal, AATAAA, at +2818 to +2823. The 5'-flanking region upstream of the first exon of the gene, i.e., the promoter region, contains 5 regulatory motifs, all of which have been previously reported (Cowell et al., 1988; Morrow et al., 1989). Relative to the transcription initiation site (Morrow et al., 1989), these were, a TATA box located at −31 to −27, two Spl sites at −46 to −41 and −57 to −51, and an AP1 site at −69 to −63. Embedded in the AP1 site at −70 to −61 was an antioxidant response element (ARE) core consensus sequence, GTGACTCAGC (SEQ ID NO:33).

Comparison of isolated gene with previously described GST-π gene. Table 2 summarizes the structural differences between the GST-π gene isolated from the MGR-3 cell line and that of the previously reported GST-π gene from the MCF-7 cell line (Morrow et al,. 1989). Two transitions, an A-to-G at +1404 and a C-to-T at +2294 changed codon 105 from ATC (Ile) to GTC (Val) and codon 114 from GCG (Ala) to GTG (Val), respectively. These findings confirmed the isolated gene to be hGSTP1*C, the full-length cDNA which was recently isolated in the laboratory. A silent T-to-C nucleotide transition, present at nucleotide +2684, did not alter the amino acid, serine, encoded in the affected codon 185.

In addition to the three nucleotide transitions in exons 5, 6 and 7, several intronic differences were also observed between the MGR-3 and the MCF-7 GST-π genes. A region of high homology with the core sequence (CCCGCCTC) of the insulin response element-A, IRE-A (Nasrin et al., 1990) was observed at +45 to +52. This IRE differed from that previously described at the same location in the GST-π gene isolated from the MCF-7 (Morrow et al., 1989) by having a guanine insertion at +50, thus creating a cleavage site (CG'CG) for several restriction endonucleases, including Acc II, Aci I, Bsp 5OI, Bst UI and Mvn I. Additionally, nucleotide transitions in introns 5 and 6 created extra endonuclease cleavage sites in the MGR-3 GST-π gene, that are absent in the MCF-7 gene. A G-to-A transition at nucleotides +1968 created a Spe I site, A'CTAGT, in intron 5, which was confirmed by SpeI digestion of a 1 kB PCR product containing intron 5. Interestingly, only partial cleavage was observed upon SpeI digestion of the same DNA region from human lymphocytes and MCF-7 cells, indicating the existence of polymorphism of the GST-π gene at this position. Additionally, two transitions of A-to-G and C-to-T at +2557 and +2559, respectively, created within intron 6, new Ava II cleavage sites, G'GTCC, that are not present in the MCF-7 gene. Ava II digestion of a 450 bp DNA fragment amplified from MGR-3 cells to cover this region of intron 6 showed the expected 400 and 50 bp fragments. In contrast, the same DNA fragment from normal human lymphocytes and MCF-7 cells yielded these two Ava II cleavage products, and, in addition, uncleaved DNA in the case of MCF-7 and multiple restriction fragments in the case of lymphocytes.

Figure 3:
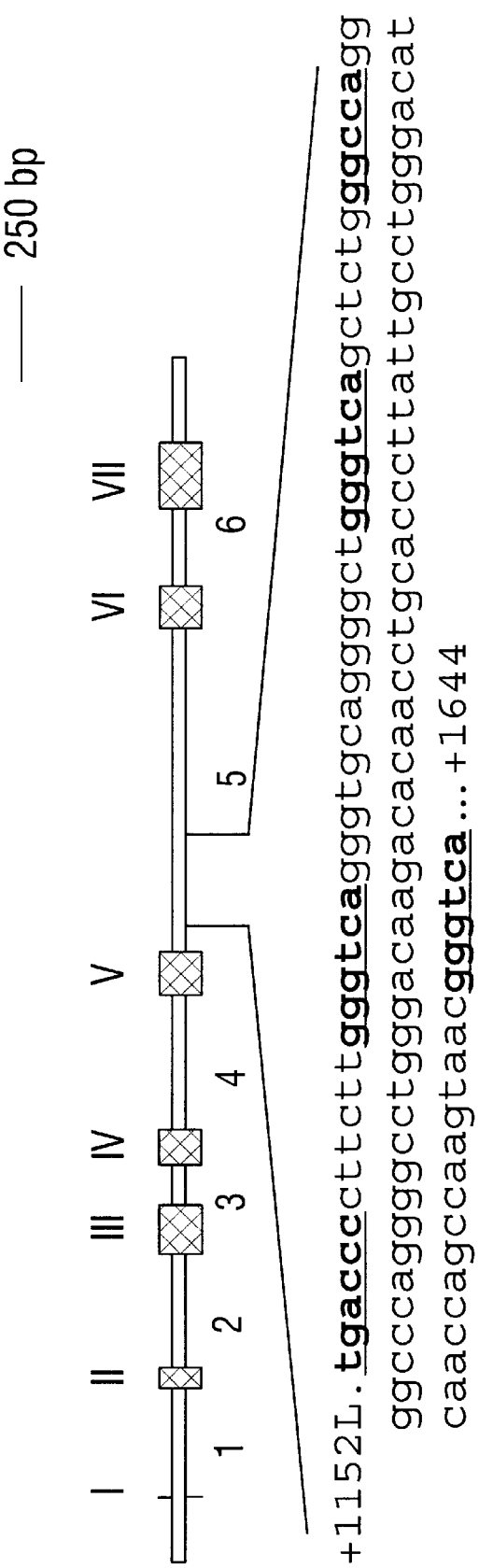
FIG. 3. Region of intron 5 of the GST-π gene showing one palindromic and four direct repeats of RARE consensus half-sites arranged in tandem between +1521 and +1644.

RAREs in isolated GST-π gene. Retinoic acid response elements, RARES, are direct repeat regulatory motifs to which RA-RA receptor (RAR) complexes bind and mediate transcription of RA-responsive genes (Glass et al., 1991; de The et al., 1990; Duester et al., 1991). We report, for the first time, the presence of RARE sequences in the GST-π gene. These RARE motifs are located in intron 5 of the GST-π gene, in a region spanning nucleotides +1521 to +1644 and consisted of one palindromic and four direct repeats of RARE consensus half-sites arranged in tandem. FIG. 3 shows region of the RARE half-sites. Table 3 compares the consensus RAREs in the isolated GST-π gene with known RAREs in other selected genes.

Gel shift studies. The results of the gel shift studies to examine RARE binding to RA-RAR are show significant binding of RARE consensus sequences in the GST-π gene to nuclear proteins from MGR-3 cells treated with all-trans RA. The binding could be competed out with excess cold RARES, thus showing them to be RARE-specific. Under the same conditions, no binding of serum albumin controls to the RAREs was observed. Immunoprecipitation showed that after a 48-hr exposure to 1 μM all-trans RA, RAR-β levels in RA-treated cells had increased by more than 3-fold, compared to untreated controls, and that the RARE-nuclear protein complex was immunoreactive with anti-RAR-β antibodies (data not shown). Significantly less RARE binding was observed with nuclear proteins from cells that had not been treated with RA.

Figure 4A:
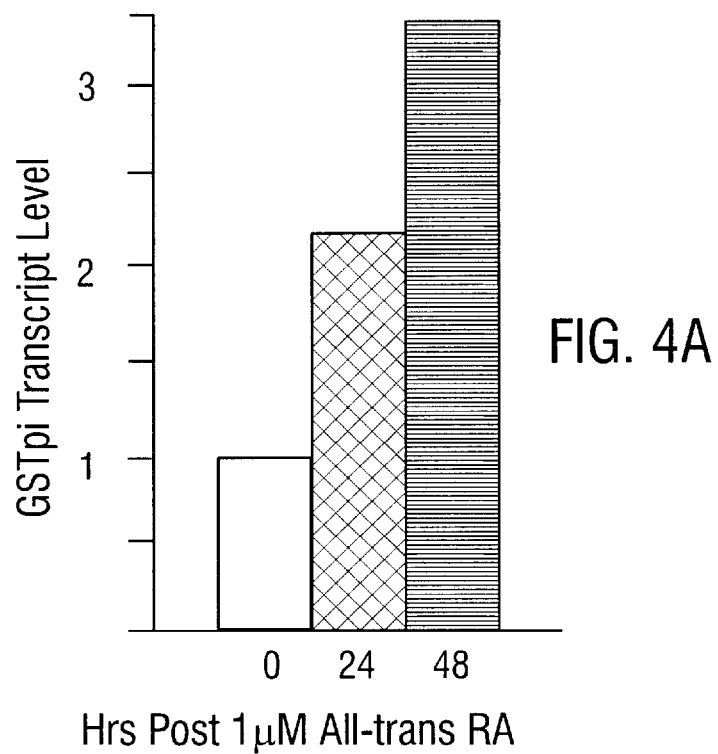
FIGS. 4A, 4B, 4C and 4D. Effect of all-trans RA on GST-π gene expression in MGR-3 cells. Cells were exposed to 1 μM RA for 6 hrs or 48 hrs, after which cells were harvested for northern analysis for GST-π transcripts and GST-π protein.
Figure 4B:
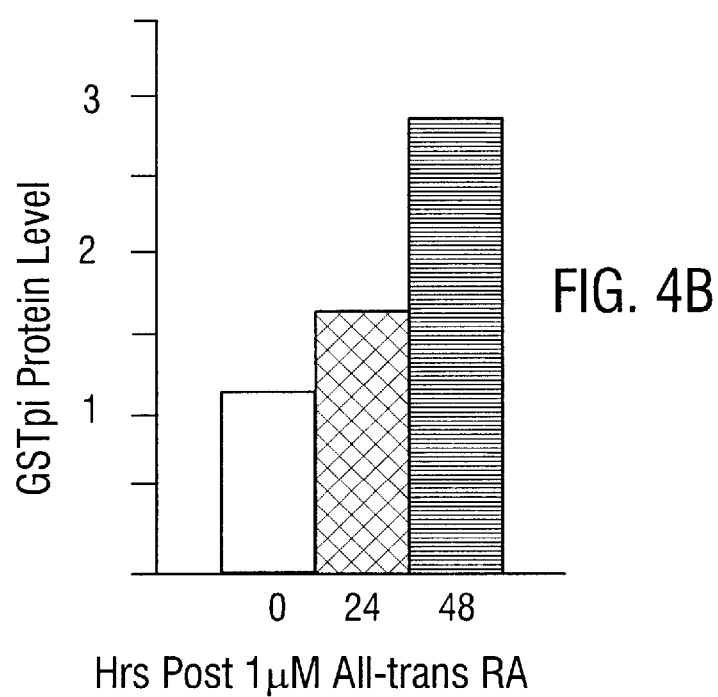
Figure 4C:
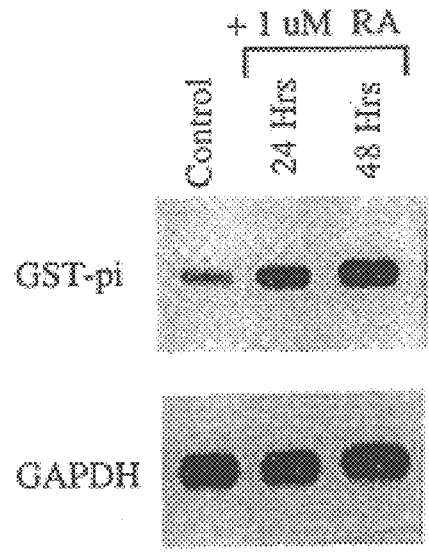
Figure 4D:
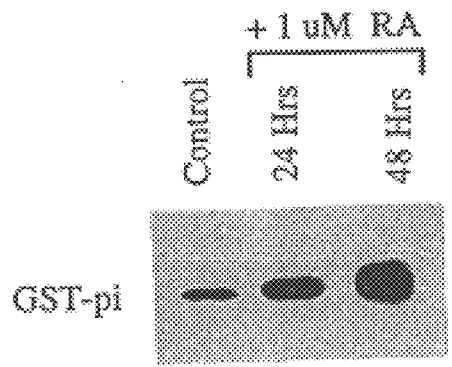

Effect of retinoic acid on GST-π gene expression in MGR-3 cells. The results of these studies designed to examine whether RA was capable of regulating the GST-π gene in MGR-3 cells are summarized in FIGS. 4A, 4B, 4C and 4D. Northern analysis (FIG. 4C) showed a moderate but significant increase in the level of GST-π gene transcripts over 24 and 48 hrs, following exposure of MGR-3 cells to 1.0 μM all-trans retinoic acid, with a maximum of 3.4-fold increase relative to control levels at 48 hr. The Western blot analysis (FIG. 4D) show a similar increase in GST-π protein at 24 and 48 hrs after exposure to 1 μM all-trans-retinoic acid. After 48 hrs, GST-π protein content of RA-treated cells increased by 2.8-fold, relative to untreated controls.

Figure 5:
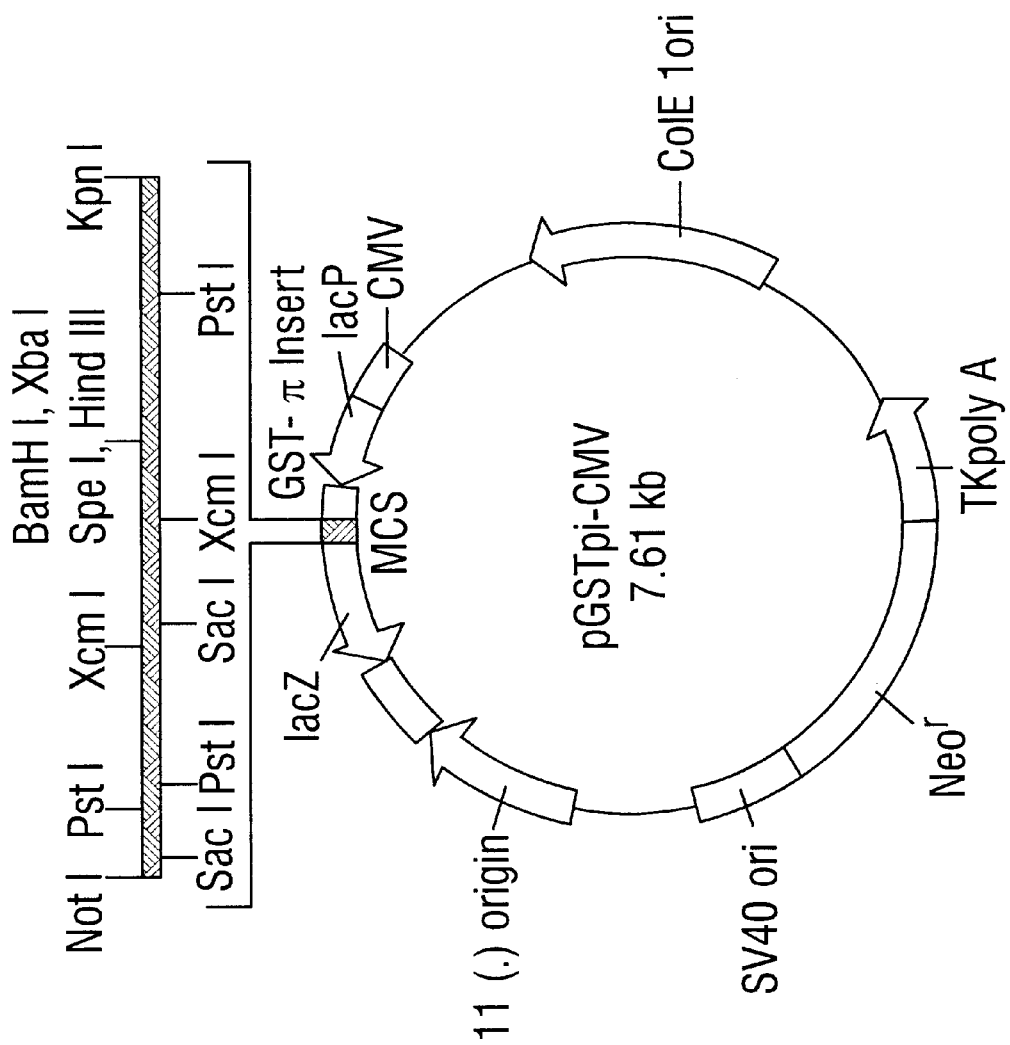
FIG. 5. pCMV-GSTpi eukaryotic expression vector construct.
Figure 6A:
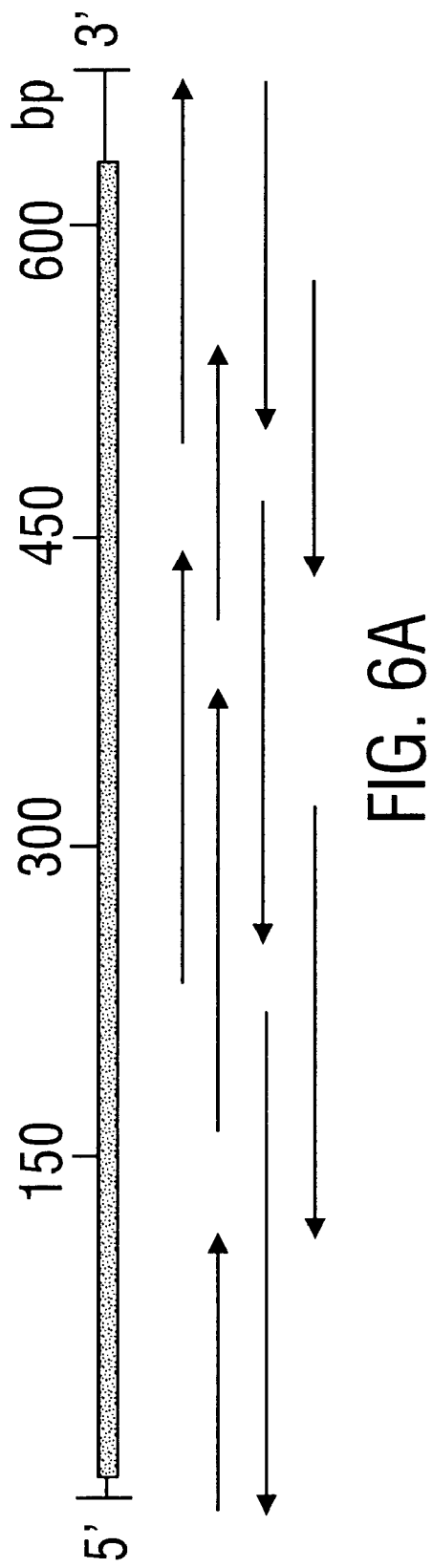

Expression of cloned GST-π gene in COS-1 cells. The structure of the pGSTpi-CMV expression vector is shown in FIG. 5. Western blot analysis for GST-π protein in control COS-1 cells and in COS-1 cells 48 hrs after transfection with the pGSTpi-CMV showed a 2.9-fold increased GST-π protein content in the transfected COS-1 cells relative to controls. Bulk GST enzyme activity was 51.9 and 22.0 nmol/min/mg protein in transfected and control cells, respectively. The similar levels of increase in total GST activity and specific GST-π content by both Western analysis indicates that the increase in GST enzyme activity was due, primarily, to the overexpressed GST-π protein.

TABLE 1

Primers for PCR amplification of overlapping GST-π DNA fragments from SuperCos-GST-πclone.

| Amplified Region of GST-π gene | *Amplification Primers | | Fragment Size (bp) |
|---|---|---|---|
| Exon 2-Exon 3 | P1:CGCAAGCTTCGCCACCATGCCGCCCTACACCG | (SEQ ID NO:9) | 430 |
| | P2:GGAGGCTTTGAGTGAGCCCTC | (SEQ ID NO:10) | |
| Exon 3-Exon 6 | P1:AGATCAGGGCCAGAGCTGGAAG | (SEQ ID NO:11) | 1,700 |
| | P2:CTGGTTCTGGGACAGGGTCTC | (SEQ ID NO:12) | |
| Exon 7-Poly A Site | P1:CTCTGGTCTAGAGGAAGCGA | (SEQ ID NO:13) | 440 |
| | P2:TCTTCCTCTTCTAGTTTGTGAGG | (SEQ ID NO:14) | |
| Exon 2-Exon 7 | P1:TCTTTGTTCGGACCATGCCGCCC | (SEQ ID NO:15) | 2,700 |
| | P2:CAGAGTCCCCCCAACCCTCACTGTTT | (SEQ ID NO:16) | |
| Intron 5 | P1:CAGCCCTGGTGGACATGGTGAATGAC | (SEQ ID NO:17) | 1,000 |
| | P2:CTGGTTCTGGGACAGCAGCTC | (SEQ ID NO:18) | |
| Intron 6 | P1:TGGCAGCTGAAGTGGACAGGATT | (SEQ ID NO:19) | 450 |
| | P2:GATCAGCAGCAAGTCCAGCAG | (SEQ ID NO:20) | |
| RAREs in intron 5 | P1:GTGAGCATCTGCACCAGG | (SEQ ID NO:21) | 123 |
| | P2:GGCTGGTTGATGATGTCCCAGG | (SEQ ID NO:22) | |

*P1 and P2 represent forward and reverse primers, respectively.

TABLE 2

Summary of structural differences between GST-π gene isolated from MGR-3 glioblastoma multiforme cell line (Genbank Accession No. U21689) and that previously reported for the MCF-7 cell line (Genbank Accession No. X08058). Nucleotide alterations and deletions are in bold face.

| Cell Line | Intron/Exon (Nucleotides) | Sequence | Structural Change Modified Endonuclease Cleavage Site |
|---|---|---|---|
| MGR 3 | Intron 1 (+50) | CGCGTC | Guanine insertion; |
| MCF 7 | | CGC TC | CG'CG: Acc II, Aci I, Bsp 50I, BstU I, Mvn I |
| MGR 3 | Intron 2 (+556) | TCC | A→C transversion |
| MCF 7 | | TAC | No known endonuclease site modification |
| MGR 3 | Intron 5 (+1968) | ACTAG | G→A transition; |
| MCF 7 | | ACTGG | A'CTAG: Mae I, Rma I; C'TAG: Spe I |
| MGR 3 | Intron 6 (+2557, +2559) | CCTGGTCC | A→G and C→T transitions; |
| MCF 7 | | CCTAGCCC | 'CCWGG: Apy I, Asu I; CC'WGG: EcoR II |
| | | | G'GWCC: AvaI I, Bme 18I |
| | | | G'GW: Sin I; C'TAG: Mae I, Rma I |
| MGR 3 | Exon 5 (+1404) | GTC | A→G transition |
| MCF 7 | | ATC | ATC (Ile)→GTC (Val) at codon 105 |
| MGR 3 | Exon 6 (+2294) | GTG | C→T transition |
| MCF 7 | | GCG | GCC (Ala)→GTC (Val) at codon 114 |
| MGR 3 | Exon 7 (+2684) | AGC | T→C transition (silent polymorphism) |
| MCF 7 | | AGT | AGT (Ser)→AGC (Ser) at codon 185 |

TABLE 3

Comparison of RARE consensus sequences in human GST-π gene with RAREs in other genes. The RARE half-sites are in bold-face. Spacer regions with greater than six nucleotides are designated by the number of nucleotides.

| Gene | RARE Consensus Half-Site Sequences |
|---|---|
| GST-π | TGACCC CTTCTT GGGTCA 13 N GGGTCA GCTCT GGGCCA 70N GGGTCA |
| RARα2 | GGGTCA TTCAG AGTTCA |
| RARβ2 | GGTTCA CCGAA AGGTGA |
| RARγ2 | GGGTCA GGAGG AGGTGA |
| ApoAI | GGGTCA AG GGTTCA |
| ApoCIII | TGGGCA A AGGTCA |
| PEPCK | CGGCCA A AGGTCA |
| Oxytocin | GGGTCA AGGTCA |
| CRBPI | AGGTCA AA AAGTCA |
| CRBPII | AGGTCA C AGGTCA C AGGTCA C AGTTCA |
| Laminin B1 | AGGTCA GC TAGGTTA 14N GGGTCA |
| ADH3 | GGGTCA TTCAG AGTTCA 11N GGGTCA |
| Oct-3/4 | GGGCCA G AGGTCA AGGCTA |
| Oct-4 | GGGCCA G AGGTCA 28N AGGTGA 10N AGGTGA |

Example 2
Cloning and Expression of Three Human GST cDNAs
1. Materials and Methods Cells, tissues and reagents. PBLs were isolated from the peripheral blood of healthy donors using a single step Ficol-Hypaque gradient centrifugation (Ali-Osman, 1996). Full-term human placentas were obtained after normal vaginal delivery. Primary malignant glioma specimens were obtained incidental to surgery. All specimens were acquired on institutionally approved protocols. Glioma cell lines were established from primary specimens, as previously described (Maurer et al., 1977), and were of less than 40 in vitro passages. Unless otherwise stated, all chemicals were from SIGMA Chemical Co., St. Louis, Mo. Restriction enzymes and biochemicals were from Boehringer Mannheim, Indianapolis, Ind., and PCR reagents from Perkin Elmer Cetus, Norwalk, Conn. Polyclonal antibodies against human GST-α, GST-μ and GST-π were obtained from Biotrin Inc., Dublin, Ireland.

cDNA library synthesis and screening. Polyadenylated RNA was purified on oligo-dT cellulose columns from total RNA isolated from malignant glioma cell lines, using the standard acid guanidinium thiocyanate phenol-chloroform method (Sambrook et al., 1989). λgt 11 cDNA libraries were synthesized from the poly-A RNA according to the modified procedure of Gubler and Hoffman (1983) using the protocol of Clontech, Palo Alto, Calif. After first and second strand cDNA synthesis, the cDNA pool was size-fractionated at a 500 bp cut-off to reduce the proportion of truncated GST-π cDNAs. The double-stranded cDNAs were then blunt-ended with T4 DNA polymerase, methylated with EcoR I methylase and ligated to EcoR I linkers. Following EcoR I digestion to remove excess linkers, the cDNAs were ligated into bacteriophage λgt 11 EcoR1 arms and packaged using the Gigapack 11 Gold packaging extract (Stratagene, La Jolla, Calif.). Serial dilutions of the resulting cDNA libraries were screened using a rapid PCR screening procedure (Takumi and Lodish, 1994), which the inventors had previously modified (Ali-Osman and Akande, 1995) by the use of the Expand™ PCR system (Boehringer Mannheim). Positive cDNA pools were plated on $E.$ $coli$ strain Y109 Or-screened with a $^{32}$P-labeled GST-π cDNA probe and GST-π positive clones amplified, the DNA isolated, purified and sequenced.

DNA sequencing. Nucleotide sequencing was performed with the [$^{35}$S]-dideoxynucleotide chain termination method (Sanger et al., 1977) using the circumvent thermal cycle sequencing protocol (New England Biolabs, Mass.), either directly or, after subcloning into Bluescript phagemid II. Sequencing primers were designed to overlap internal GST-π cDNA regions, as well as, to the vector. Each clone was sequenced twice in both directions.

Restriction site mapping. Computer-assisted analysis (Macmolley Tetra, Berlin, Germany) was used to generate restriction endonuclease maps of the variant GST-π cDNAs, and to identify REs, which had gained or lost restriction motifs as a consequence of the nucleotide transitions. Two of these REs, Mae II and Xcm I, with relatively few restriction sites in the GST-π cDNA, were selected for restriction site mapping. A 484 bp cDNA fragment, spanning positions +112 to +596 of the GST-π cDNA, was amplified by RT-PCR from each specimen, using the primers:

5'-ACGTGGCAGGAGGGCTCACTC-3' (forward SEQ ID NO:23) and

5'-TACTCAGGGGAGGCCAGCAA-3' (reverse SEQ ID NO:24)

For RT-PCR, total RNA was isolated from cells or tissues as described earlier. First strand cDNA synthesis was performed in a 20 ul reaction mixture containing 100 ng reverse primer, 1 μg total RNA, 250 uM dNTPs, 3.2 mM Na pyrophosphate, and 0.4 U/ml each of placental RNAse inhibitor and AMV reverse transcriptase. After 2 mins at 94° C., followed by 1 hour at 42° C., the mixture was heated to 95° C. for 2 mins and rapidly cooled to 25° C. 500 ng of forward and reverse GST-π primers, 200 μM dNTPs, 1.5 μM MgCl$_2$, 0.025 U/ml of Amplitaq polymerase and PCR buffer (to 100 μl) were then added and PCR amplification performed for 34 cycles of 94° C. (1 min), 58° C. (2 mins) and 72° C. (3 mins). The cDNA product was purified and after restriction with Mae II and Xcm I, was electrophoresed in 2% agarose, stained with 0.5 μg/ml ethidium bromide, and the restriction pattern photographed under ultraviolet illumination. Fragment sizes were determined relative to marker DNA (φX174 DNA-Hae III digest) and the structures were confirmed, in representative cases, by nucleotide sequencing.

Southern hybridization of GST-π gene variants. For these studies, 32-mer oligonucleotide probes were designed to contain the nucleotide changes specific to each of the GST-π cDNAs. The probes covered the region +312 to +342 of the GST-π cDNA and had the following sequences:

5'-CATCTCCCTCATCTACACCAACTATGAGGCG-3' (GSTP1*A; SEQ ID NO:25),

5'-CG*TCTCCCTCATCTACACCAACTATGAGGCG-3' (GSTP1*B; SEQ ID NO:26)

5'-CG*TCTCCCTCATCTACACCAACTATGAGGT*G-3' (GSTP1*C; SEQ ID NO:27)

The asterisks indicate the transition nucleotides. Using T4 polynucleotide kinase, each probe was end-labeled with γ-$^{32}$P-ATP to a specific activity of approximately 4×10$^6$ cpm/ml. Southern hybridization was performed using standard methods (Chomcznski and Saachi, 1987) but with more stringent conditions. Briefly, full length GST-π cDNAs were amplified from representative specimens by RNA-PCR, the DNA products were purified and electrophoresed in 2% agarose, as described earlier. After denaturation in 0.5M NaOH and 1.5M NaCl followed by neutralization with 1M Tris HCl (pH 7.4) containing 1.5M NaCl, the DNA was capillary transferred in 10× SSC on to nylon membranes and pre-hybridized at 42° C. for 2 hrs in 50% formamide, 5× SSC, 1% SDS and 100 ug/ml denatured herring sperm DNA. Hybridization with the $^{32}$P-labeled oligonucleotide probe was allowed to proceed overnight at 50° C., after which the membranes were washed in 2× SSC for 30 min at room temperature followed by 1× SSC at 60° C., and autoradiographed on Kodak XAR-5 X-ray film. Following photography, the membranes were stripped of the hybridized probe and reprobed with the next.

GST-π genotype analysis. To determine the concordance between the GST-π genotype and phenotype in a given specimen, the inventors examined the nucleotide sequences of exons 5 and 6, which contained the nucleotide transitions observed in the GST-π mRNA variants. For this, nine representative samples were selected to represent each of the three GST-π mRNA variants. Using genomic DNA, a 305 bp DNA fragment spanning nucleotides +1219 to +1524 of the GST-π gene and containing the entire exon 5 and its flanking regions in introns 4 and 5, as well as, a 321 bp fragment spanning nucleotides +2136 to +2467, including all of exon 6 and its flanking regions in introns 5 and 6 were amplified by PCR. Primers for these amplifications were designed from the inventors' GST-π gene sequence data (GenBank Accession No. U21689) and were as follows:

5'-CCAGGCTGGGGCTCACAGACAGC-3' (forward SEQ ID NO:28) and

5'-GGTCAGCCCAAGCCACCTGAGG-3' (reverse SEQ ID NO:29) for exon 5;
5'-TGGCAGCTGAAGTGGACAGGATT-3' (forward SEQ ID NO:30) and
5'-ATGGCTCACACCTGTGTCCATCT-3' (reverse SEQ ID NO:31) for exon 6.

Prokaryotic expression of variant GST-π proteins. The full-length cDNAs of the GST-π gene variants were amplified by PCR from the respective GST-π clones isolated from the λgt 11 libraries. To facilitate directional subcloning into the expression vector, the forward and reverse primers were designed to contain an EcoR I restriction site and an Xba I site, respectively, at their 5'-termini. Both restriction sites are absent in the GST-π cDNA. After nucleotide sequencing to ensure the absence of PCR-induced mutations, the cDNA products were ligated into the pBK-CMV phagemid vector (Stratagene, La Jolla, Calif.), in which prokaryotic gene expression is driven by the lac promoter and eukaryotic expression by the inmmediate early CMV promoter. Strain XL1 Blue bacteria were transformed with the resulting cDNA constructs, screened for positive clones and bacterial cultures of these grown overnight in LB broth. Isopropyl-β-thiogalactopyranoside was added to 1 mM in the last hour of culture. The bacteria were pelletted by centrifugation, resuspended in 50 mM Tris-HCl (pH 7.4) containing 2 ug/ml lysozyme for 1 hr at 37° C. and ultrasonicated. The crude homogenates were centrifuged at 30,000×g for 20 mins and the supernatants concentrated 10-fold by membrane filtration at a 10 kD molecular weight cut-off. Protein content of the supernatants was determined (Lowry et al., 1951) and GST enzyme activity was assayed, as previously described (Ali-Osman et al., 1990), using CDNB as substrate. SDS-PAGE and western blotting with polyclonal antibodies against human GST-α, -μ, and -π were performed, as previously described (Ali-Osman et al., 1990).

Purification and enzyme kinetic analysis of variant GST-π proteins. Functional consequences of the structural differences in the GST-π variant proteins was determined by the differential ability of the recombinant GST-π proteins to catalyze the conjugation of GSH with 1-chloro-2,4-dinitrobenzene (CDNB), a universal GST substrate. After expression in E. coli, the three GST-π proteins were purified by GSH-affinity chromatography on S-hexyl glutathione linked to epoxy-activated sepharose 6B, as previously described (Simons and Van der Jagt, 1981) and then used for enzyme kinetic analysis. Reaction mixtures (25° C.) in 100 mM potassium phosphate buffer, pH 8.3 contained 0.5–2.5 mM CDNB, 2.5 mM GSH and 0.015 unit of purified GST-π protein. The change in absorbance was monitored at 340 nm over two minutes and used to compute reaction rates. The rates of the spontaneous reactions of GSH with CDNB, determined with reaction mixtures in which the GST-π enzyme was replaced with buffer, were subtracted from the rates of the enzyme catalyzed reactions. The resulting reaction rates were used to generate double reciprocal plots from which Vmax and Km values were determined, using standard methodology (Segel, 1976).

Computer structural modeling of variant GST-π proteins. To determine possible effects of the amino acid changes on the three-dimensional architecture of the three GST-π proteins, the X-ray crystallographic co-ordinates (2.8 A° resolution ) of the placental GST-π (GSTP1a) co-crystallized with S-hexyl-glutathione (Reindeer et al., 1992) were imported from the Brookhaven Protein Databank into the SYBYL molecular modeling program (Version 6.2, 1995; Tripos Associates, St. Louis, Mo.) running on a Silicon Graphics Indigo 2 workstation (IRIX 5.2, 64 MB). GSTP1b was created by substituting Ile for Val at amino acid residue 104, and GSTP1c was obtained by substituting Val for Ile at amino acid residue 104 and Val for Ala at 113, using the SYBYL BIOPOLYMER module. Each monomeric sub-unit of 209 amino acids was energy minimized using the amber all-atom force field in SYBYL. The energy minimized structures were super-imposed using the match function of SYBYL. Changes in atomic co-ordinates and in inter-side chain distances of amino acid residues lining the putative electrophile-(H)-site were examined to determine how these structural changes might predict differences in functional activity.

Stability of variant GST-π gene transcripts. Transcriptional block by actinomycin D has been shown in previous studies to be a reliable method with which to determine mRNA turnover and stability in cells (Dani et al., 1984). The inventors therefore applied this technique to investigate differences in the intracellular stability of the transcripts of the different GST-π genes. Three glioma cell lines, each expressing one of the three GST-π variants, were grown to, approximately, 70% confluency and then refed with fresh culture medium containing 5 μ/ml actinomycin D. Controls were similarly set up but without actinomycin D treatment. At 0, 6, 15 and 24 hrs after actinomycin D exposure, total RNA was isolated from each culture and electrophoresed, as described earlier, at 7.5 μg RNA per lane. After electrophoresis, the gels were stained with ethidium bromide, viewed under ultraviolet light to ensure equal RNA loading of the lanes and transferred to nylon filters. Northern hybridization for GST-π transcript levels was performed as previously described. Hybridization bands were quantitated by densitometry and plotted against time.

Thermostability of variant GST-π proteins. In a previous study (Zimniak et al., 1994), it was shown that a recombinant GST-π enzyme corresponding to GSTP1b-1b, created by site-directed mutagenesis, was functionally more heat-stable than the parent enzyme. In this study, therefore, the inventors compared the thermal stabilities of the enzymatic function of the three variant GST-π proteins. For this, approximately 0.1 U/ml of each variant GST-π protein was incubated at 45° C. in PBS (pH 7.2) in a water bath. Every 15 mins, over 1 hr, a 50 μl aliquot was removed from each incubate and total GST activity was determined as previously described, using CDNB as substrate. Residual GST activity was computed relative to the activity of controls maintained at 25° C. and plotted against time. SDS-PAGE and western blotting were performed, as described earlier, to determine if degradation of the GST-π peptides had occurred during the incubation.

2. Results

Isolation and sequencing of variant GST-π cDNA clones. The inventors analyzed approximately 3×10$^6$ plaque forming units of each cDNA library and several GST-π positive clones were obtained, from which selected clones were subjected to secondary and tertiary screening and subsequent sequencing. Several of the isolated clones contained truncated GST-π cDNAs, however, the inventors obtained three clones, Pi 3A-7, Pi 3B-2 and Pi 3C-9, containing full-length GST-π cDNAs, corresponding to each of three GST-π mRNA variants, which the inventors designated hGSTP1*A, hGSTP1*B and hGSTP1*C, in accordance with the proposed nomenclature for allelic GST gene variants (Mannervik et al., 1992).

The sequencing strategy is shown in FIGS. 6A, 6B, 6C, 6D, 6E, 6F, and 6G and the complete nucleotide and deduced amino acid sequences of the cDNAs are shown in SEQ ID NO:3 and SEQ ID NO:4 (GSTP1*A); SEQ ID NO:5 and SEQ ID NO:6 (GSTP1*B) and SEQ ID NO:7 and SEQ ID NO:8 (GSTP1*C). Each cDNA contained an open reading frame of 630 nucleotides, encoding 210 amino acids, including the initiating methionine. hGSTP1*A was completely identical in nucleotide sequence to the previously reported human GST-π cDNA (Kano et al., 1987; Moscow et al., 1988). It consisted of 712 nucleotides, of which 9 were in the 5' non-coding region. hGSTP1*B differed from hGSTP1*A by having an A→G transition at nucleotide +313 thus changing codon 104 from ATC (Ile)→GTC (Val). Of the 719 nucleotides 12 were in the 5' non-coding region. hGSTP1*C was characterized by two active transitions, the A→G transition at +313 observed in hGSTP1*B, and a C→T transition at +341, resulting in changes of ATC (Ile)→GTC (Val)GCC in codon 104 and of (Ala)→GTC (Val) in codon 113. hGSTP1*C consisted of 723 nucleotides, 13 of which were 5' of the ATG start codon. The 3'-noncoding regions of all three cDNAs were similar and contained the AATAAA polyadenylation signal at +689 to +696. In 8 cases examined, there was complete concordance between the nucleotide sequences of exons 5 and 6 in the genomic DNA and that of the corresponding regions of the mRNA. In addition to the transitions at nucleotide positions +313 and +341, a silent C→T transition at +555 was observed in hGSTP1*B and hGSTP1*C. This transition, also previously observed in the GST-π cDNA isolated by Moscow et al. (1988), does not alter the encoded amino acid (serine) in the affected codon 185.

Figure 7:
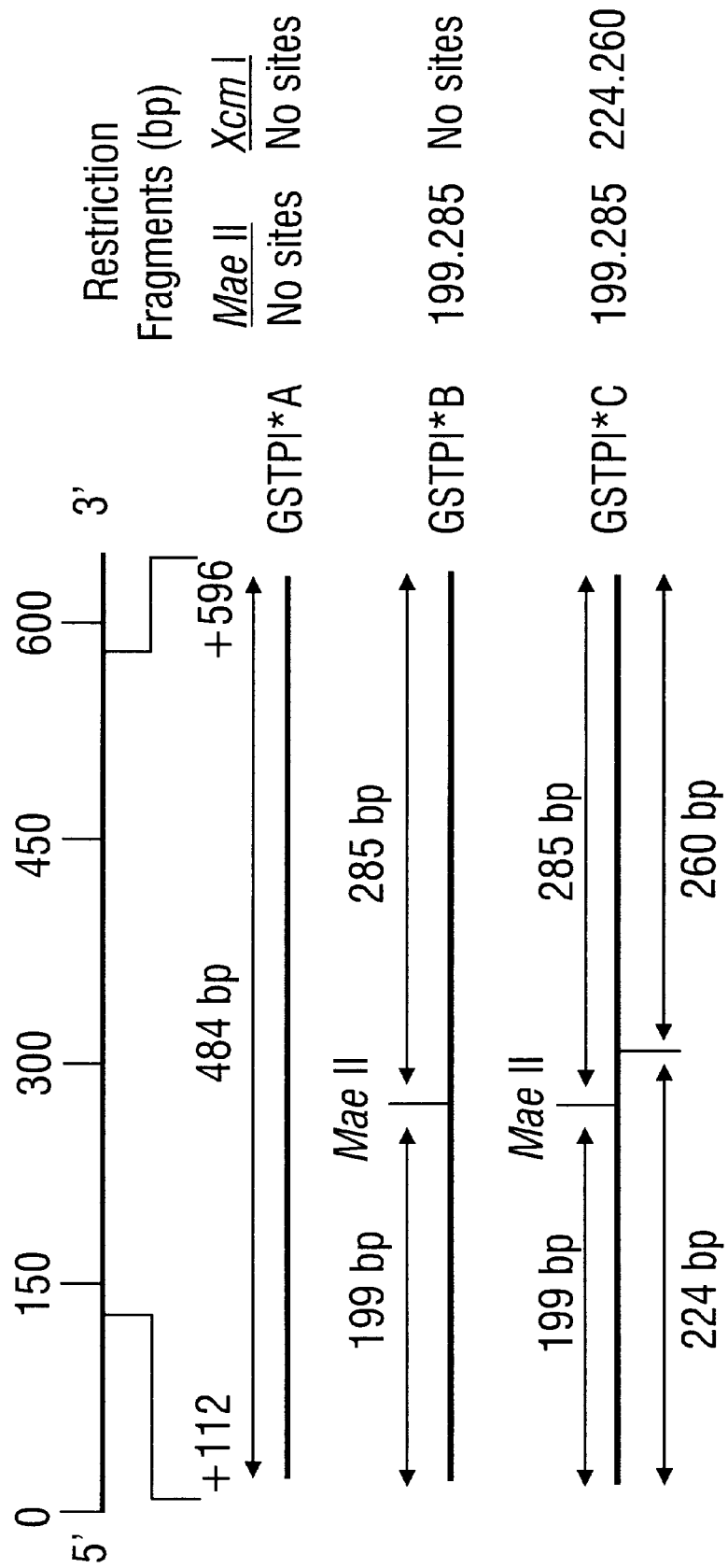
FIG. 7. Mae II and Xcm I restriction endonuclease maps of variant GST-π cDNAs.

Restriction endonuclease mapping. The partial restriction endonuclease maps of the region containing the nucleotide transitions in the three GST-π cDNAs are shown in FIG. 7. The A→G transition at +313 created the Mae II recognition sequence (A'CGT) in hGSTP1*B and hGSTP1*C. Thus Mae II digestion of the 484 bp cDNA from specimens expressing hGSTP1*B and hGSTP1*C yielded two fragments, 199 bp and 285 bp in size. The gain of an Xcm I recognition sequence (CCANNNNN'NNNNTGG SEQ ID NO:34) in GSTP1*C, resulting from the C→T transition at +341, yielded 224 bp and 260 bp fragments upon Xcm I digestion and allowed hGSTP1*C to be differentiated from hGSTP1*A and hGSTP1*B. cDNAs from specimens that expressed hGSTP1*A exclusively were not restricted by either Mae II or Xcm I, since, as shown in FIG. 7, the sites for both REs are absent in this cDNA variant. Direct sequencing of cDNAs obtained by RT-PCR from glioma specimens expressing a mixture of GSTP1*A and GSTP1*B and of GSTP1*A and GSTP1*C revealed the expected sequence.

Detection of expressed GST genes by southern hybridization. The results of the southern hybridizations of the cDNAs generated by RT-PCR from six specimens expressing different GST-π genes are as follows. Both hGSTP1*A and hGSTP1*B specific probes hybridized strongly with their respective DNA. As anticipated, the hGSTP1*C probe did not hybridize with hGSTP1*A DNA and, conversely, the hGSTP1*A probe hybridized only weakly with hGSTP1*C DNA. The strongest hybridization signals were observed when the hGSTP1*C probe was used to probe hGSTP1*C DNA and the least specific hybridization was observed with the hGSTP1*B probe, possibly, because only one nucleotide difference exists between the probe for hGSTP1*B and those hGSTP1*A and hGSTP1*C.

Expression, purification and functional analysis of variant GST-π proteins. The GST-π peptides encoded by the three GST-π genes were designated GSTP1a, GSTP1b and GSTP1c, as previously recommended (Mannervik et al., 1992). The cDNAs were expressed in *E. coli* and the expressed proteins purified by GSH-affinity chromatography. The inventors achieved, approximately, a 200-fold purification for all three GST-π proteins, with a yield of 78%, 63% and 72% for GSTP1a-1a, GSTP1b-1b and GSTP1c-1c, respectively. In each case, SDS-PAGE of the isolated proteins showed a single band after Coumassie Blue staining and positive immunoreactivity was observed by western analysis with anti-GST-π antibody but not with antibodies against GST-μ or GST-α. Enzyme kinetic analysis of the catalysis of the conjugation of GSH with CDNB by the three GST-π proteins are summarized in the Lineweaver-Burke plots in FIGS. 8A–C and in Table 4. $K_m$ (CDNB) and $V_{max}$ values were 0.98 mM±0.06 and 4.7±0.03 $\mu$mol·min$^{-1}$·mg$^{-1}$, respectively, for GSTP1a-1a, 2.7±0.023 mM and 1.7±0.087 $\mu$mol·min$^{-1}$·mg$^{-1}$ for GSTP1b-1b, and 3.1±0.17 mM and 1.4±0.23 $\mu$mol·min$^{-1}$·mg$^{-1}$ for GSTP1-1c.

Figure 9A:
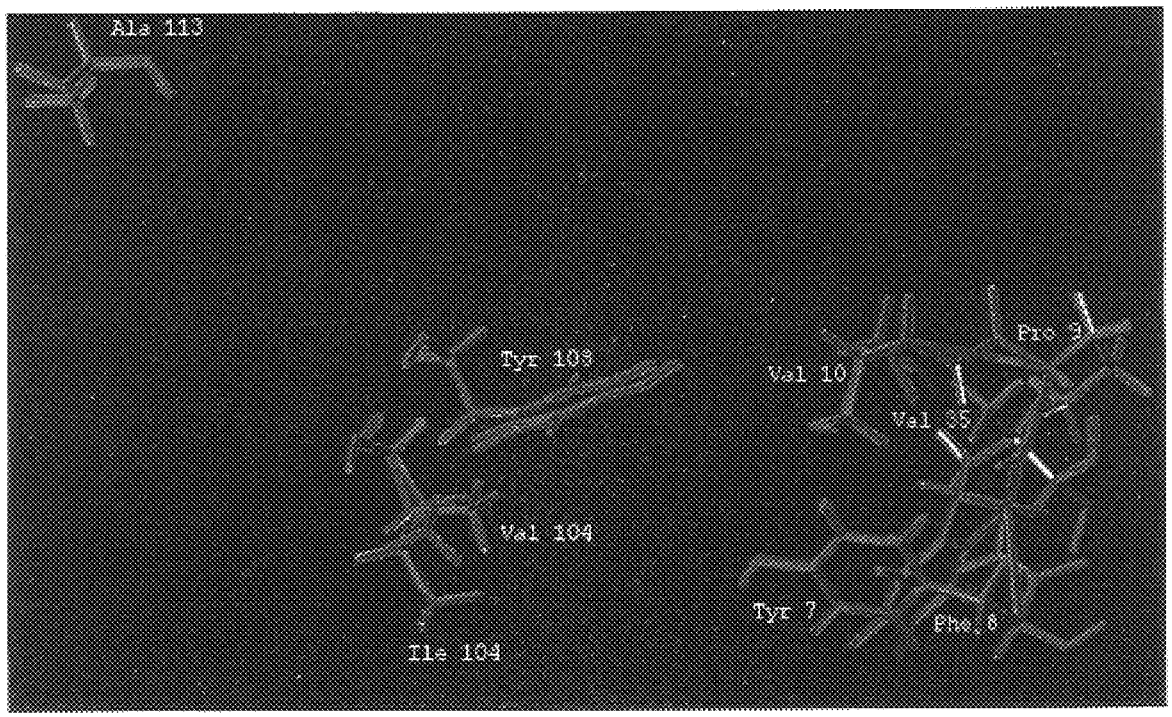
FIGS. 9A and 9B. Super-imposed energy-minimized 3-dimensional architecture of the H-site region of the GSTP1a (red), GSTP1b (cyan) and GSTP1c (yellow), showing the deviations in the side chains relative to each other. GSTP1b and GSTP1c were created by substituting $Val_{104}$ for $Ile_{104}$ (FIG. 9A), and both $Ile_{104}$ and $Ala_{113}$ with Val (FIG. 9B) in the X-ray crystallographic structure of the human placental GSTP1a (Reindeer et al., 1992; Reinemer et al., 1993), imported from the Brookhaven Protein Databank.

Structural analysis of variant GST-π proteins. Data from the X-ray crystallographic structure of GSTP1a, previously reported (Reindeer et al., 1992; Reinemer et al., 1993) showed the key amino acid residues lining the putative electrophile-binding (H-) site of human placental GST-π to consist of $Tyr_7$, $Tyr_{108}$, $Val_{10}$, $Val_{35}$, $Phe_8$ and $Gly_{205}$. The inventors modeled the effects of the amino acid substitutions in the variant GST-π proteins on the structure of the resulting peptides, particularly, the active (H-) site. The superimposed energy-minimized structures of the H-site region of GSTP1a and GSTP1b are shown in FIG. 9A, and in FIG. 9B for GSTP1a and GSTP1c. The substitutions of $Va_{104}$→$Ile_{104}$ in GSTP1b and GSTP1c, and of $Val_{113}$→$Ala_{113}$ in GSTP1c caused significant deviations in the atomic co-ordinates of side chains of the key H-site residues (Table 5). The deviations caused by the $Val_{104}$ for $Ile_{104}$ substitution are magnified in the same direction, but to a lesser degree, than those caused by the $Ala_{113}$ to $Val_{113}$ substitution. The highest deviations involved the side chains of $Tyr_{108}$ and $Tyr_7$, which, relative to GSTP1a, had shifted by 0.153 A° and 0.116 A° in GSTP1b, and 0.242 A° and 0.185 A° in GSTP1c. $Phe_8$ was the least affected by the amino acid changes. Overall, the deviations in atomic coordinates in the active site residues were larger going from GSTP1a to GSTP1c than from GSTP1b to GSTP1c.

Figure 9B:
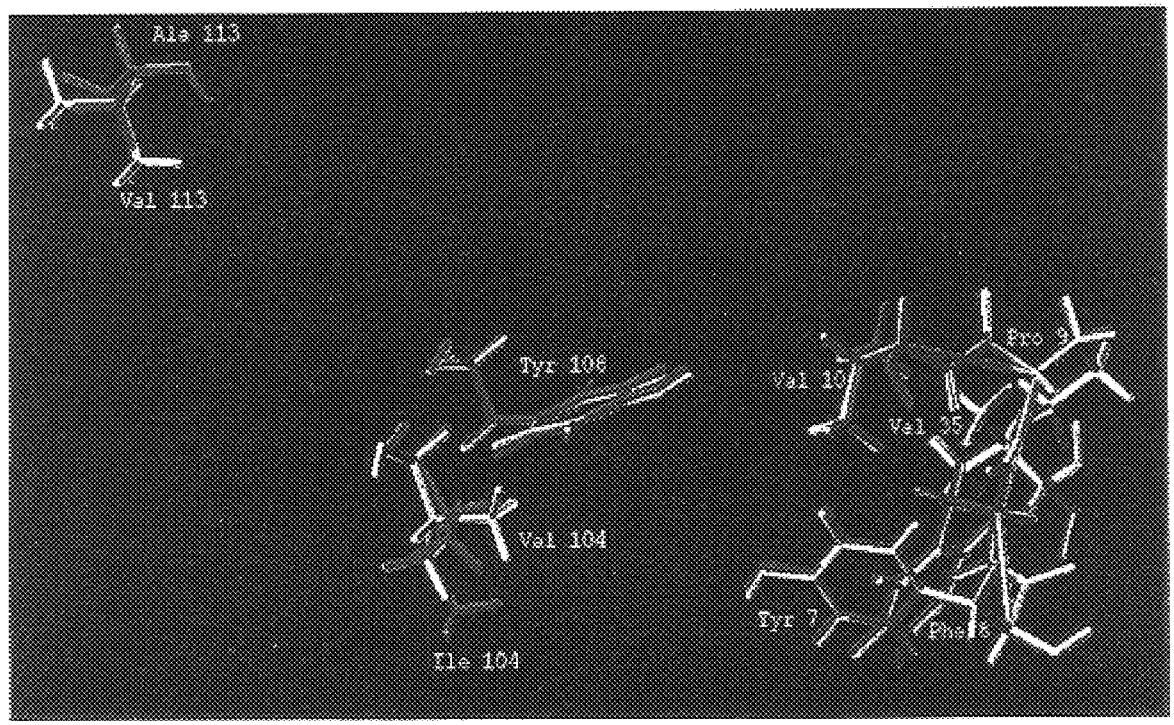

Changes in inter-side chain distances within the three-dimensional structure of the variant peptides are summarized in Table 6, and are also evident in FIG. 9A and FIG. 9B. The distances between the residues $Tyr_{108}$ and $Val_{10}$, and between $Tyr_{108}$ and $Val_{35}$ decreased progressively going from GSTP1a to GSTP1b and GSTP1c. From the superimposed structures in FIG. 9A and FIG. 9B, it is apparent that, in GSTP1b and GSTP1c, the methyl group of $Val_{104}$ proximal to $Tyr_{108}$ is closer to several of the putative active site residues than is the secondary methyl group of $Ile_{104}$ in GSTP1a. The orientation of the methyl group of $Val_{104}$ in GSTP1b and GSTP1c towards $Tyr_{108}$, causes a decrease in the distances between $Val_{104}$ and both $Val_{10}$ and $Val_{35}$, and a restriction of the region of the active site bordered by $Tyr_{108}$, $Val_{10}$, and $Val_{35}$. The replacement of $Ile_{104}$ with the less bulky $Val_{104}$ also opens up the region lined by $Tyr_7$, $Tyr_{10}$, $Phe_8$. The distances between side-chains of the paired residues, $Tyr_7$ and $Val_{10}$ is shorter in GSTP1a than in both GSTP1b and GSTP1c, whereas the distances between $Tyr_7$ and $Tyr_{108}$ and between $Tyr_7$ and $Phe_8$ are longer.

Figures 10A, 10B, 10C:
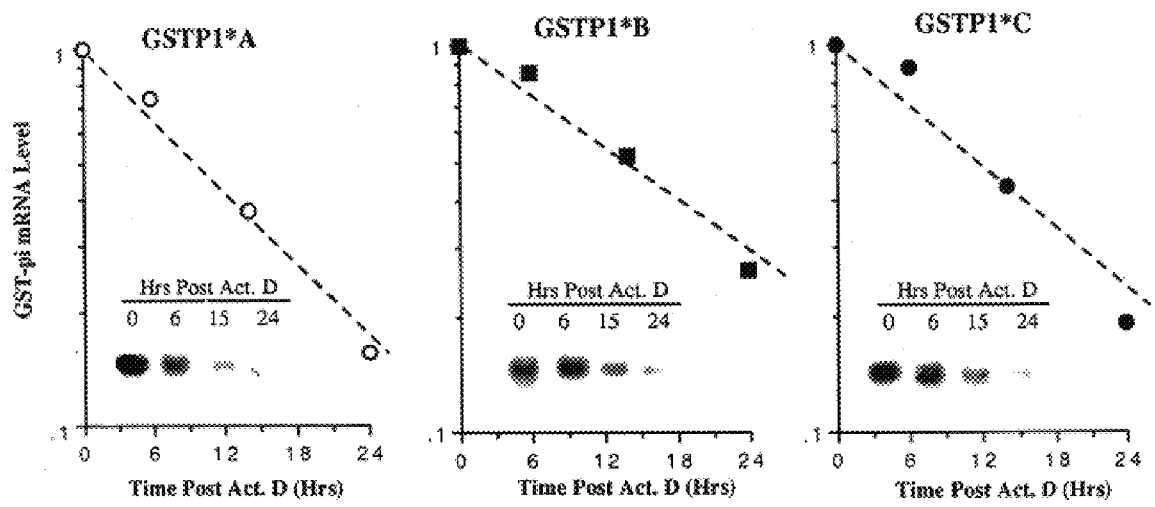
FIGS. 10A–C. Intracellular stability of variant GST-π mRNAs. Total RNA was isolated from cells treated with actinomycin D to block de novo RNA synthesis. The cell lines each expressed only one GST-π mRNA variant.

Stability of variant GST-π mRNAs and protein. The intracellular decay of the three variant GST-π mRNAs in malignant glioma cell lines, each of which expressed a different GST-π mRNA, was determined following inhibition of de novo RNA synthesis by exposure of the cells to actinomycin D. The decay curves, FIGS. 10A–C, showed only a modest difference in the intracellular stabilities of transcripts of the three variant GST-π genes under these conditions. The decay of the GST-π message in each cell line followed first order kinetics with half-lives of 9.4, 14.1 and 11.8 hrs, for GSTP1*A, GSTP1*B and GSTP 1*C, respectively.

Figure 11C:
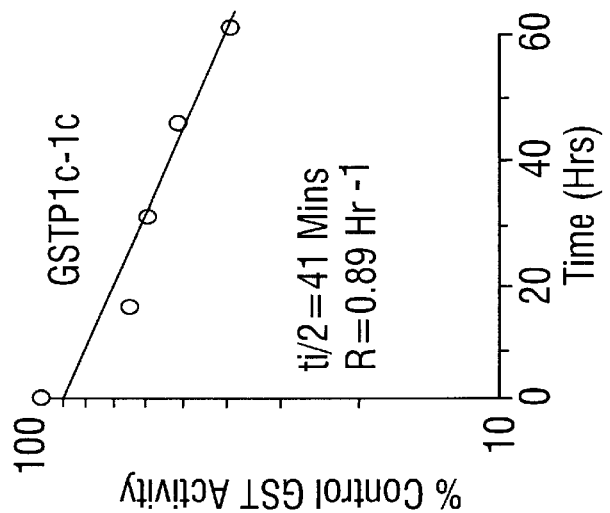
FIGS. 11A–C. Thermal stability of variant GST-π proteins. Recombinant GSTP1a-1a (FIG. 11A), GSTP1b-1b (FIG. 11B) and GSTP1c-1c (FIG. 11C) were incubated at 45° C., and every 15 mins, over one hour, residual GST activity was determined with CDNB as substrate.
Figure 11B:
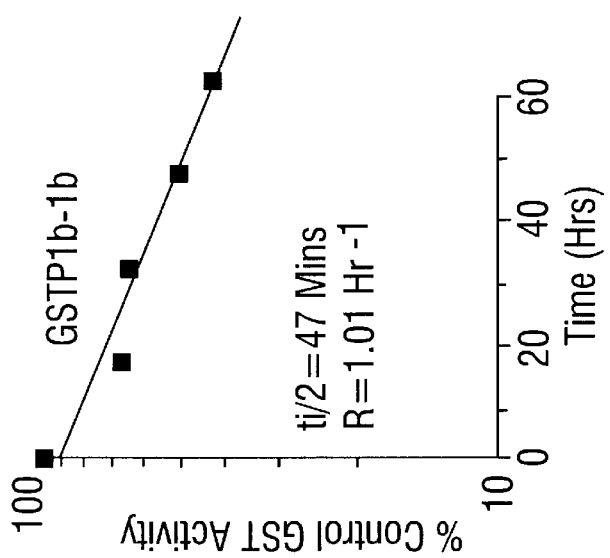
Figure 11A:
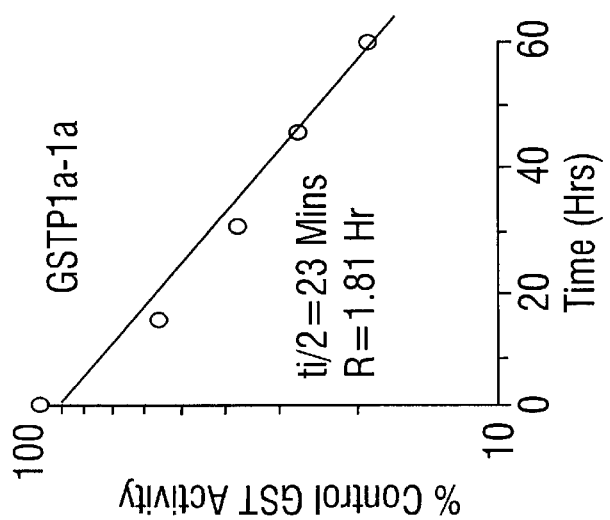

The time-dependent loss of enzymatic activity of the three variant recombinant GST-π proteins at 45° C. also followed first order kinetics and was relatively rapid. The results, summarized in FIGS. 11A–C, demonstrated significant differences between the three enzymes. The rates with which GST enzyme activity (CDNB as substrate) was lost at 45° C. were 1.81 $hr^{-1}$ for GSTP1a-1a, 1.01 $hr^{-1}$ for GSTP1b-1b, and 0.89 $hr^{-1}$ for GSTP1c-1c, with half lives of 23 mins, 47 mins and 51 mins, respectively. SDS-PAGE and western blotting showed no detectable degradation in the GST-peptides associated with the loss in enzyme activity under these conditions.

Expression and distribution of variant GST-π mRNA in normal cells, tissues and tumors. The frequencies with which the three GST-π gene variants were observed in malignant gliomas and normal specimens (lymphocytes and placentas) are summarized in Table 7. The frequency of GSTP1*A homozygosity was 0.22 (7 out of 32) for gliomas compared to 0.51 (22 out of 43) for normal specimens. In contrast, GSTPI*C homozygousity was at a frequency of 0.07 (3 out of 43) in normal specimens, and 0.0.25 (8 out of 32) in gliomas. GSTP1*A/GSTP1*C heterozygosity was observed at frequencies of 0.34 and 0.09 for gliomas and normal specimens, respectively. Thus, overall, GSTP1*C was present at a frequency of 0.59 in gliomas compared to 0.16 in normal specimens. Two of 43 normal specimens and none of the gliomas were homozygous for GSTP1*B. However, the frequency of GSTP1*A/GSTP1*B heterozygosity was significantly higher, 0.19 in gliomas and 0.28 in normal specimens, respectively. None of the 75 tumor and normal specimens were lieterozygous for GSTP1*B and GSTP1*C.

TABLE 4

Enzyme kinetics of recombinant variant GST-π proteins. Each protein was isolated by GSH affinity chromatography and examined for its ability to catalyze the conjugation of GSH with CDNB. Km and Vmax were determined at 25° C. in 0.1M K-phosphate buffer (pH 8.3).

| | 1-Chloro-2,4-dinitrobenzene | |
| --- | --- | --- |
| GST-π Protein Variant | Vmax (umole/min/mg) | Km (mM) |
| GSTP1a—1a | 4.7 ± 0.03 | 0.98 ± 0.06 |
| GSTP1b—1b | 1.6 ± 0.087 | 2.7 ± 0.023 |
| GSTP1c—1c | 1.4 ± 0.23 | 3.1 ± 0.17 |

TABLE 5

Deviations in atomic co-ordinates of key amino acid side chains in H-site amino acid residues of variant GST-π peptides. GSTP1b was created by substituting $Val_{104}$ for $Ile_{104}$, and GSTP1c by substituting both $Ile_{104}$ and $Ala_{113}$ with Val in the X-ray crystallographic structure of the human placental GSTP1a, co-crystallized with S-hexylglutathione (Reindeer et al., 1992; Reinemer, et al., 1993). The resulting 3-dimensional structures were energy minimized. The reference group of the amino acid side chain side chain is in parenthesis and the reference atom is bold-faced and underlined. The reference $CH_3$ for $Val_{10}$ is the one proximal to $Phe_8$, and for $Val_{35}$, the one proximal to $Val_{10}$ in FIGS. 8A–C

| Reference Position in GST-π Peptide | Co-ordinate Deviation Relative to GSTP1a | |
| --- | --- | --- |
| | GSTP1b | GSTP1c |
| $Tyr_{108}$ (OH) | 0.153 | 0.242 |
| $Val_{10}$ ($CH_3$) | 0.099 | 0.188 |
| $Phe_8$ (Ph-H4) | 0.034 | 0.098 |
| $Tyr_7$ (OH) | 0.116 | 0.185 |
| $Val_{35}$ ($CH_3$) | 0.101 | 0.133 |
| $Pro_{11}$ (β-$CH_2$) | 0.108 | 0.126 |

TABLE 6

Changes in inter-side chain distances of amino acid residues lining the H-site of variant GST-π peptides. GSTP1b and GSTP1c were created by amino acid substitutions in the X-ray crystallographic structure of GSTP1a, and energy minimized, as described in the text. The distances are those between the closest atom pair (one in each side chain).

| | Inter-side chain distance (A°) | | |
| --- | --- | --- | --- |
| Amino Acid Residue | GSTP1a | GSTP1b | GSTP1c |
| $Tyr_{108}$ and $Val_{10}$ | 4.358 | 4.211 | 4.156 |
| $Tyr_{108}$ and $Val_{35}$ | 8.883 | 8.683 | 8.638 |
| $Tyr_7$ and $Val_{10}$ | 2.489 | 2.613 | 2.660 |
| $Tyr_7$ and $Tyr_{108}$ | 9.761 | 9.751 | 9.715 |
| $Tyr_7$ and $Phe_8$ | 2.958 | 2.936 | 2.935 |

TABLE 7

Distribution frequency of polymorphic GST-π mRNA variants among normal specimens (peripheral blood lymphocytes, normal brain and placenta) and malignant gliomas.

| Gene Variant | All Specimens N = 75 | Gliomas N = 32 | Normal Specimens N = 43 | Tumor:Normal Ratio |
| --- | --- | --- | --- | --- |
| GSTP1*A | 0.38 (29/75) | 0.22 (7/32) | 0.51 (22/43) | 0.43 |
| GSTP1*B | 0.03 (2/75 | 0 (0/32 | 0.05 (2/43) | 0 |
| GSTP1*C | 0.15 (11/75) | 0.25 (8/32) | 0.07 (3/43) | 3.57 |
| GSTP1*A + GSTP1*B | 0.24 (18/75) | 0.19 (6/32) | 0.28 (12/43)) | 0.67 |
| GSTP1*B + GSTP1*C | 0 (0/75) | 0 (0/32) | 0 (0/43) | 0 |
| GSTP1*A + GSTP1*C | 0.20 (15/75) | 0.34 (11/32) | 0.09 (4/43) | 3.78 |

Example 3
Glutathione S-Transferase π Expression and Subcelllular Localization in Gliomas 1. Materials and Methods Antibodies, biochemical and other reagents. Rabbit polyclonal antibody against human placental GST-π was obtained from Biotrin Inc., Dublin, Ireland, and was tested at various dilutions to determine the optimum concentration required for reproducible immunohistological staining with minimum background staining Mouse anti-rabbit antibody and non-immunized rabbit IgG were purchased from Becton-Dickenson, Palo Alto, Calif. The same batch of antibodies was used throughout the study. All other reagents, unless otherwise stated, were purchased from Sigma Chemical Company, St. Louis, Mo.

Patients and Tumors. All patients in the study had surgery at the M.D. Anderson Cancer Center (MDACC) and the study had received prior approval of the Institutional Review Board (IRB). Both surgery and diagnosis were made independent of the study.

All specimens were processed by fixation for 6–24 hrs in neutral 10% formalin and stained with hematoxylin-eosin. After histological diagnosis and grading of the tumors by a neuropathologist, 4 μm-thick sections were cut from each specimen for GST-π immunocytochemical analyses of GST-π expression. Upon completion of the GST-π immunocytochemical analyses, the data were provided to a biostatistician who obtained, from patient hospital records, the relevant clinical and histological information required for the statistical correlations. Reference points for survival were the date of surgery, date of last follow-up or date of death. For this study, tumors were categorized into one of the following groups: glioblastoma multiforme, anaplastic astrocytoma and other gliomas (consisting of astrocytomas, aligo-astrocytomas and anaplastic oligo-astrocytomas) a categorization that has been shown to be prognostically relevant (Nelson et al., 1983; Burger et al., 1985).

Immunocytochemistry for GST-π expression. Paraffin sections were pre-warmed to 60° C., deparaffinized in two exchanges of xylene, rinsed in decreasing concentrations (100% to 70%) of ethanol and rehydrated in PBS. Endogenous peroxidase was inactivated with 0.3% $H_2O_2$ in methanol and the slides were incubated overnight with a polyclonal rabbit anti-human GST-π antibody at a 1:500 dilution. After rinsing the slides with four exchanges of PBS, they were incubated with a mouse anti-rabbit antibody for 30 mins at 4° C., followed with a solution of biotinylated peroxidase (Vector Laboratories, Burlingame, Calif.). The slides were developed with 0.05% diaminobenzidine and 0.01% $H_2O_2$ in 50 mM Tris/HCl buffer, pH 7.5. Non-immunized rabbit IgG was used as a negative control for the GST-π antibody, and the MGR 3 glioblastoma cell line was used as a positive control for GST-π staining.

Quantitation of the level of GST-π expression and evaluation of its sub-cellular localization. Following immunocytochemical staining as described above, the level of GST-π expression in each specimen was determined by scoring the staining intensity of a xxxfields, at 200× magnification. GST-π staining intensity was assessed as low, moderate or high, based on the staining characteristics of 70% or greater of tumor cells. Since cytoplasmic GST-π immunoreactivity was always positive in GST-π expressing cells, sub-cellular GST-π expression was characterized as either the presence or the absence of GST-π immunoreactivity in the nuclei of tumor cells. The GST-π staining characteristics of other non-tumor cells, e.g., reactive astrocytes, endothelial cells and infiltrating lymphocytes were also determined but not used in the evaluation of GST-π expression in the tumors.

Statistical analysis. The relationship between GST-π expression and histology was determined using the Kruskal-Wallis test (exact version). The presence of nuclear GST-π in glioma cells as a function of age was determined by probability estimates. The correlation of the level of GST-π expression, and of the presence or absence of nuclear GST-π in glioma cells with patient survival was determined by both univariate and multivariate analyses, using the Cox proportional hazard regression model (Cox 1972). Survival estimates were computed and plotted by the Kaplan-Meier (1972) method. Covariates in the multivariate analyses were age (continuous) and histology.

2. Results

Tumor and Patient Characteristics. Tumors from 61 patients were examined in this study. The distribution of these specimens according to histopathology is shown in Table 8. Fifty-four percent of the specimens were flioblastoma multiforme, 21% anaplastic astrocytomas, and 25% other gliomas. Of the 61 patients, 59 were newly diagnosed and had received no prior therapy prior to the analysis for GST-π expression. The remaining two were recurrent glioblastomas.

Pattern and heterogeneity of GST-π staining. The degree of GST-π immunoreactivity in the tumors ranged from low or absent, to intermediate and strong. Each tumor was thus easily categorized semi-quantitatively into one of three groups, namely, low, moderate and high, with respect to the degree of GST-π expression. Such a categorization of GST-π immunoreactivity has been shown to be prognostically relevant (Gilbert et al., 1993; Tidefelt et al., 1992). In GST-π positive tumors, regardless of the intensity, immunoreactivity was always exclusively in glioma cells and, in some cases, also in reactive astrocytes. While the cytoplasm of GST-π positive tumors was always positive, cell nuclei were either positive or negative for GST-π. One example showed a glioblastoma multiforme in which both the nuclei and cytoplasm of glioma cells are strongly positive for GST-π, and another showed a glioblastoma in which the cytoplasm of the tumor cells had strong GST-π staining and the cell nuclei were GST-π negative. When both nuclear and cytoplasmic GST-π staining were present in a given tumor, the pattern and intensity were generally similar, and the two sub-cellular compartments were often indistinguishable with respect to GST-π staining. In the majority of tumors, the overall level of GST-π immunoreactivity was uniform within different regions of a given tumor section, however, in a number of cases, a significant degree of inter-cellular heterogeneity was observed in GST-π staining. Cells with strong nuclear and cytoplasmic GST-π expression can be observed adjacent to cells negative for GST-π or to cells which express only cytoplasmic GST-π. Nuclear GST-π was always absent in reactive astrocytes, even when the cytoplasm was strongly positive. Normal non-reactive astrocytes were generally negative, as were endothelial cells, and tumor-infiltrating lymphocytes, present either as perivascular cuffs or diffuse within the tumor. Necrotic areas in the tumor were negative for GST-π.

Relationship between the level of GST-π expression, histology and patient age. The distribution of the histological categories of gliomas according to their level of GST-π expression is summarized in Table 8. Although, a trend indicating an association of increased levels of GST-π staining with increased grade of gliomas was observed, the correlation was not statistically significant (p-value 0.16). Within each histological category, however, a strong association existed between the proportions of tumors expressing high or low GST-π and histological grade of that category.

Thus, of the glioblastomas, 45% had high and 27% low GST-π expression, compared to 31% and 15% of anaplastic astrocytoma, and 27% and 47%, respectively, of other, primarily lower grade gliomas.

The statistical analyses of the correlation of GST-π staining with age are shown in Table 9. The median ages for patients with high, moderate and low GST-π expressing tumors was 58, 46 and 48 yrs, respectively. There was a modest trend towards higher GST-π levels in gliomas of older patients, however, the correlation was modest and not statistically significant; p-values=0.27 for all glioma patients, 0.16 for patients with glioblastoma multiforme and 0.23 for anaplastic astrocytoma patients. No association was observed between the level of GST-π expression and age in the group of other gliomas (p-value=0.78).

Relationship between nuclear GST-π, histology and patient age. Based on the nuclear GST-π staining characteristics, gliomas were dichotomized into two categories, one in which GST-π was present in the nuclei of tumor cells and the other in which it was absent. The results (Table 10) show a strong correlation (p-value of 0.0003) between the level of GST-π expression and the presence/absence of nuclear GST-π. 74% of gliomas with high GST-π expression also had GST-π present in the nucleus, compared to 55% of tumors with moderate and 11% with low GST-π levels. In contrast to the level of GST-π expression, the correlation between patient age and nuclear GST-π presence was highly significant, with a p-value of 0.0024 by Kruskal-Wallis analysis. Seventy-nine percent of the tumors of patients aged 60–75 yrs. had nuclear GST-π, compared to 22% of the tumors of patients between 15 and 39 yrs. of age. The median age of glioblastoma patients with no nuclear GST-π was 50 yrs. (range 49–75 yrs.) compared to 65 yrs. (range 30–69) for those with nuclear GST-π. As shown in Table 10, no statistically significant correlation was observed between histology and the presence of nuclear GST-π in glioma cells (p-value=0.63 by exact chi-squared analysis).

Correlation of the level and subcellular pattern of GST-π expression with patient survival. Univeriate and multivariate Cox proportional hazard regression models were used to examine the relationship between the level of GST-π expression and patient survival. The multivariate analysis were performed adjusting for histological grade of the tumor and patient age. The results of these analyses, summarized in Table 11, show that patients with tumors with high (or moderate) GST-π levels were at a significantly higher risk than those with low GST-π expressing tumors. The relative risk of high, compared to low GST-π, was 3.2 (95% C.I. 1.4, 7.5), with a p-value of 0.0069 by univariate analysis, and 2.6 (95% C.I. 1.1, 6.2), p-value of 0.036 by multivariate analysis. Similar values were observed when patients with moderate and low GST-π expressing tumors were compared. When contrasted with its absence, the relative risk of the presence of nuclear GST-π was 1.98 (95% C.I. 1.43, 2.75), p-value=0.0010 by univariate analysis, and increased to 4.4 (95% C.I. 2.1, 9.2), p-value 0.0001, by multivariate analysis.

Figure 12A:
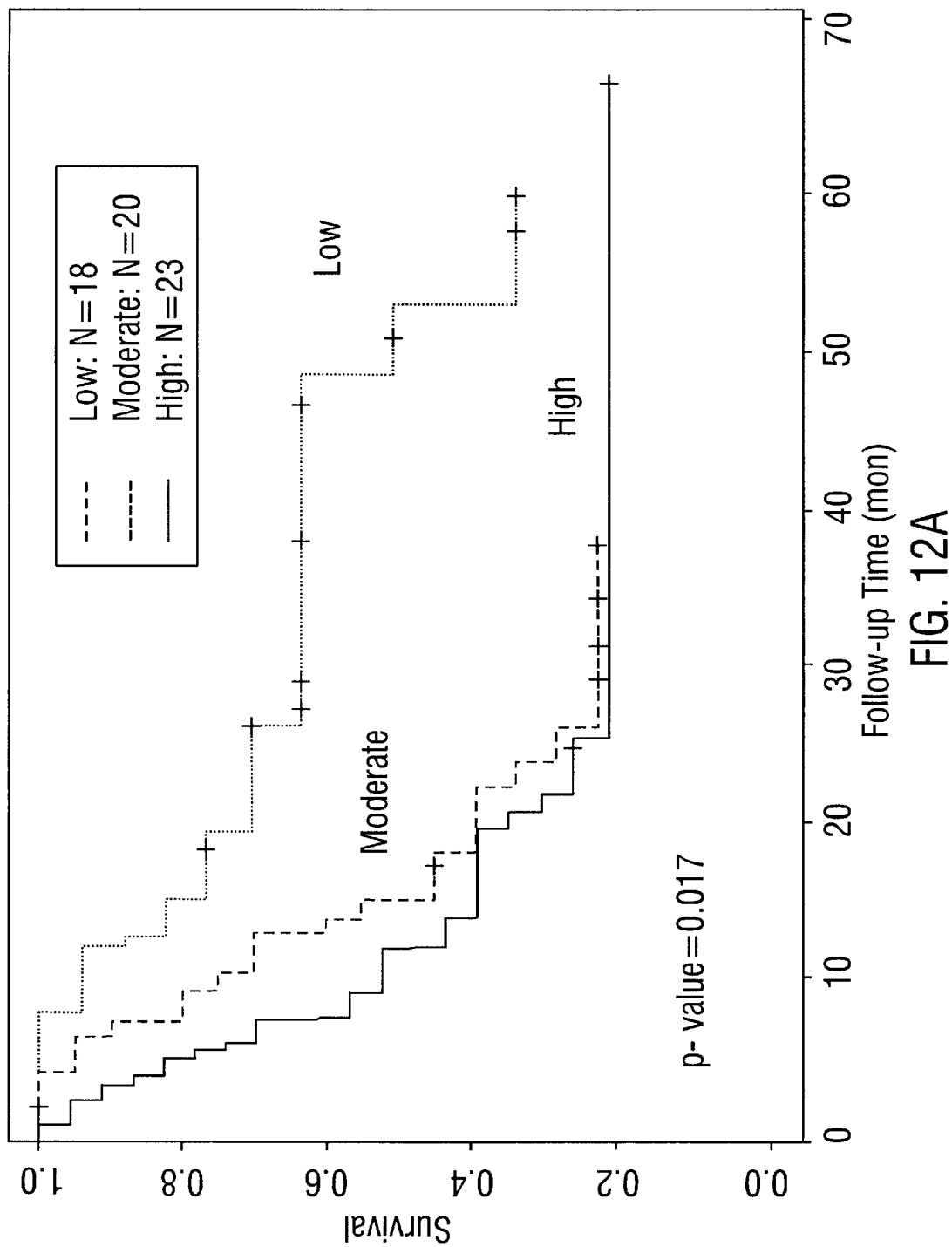
FIGS. 12A and 12B. Kaplan-Meier curves showing the relationship between low, moderate and high levels of GST-π expression in malignant gliomas and patient survival.
Figure 12B:
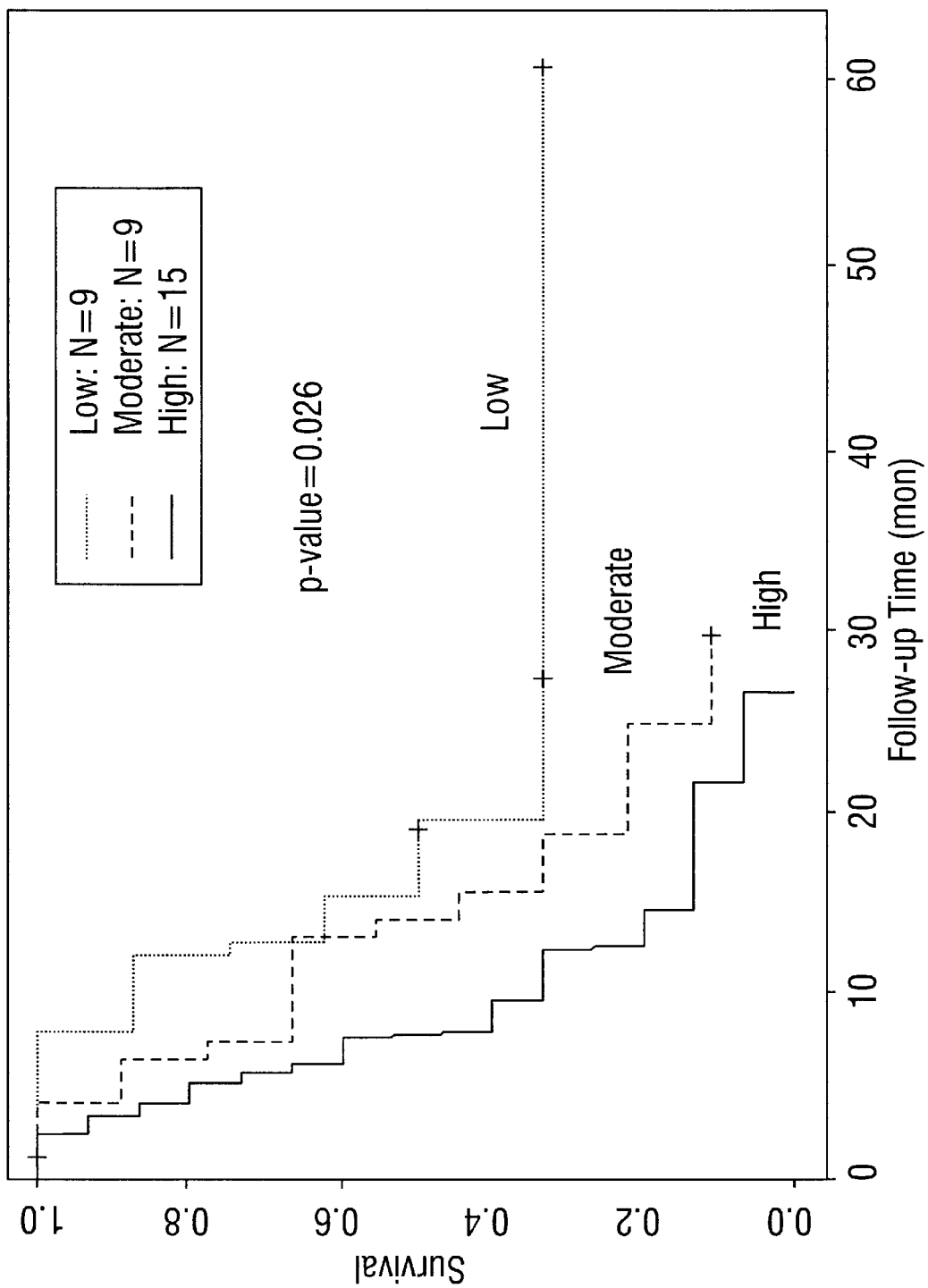

The Kaplan-Meier survival plots for all 61 patients, FIG. 12A, show a strong inverse relationship between the level of GST-π expression and patient survival over the first 52 months of follow-up, with a p-value of 0.017. The difference in survival of patients whose tumors exhibited high or moderate GST-π expression became progressively smaller with longer follow-up time. Because glioblastoma multiforme has the worst prognosis of malignant gliomas, we analyzed the sub-group of glioblastoma patients for the correlation of GST-π expression and survival. The results, FIG. 12B, demonstrate a significantly lower survival rate for glioblastoma patients with high GST-π expressing tumors compared to those whose tumors expressed low or no GST-π in the tumor cells (p-value=0.026). Similar to the data for all patients, the differences in patient survival between the different levels of GST-π expression was highest at the earlier stages of follow-up.

Figure 13A:
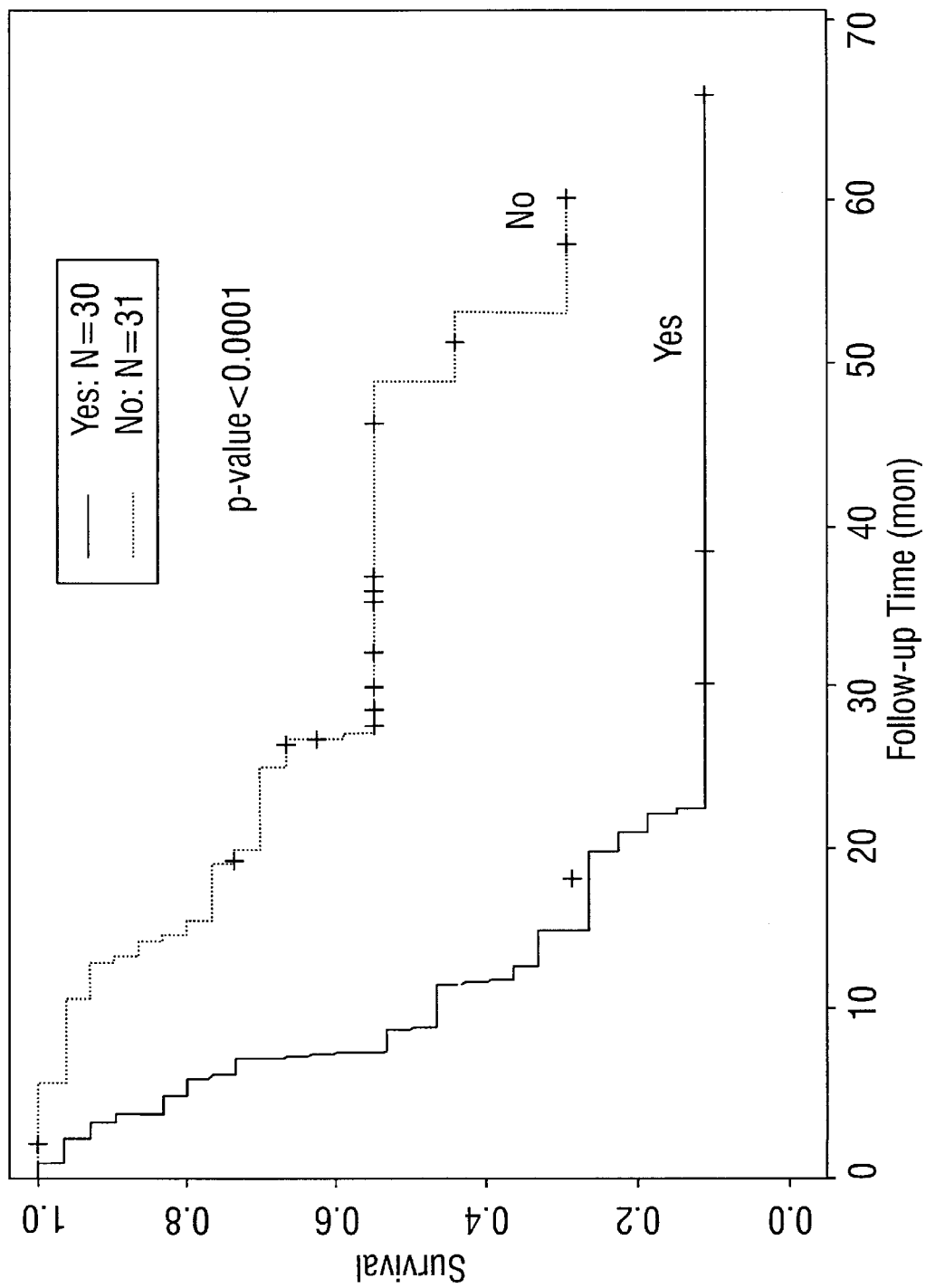
FIGS. 13A and 13B. Kaplan-Meier cures for the relationship between the presence and absence of nuclear GST-π in malignant gliomas and patient survival.
Figure 13B:
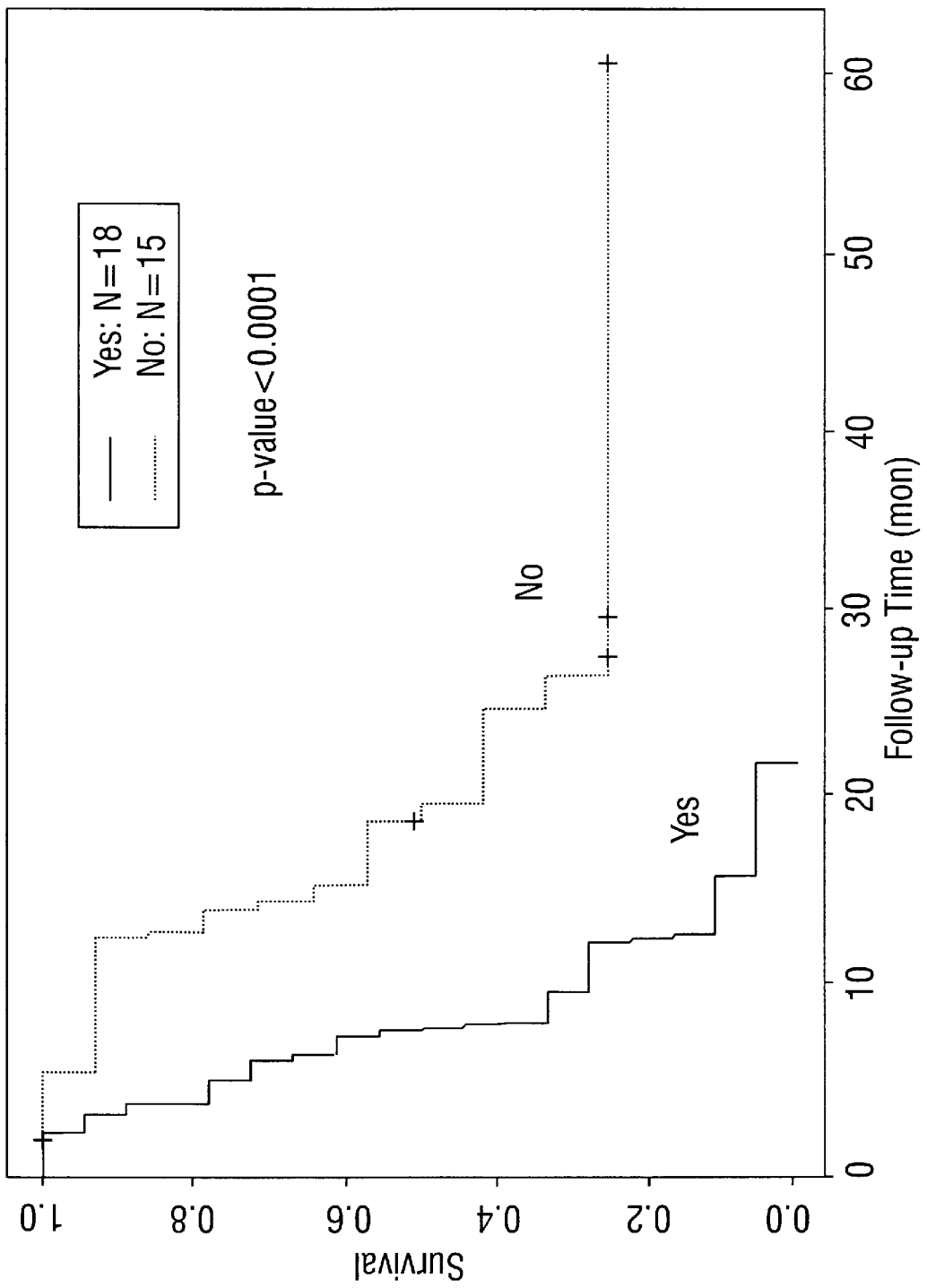

FIG. 13A and FIG. 13B show Kaplan-Meier survival plots for the presence or absence of nuclear GST-π in tumors of all glioma patients (FIG. 13A) and of glioblastoma patients (FIG. 13B). Patients with GST-π present in the nuclei of their tumor cells had a significantly lower survival rate than patients whose tumor cells were negative for nuclear GST-π. For glioblastoma patients, the difference in survival was particularly strong early in follow-up. At 15 months of follow-up, approximately 92% of patients with negative nuclear GST-π tumors were alive, compared with only 3% of patients whose tumors were positive for nuclear GST-π.

TABLE 8

Distribution of gliomas according to histological category and level of GST-π expression. GST-π expression was based on the intensity of the immunoreactivity of 70% of the cells

| | | Level of GST-π Expression | | |
|---|---|---|---|---|
| Histology | n | High | Moderate | Low |
| Glioblastoma multiforme | 33 (54%) | 15 (45%) | 9 (27%) | 9 (27%) |
| Anaplastic astrocytoma | 13 (21%) | 4 (31%) | 7 (54%) | 2 (15%) |
| Other gliomas | 15 (25%) | 4 (27%) | 4 (27%) | 7 (47%) |
| All Gliomas | 61 | 23 (38%) | 20 (33%) | 18 (29%) |

The p-value = 0.16 by exact chi-squared test.

TABLE 9

Relationship between level of GST-π expression in gliomas and patient age and histology

| | Age (Years) | | | | p-value |
|---|---|---|---|---|---|
| GST-π Expression | Minimum | Median | Maximum | n | (Kruskal-Wallis) |
| All gliomas | | | | | |
| Low | 24 | 48 | 75 | 18 | 0.27 |
| Moderate | 15 | 46 | 69 | 20 | |
| High | 24 | 58 | 71 | 23 | |
| Glioblastoma multiforme | | | | | |
| Low | 30 | 50 | 75 | 9 | 0.16 |
| Moderate | 34 | 57 | 69 | 9 | |
| High | 49 | 60 | 71 | 15 | |
| Anaplastic Astrocytoma | | | | | |
| Low | 24 | 26 | 27 | 2 | 0.23 |
| Moderate | 15 | 42 | 66 | 7 | |
| High | 24 | 36 | 52 | 4 | |
| Other gliomas | | | | | |
| Low | 28 | 47 | 68 | 7 | 0.78 |
| Moderate | 38 | 40 | 40 | 4 | |
| High | 29 | 41 | 46 | 4 | |

TABLE 10

Distribution of gliomas according to nuclear GST-π expression

| Variable | n | Number (%) of Tumors with Nuclear GST-π | p-value |
|---|---|---|---|
| a) Level of GST-π Expression | | | |
| Low | 18 | 2 (11%) | 0.0003 |
| Moderate | 20 | 11 (55%) | (chi-squared) |
| High | 23 | 17 (74%) | |
| b) Histology | | | |
| Glioblastoma multiforme | 33 | 18 (55%) | 0.63 |
| Anaplastic astrocytoma | 13 | 6 (46%) | (exact chi-squared test) |
| Other gliomas | 15 | 6 (40%) | |
| c) Age (Years) | | | |
| 15–39 | 18 | 4 (22%) | 0.0024 |
| 40–49 | 12 | 6 (50%) | (Kruskal-Wallis) |
| 50–59 | 12 | 5 (42%) | |
| 60–75 | 19 | 15 (79%) | |

TABLE 11

Panel a - univariate, and Panel b - multivariate Cox proportional hazard regression analysis of the relationship between the level of tumor GST-π expression, the presence/absence of nuclear GST-π in glioma cells, histology and patient age

| Variable | RR | 95 % CI | p-value |
|---|---|---|---|
| a) Univariate Analyses | | | |
| i) GST-π level | | | |
| High vs Low | 3.2 | (1.38, 7.5) | 0.0069 |
| Moderate vs Low | 2.6 | (1.07, 6.3) | 0.035 |
| ii) Nuclear GST-π Present vs Absent | 1.98 | (1.43, 2.75) | 0.0010 |
| b) Multivariate Analyses | | | |
| i) GST-π level | | | |
| High vs Low | 2.6 | (1.1, 6.2) | 0.036 |
| Moderate vs Low | 2.4 | (1.0, 5.9) | 0.051 |
| ii) Nuclear GST-π Present vs Absent | 4.4 | (2.1, 9.2) | 0.0001 |

The multivariate models for the level of GST-π expression and for presence/absence of nuclear GST-π were adjusted for age (continuous) and histology. The models also accounted for 51% of variation in survival time. Abbreviations: RR, relative risk; CI, confidence interval.

Example 4

Antisense Inhibitors of GST Variants

1. Materials and Methods

Oligonucleotide synthesis. All anti-sense olideoxyribonucleotides (AS-ONs) and control ONs were designed as 15-mers and were purified by chromatography on NAP-10 Sephadex column. AS-ONs directed at the initiation region of hGSTP1*C, INIT-AS-ON, covered sequences +1 to +15 of the mRNA. Jumbled ON controls contained the same base composition as the AS-ONs but with a randomization of the bases to avoid G quadruplets. Mismatch ON had the same structure as the AS-ON with the exception of two nucleotide mismatches at the 6th and 7th nucleotides. Partial phosphorothioate ONs had thioate substitutions in the first three 3' and last three 5' nucleotides. Fully modified ONs contained substitutions of thioates for all phosphates in the phosphodiester bonds of the ON. Unmodified ONs contained phosphodiester bonds with no substitutions. The primary structures of the AS-ONs and control ONs are shown in Table 12. Transition-specific AS-ONs (TS-ONs) were designed to contain the A→G and C→T transitions at +313 and at +341, respectively, that differentiate hGSTP1*C from the two other GST-π genes, hGSTP1*A and hGSTP1*B (Ali-Osman et al., 1996). All TS-ONs were partial phosphorothioates.

TABLE 12

Structure of Oligodeoxyribonucleotides used in translational inhibition of hGSTP1*C mRNA.

| Oligodeoxynucleotide Designation | Sequence | |
|---|---|---|
| AS-ON targeted to translation initiation site of hGSTP1*C mRNA | | |
| i) Antisense-ON | 5'-GGTGTAGGGCGGCAT-3' | (SEQ ID NO:35) |
| ii) Controls | | |
| Sense-ON | 5'-ATGCCGCCCTACACC-3' | (SEQ ID NO:36) |
| Jumbled-ON | 5'-CACGCTCCATCGCCA-3' | (SEQ ID NO:37) |
| Partial mismatch-ON | 5'-GGTGTGAGGCGGCAT-3' | (SEQ ID NO:38) |
| AS-ONs:targeted to transition site of hGSTP1*C mRNA | | |
| 313-Antisense-ON | 5'-GGGAGATGTATTTGC-3' | (SEQ ID NO:39) |
| 313-Transition-AS-ON | 5'-GGGAGACGTATTTGC-3' | (SEQ ID NO:40) |
| 341-Antisense-ON | 5'-TTGCCCGCCTCATAG-3' | (SEQ ID NO:41) |
| 341-Transition-AS-ON | 5'-TTGCCCACCTCATAG-3' | (SEQ ID NO:42) |

Construction of GST-π expression vector. The GST-π expression vector, pT7β-Pi, used in these studies, was constructed from the plasmid pT7β, kindly made available by Dr. Austin Cooney, Baylor College of Medicine, Houston, Tex. pT7β is derived from pGEM2 (Genbank accession number X65301) by inserting 44 nucleotides from the upstream non-coding region of the human beta globin gene into a region between a 5' HinD III site and a 3' T7 RNA polymerase promoter. The pT7β-Pi was created by ligating hGSTP1*C cDNA into the multiple cloning site in pT7β, such that the insert is 5' of an NcoI and 3' of an XbaI site and upstream of the non-coding beta globin sequence.

In Vitro Transcription of pT7β-Pi. 100 μg of the pT7β-Pi vector was linearized by digestion with 80 units of XbaI for 1 hr, the linearized plasmid extracted with phenol/chloroform, ethanol-precipitated, washed in 70% ethanol, and redissolved in 400 μl of nuclease-free water. A 1 ml transcription reaction mixture was set up containing 400 μl linearized DNA, 100 mM dithiothreitol, 600 nM each of ATP, UTP, CTP and GTP, 1000 U/ml of RNAsin ribonuclease inhibitor, and 400 units/ml of bacteriophage T7 RNA polymerase. The mixture was incubated for 2 hrs at 38.5° C. and additional 400 units of T7 RNA polymerase was added. After a further 2 hrs, 78 units of RNAse-free DNAse were added to digest the DNA template. Following a 15 min incubation at 37° C., the RNA product was extracted with phenol/chloroform, precipitated twice with ethanol/ammonium acetate, redissolved in nuclease-free water and the integrity of the run-off transcripts was monitored by electrophoresis in a 1.3% denaturing agarose-formaldehyde gel and UV spectrometry. Radiolabeled mRNAs were obtained by a ten-fold scaledown of the same protocol and substituting cold CTP with 250 μCi of 5'[alpha$^{32}$P]CTP in the reaction.

In vitro Translation of GST-pi with $^{35}$S-labelled Methionine. Approximately, 360 ng of recombinant hGSTP1*C mRNA (or an equimolar amount of control luciferase mRNA) were heated at 67° C. and quenched on ice for 10 mins to remove RNA secondary structure. The reaction mixtures (25 μl total volume) contained 14.5 μg/ml GST P1*C mRNA or an equimolar amount of luciferase control mRNA, 16.5 μl reticulocyte lysate, 60 mM exogenous KCl, 20 μM amino acid mixture without methionine, 800 U/ml RNASin ribonuclease inhibitor, and 0.4 mCi/ml L-[$^{35}$S] Methionine. The reaction was allowed to proceed for 1 hr at 30° C. and the translated proteins were analyzed by discontinuous SDS-polyacrylamide gel electrophosesis with a 4% stacking and a 12% separating gel, using 15 μl of 6-fold diluted samples per lane. The gels were fixed, incubated for 30 mins in EN³HANCE solution (Dupont Corporation, Boston, Mass.), dried and autoradiographed on Kodak XOMAT-AR5 film.

RNase H Effects on AS ON Translational Block of GST-pi mRNA. In vitro translation reaction mixtures were set up as described earlier containing unmodified, partially-modified, and fully-modified phosphorothioate AS ONs. E. coli RNase H was added to each sample to achieve 10 U/ml final concentration. RNAs in ribonuclease inhibitor was omitted from the reactions. After 1 hr incubation, the samples were analyzed as described earlier.

Oligonucleotide backbone structure and efficacy of translational inhibition. These series of studies were performed to examine the extent to which the structural modifications of the AS ON backbone performed to increase nuclease resistance and increased stability, affected the efficacy of the AS-ONs in inhibiting the translation of the hGSTP1*C mRNA. For this, unmodified, partially modified, and fully-modified phosphorothioate AS ONs were added to the $^{35}$S-Met translation reaction mixtures to achieve concentrations of 0 to 12.5 μM. The mixtures were incubated for 1 hr and analyzed for translation product as described earlier.

Translational inhibition by AS ON targeted to transition nucleotides in hGSTP1*C. These studies were designed to examine the ability to specifically inhibit the hGSTP1*C variant with an AS ONs (TS-AS ON) containing the nucleotide transitions in this mRNA variant. In vitro translation systems containing $^{35}$S-L-methionine were set up as described earlier, and the various AS ONs were added to achieve concentrations of 0 to 12.5 μM. After a 1 hr incubation (37° C.), the reaction products were analyzed, as described earlier. Controls for specificity of the TS-AS ON consisted of a sense ON with the basic structure but of a different base composition than the TS-AS ON, a jumbled ON with the same base composition but with the nucleotide sequence jumbled, and a partial mismatch ON with the same base composition but with the sixth and seventh nucleotides switched. All the TS-ONs were partially modified phosphorothioates.

2. Results

The results, summarized in Table 13, show that the antisense construct decreases GST-π mRNA by 42% and GST-π protein by 53%, when compared to untreated controls. The effect observed with jumbled and sense oligos were 5 and 4.7% (mRNA) and 7.2 and 8.9% (protein), respectively, indicating that the effects seen with the antisense construct were not as a result of non-specific interactions. Furthermore, clonogenic survival was significantly lower with the antisense treatment, whereas the controls were not.

Figure 14:
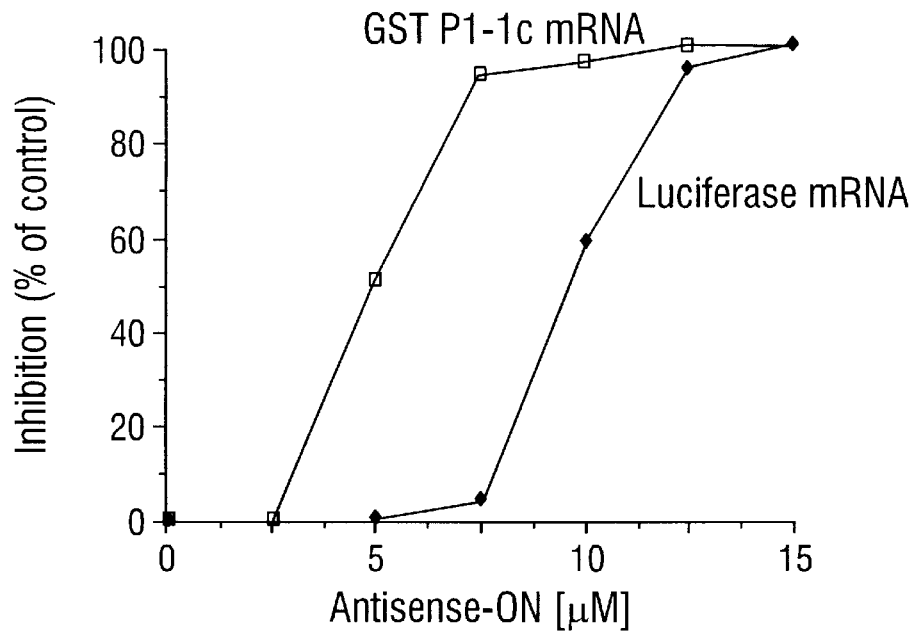
FIG. 14. Phosphorothioate antisense-ON and its effect on GSTP1*C expression. ON is designed around the initiation site of GSTP1*C mRNA expressed in glioblastoma multiforme cell line.
Figure 15:
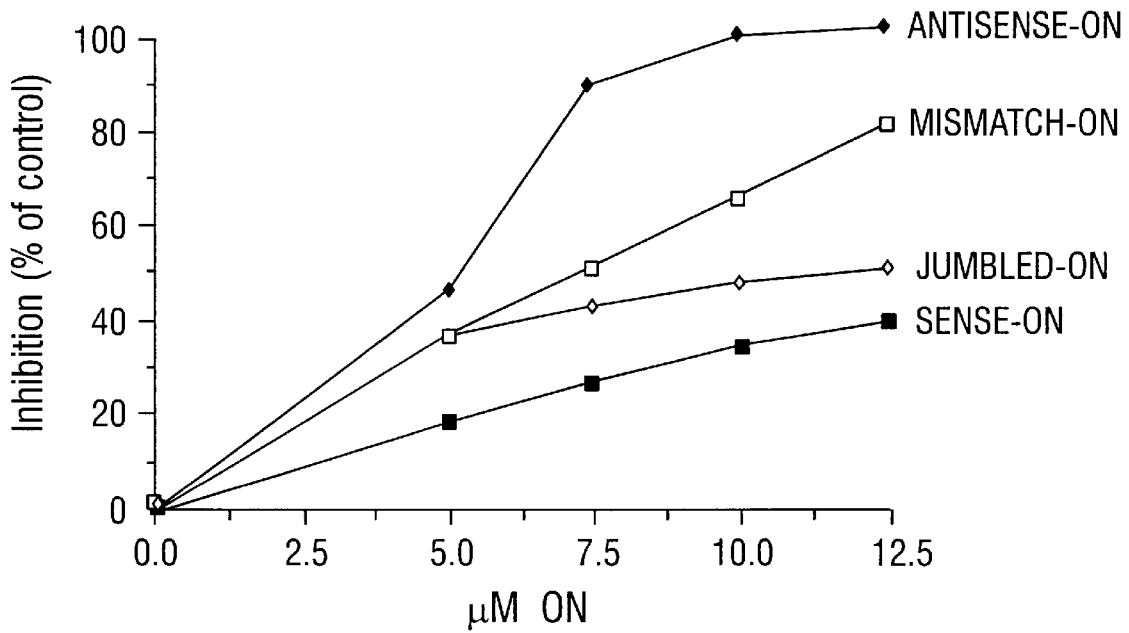
FIG. 15. Phosphorothioate antisense-ON and its effect on GSTP1*C expression. ON is designed around the initiation site of GSTP1*C mRNA expressed in glioblastoma multiforme cell line.

Studies were conducted to examine the effects of antisense ON's on translation of GSTP1*C. As shown in FIG. 14, 5 μM of ON designed around the mRNA translation initation site gave 50% inhibition of transcription, whereas this same concentration gave negligible inhibition of luciferase expression. At 10 μM ON, GSTP1*C expression was completely blocked, while luciferase was inhibited by about 60%. Using sense, partially mismatched and jumbled ON's, the specificity of the antisense ON directed to the GSTP1*C mRNA translational start site was examined. At 10 μM, the inhibition was 100% for antisense, 60% for mismatched, 45% for jumbled and 35% for sense (FIG. 15).

Figure 16:
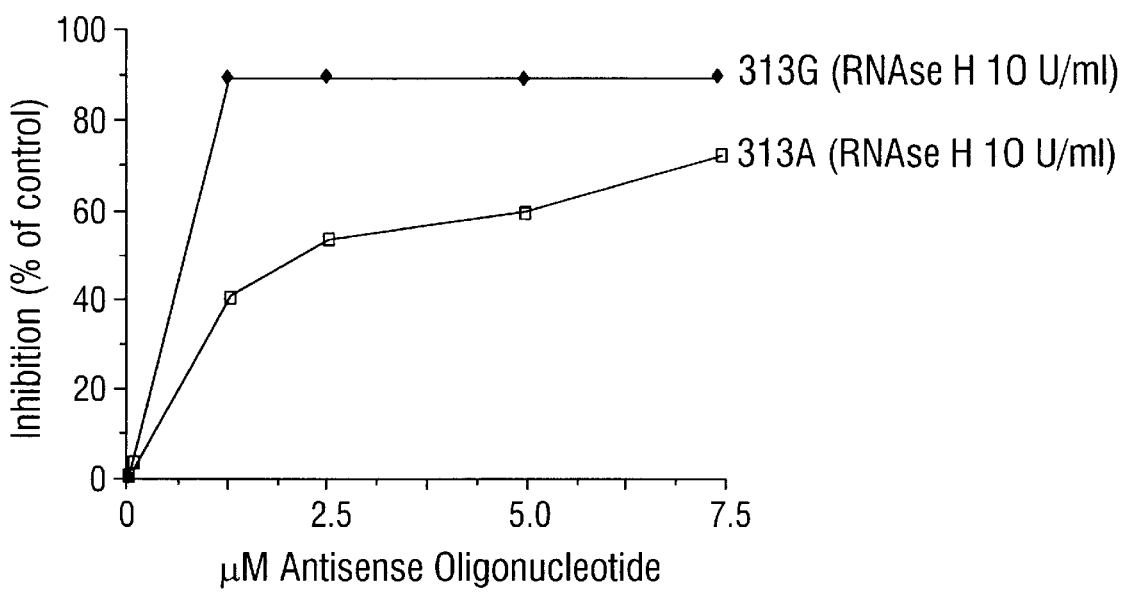
FIG. 16. Antisense-ON and its effect on GSTP1*C expression. ON is designed around the A to G transition and position 313. Treatment with 10 U/ml of RNAse H.
Figure 17:
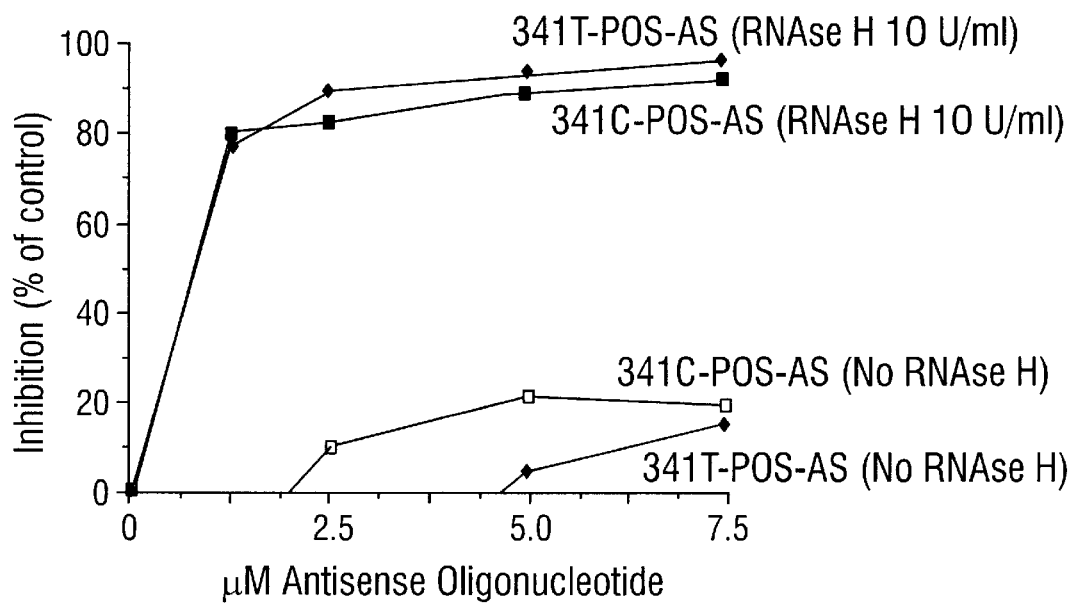
FIG. 17. Antisense-ON and its effect on GSTP1*C expression. ON is designed around the C to T transition and position 341. Treatment with 10 U/ml of RNAse H or no RNAse H.
Figure 18:
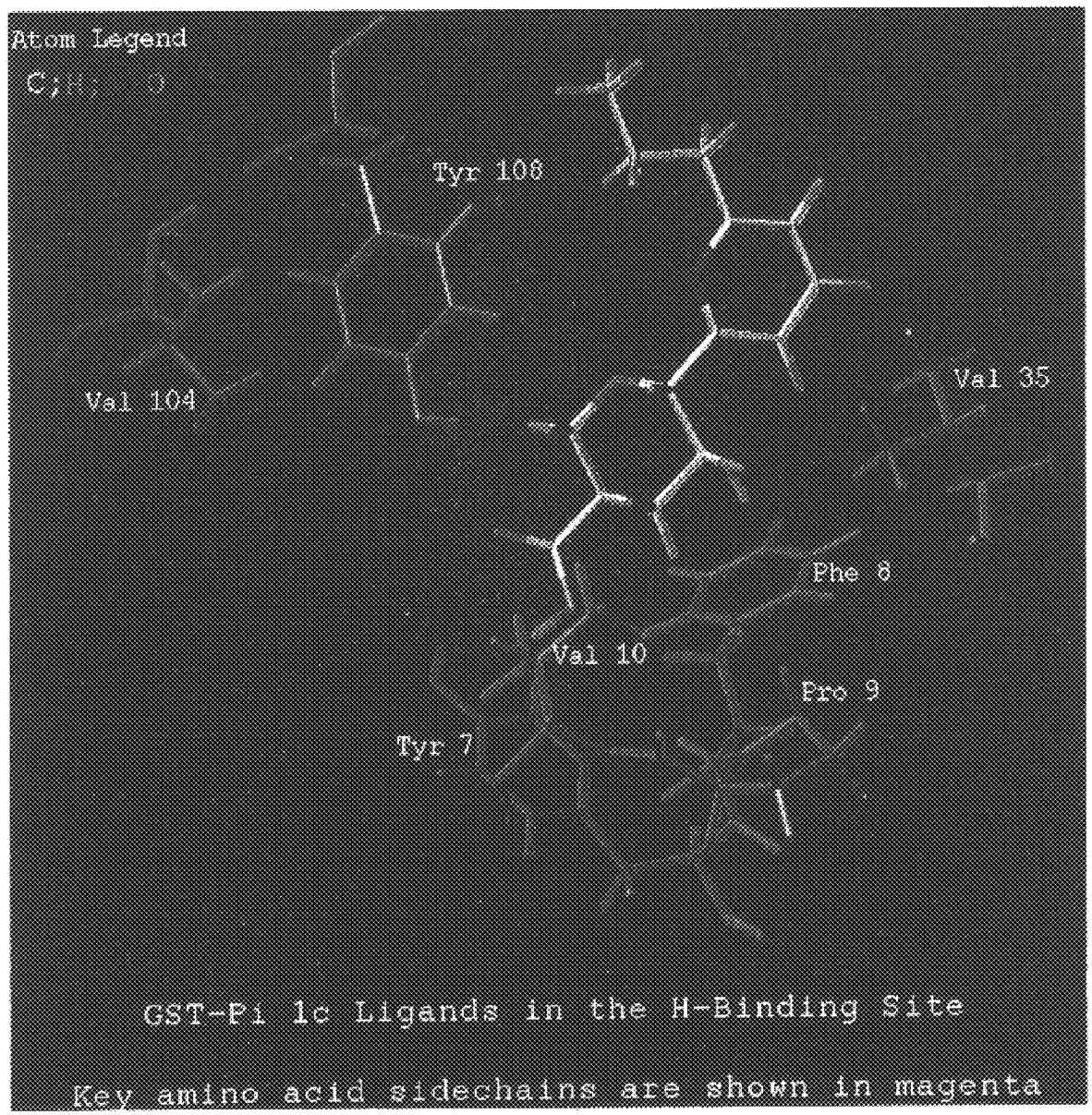
FIG. 18. Molecular modeling of putative GSTP1*C ligands in the H-binding site.
Figure 19:
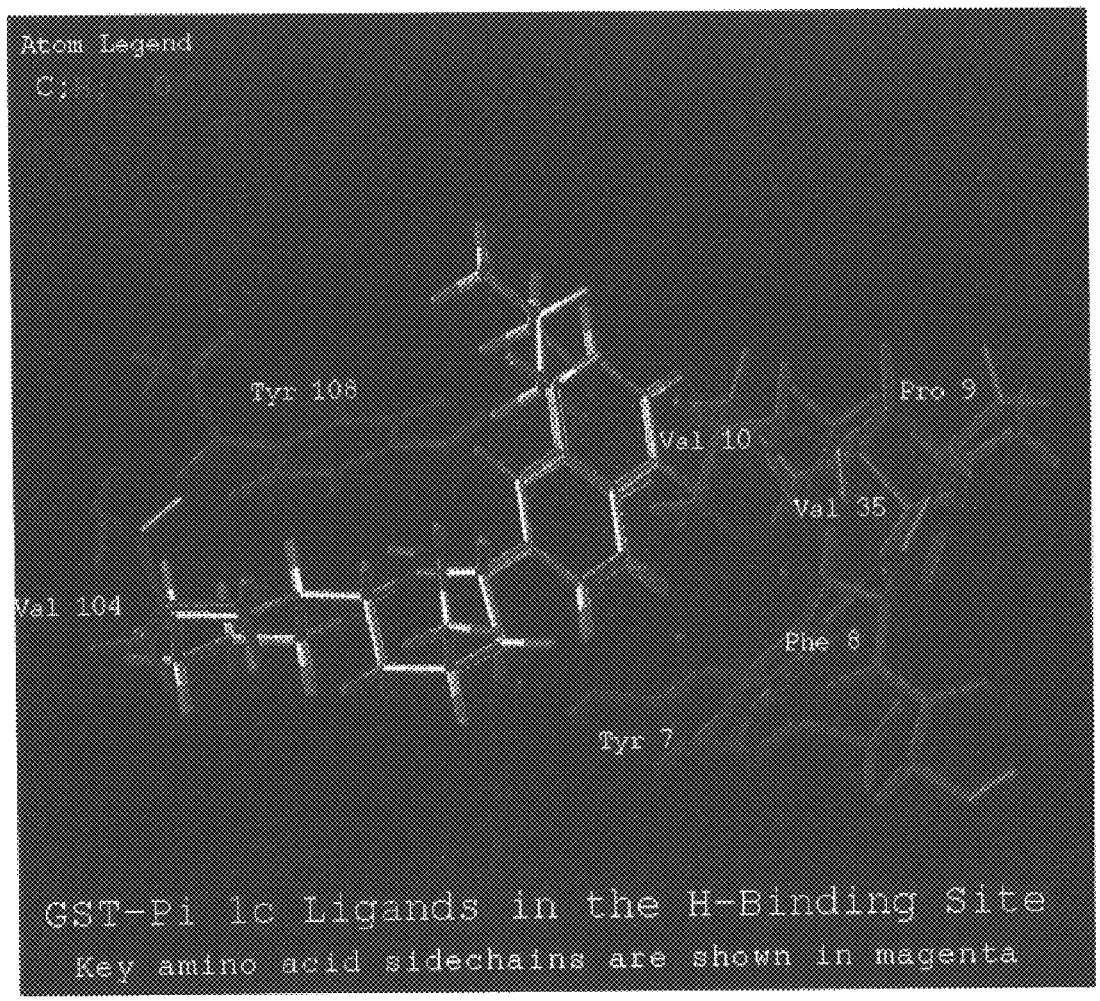
FIG. 19. Molecular modeling of putative GSTP1*C ligands in the H-binding site.

Studies were performed to determine the ability of ON's directed to the regions of GSTP1 at which variation occur. Using ON's that discriminate between the A/G at nucleotide 313, RNAse H was used to treat the ON's bound to GSTP1*C mRNA. As expected, the mismatch in the "A version" of the ON resulted in RNAse H degradation and impaired inhibition of GSTP1*C as compared with the "G version" (FIG. 16). A similar experiment was performed focusing on the C/T at position 341. Again, as expected, the inhibition of GSTP1*C expression by the "T version" was higher following RNAse H treatment, though only slightly so (FIG. 17). Interestingly, without RNAse H treatment, the "C version" had considerably better inhibition, especially at lower ON concentrations (FIG. 17).

TABLE 13

| Treatment | % GSTpi mRNA Inhibition[a] | % GSTpi Protein Decrease | Clonogenic Survival[c] | |
|---|---|---|---|---|
| | | | BCNU | Cisplatin |
| Control | 0 | 0 | 1.00 | 1.00 |
| Antisense-ON | 42 | 53 | 0.34 | 0.24 |
| Jumbled-ON | 5 | 7.2 | 0.93 | 0.91 |
| Sense-ON | 4.7 | 8.9 | 0.94 | 0.94 |

[a]Determined by northern analysis.
[b]Determined by western analysis.
[c]Determined by capillary clonogenic acid.

Example 5
Small Molecule Inhibitors of GST Variants
1. Materials and Methods Generation of GST-π inhibitors. Generation of inhibitors is accomplished by a rational drug development strategy involving force field docking and energy-minimization of chemical fragments and compounds into the active site of the variant GST-π proteins. The compounds and chemical fragments can be drawn from chemical fragment libraries, such as that available in the Leapfrog database. Additional chemical libraries will be generated as necessary. The active site and other structural components of the variant GST-π proteins will be derived from the published crystal structure of the GSTP1*A encoded protein. The protein encoded by GSTP1*B are obtained by substituting valine for isoleucine at amino acid 104; the protein encoded by GSTP1*C by substituting valine for isoleucine at amino acid 104, and valine for alanine at amino acid 113. Based on the resultant $\Delta\Delta H$ values obtained after energy minimization of chemical fragments/compounds, candidate inhibitors are selected and/or newly constructed from chemical fragments for synthesis and further analyses for their inhibitory or other action on the variant GST-π proteins. Selection criteria for inhibitors for synthesis and further analysis includes lipophilicity, chemical stability and availability or ease of synthesis.

Synthesis of GST-π Inhibitors. If the identified and/or newly constructed potential inhibitors are not commercially available, then they will be synthesized using standard organic synthetic methodology, including heterocyclic ring construction and functionalization, and electrophilic and nucleophilic substitution reactions. Reaction mixtures will be separated by thin layer, flash silica gel column and high performance liquid chromatography (TLC, CC and HPLC). The compounds will be purified using standard techniques modified as necessary. Characterization of synthetic products will be done by melting point determination, Fourier transform infrared (FT-1R), ultraviolet (UV) and high resolution nuclear magnetic resonance (NMR) spectroscopy and mass spectrometry. Compounds for biological testing will be purified by preparative HPLC. The purity of compounds will be determined by elemental analysis and HPLC.

Source of variant GST-π proteins. To examine the ability of the inhibitors selected from the rational design described above to inhibit the variant GST-π proteins, we will utilize recombinant GST-π proteins expressed in *E. coli* transfected with expression vectors containing the corresponding cDNAs. These vectors have been described elsewhere in this application. The GST-π proteins will be purified by GSH-affinity chromatography on S-hexyl glutathione linked to epoxy-activated sepharose 6B. and then used for enzyme kinetic analysis.

Analysis of inhibitors for GST inhibitory activity. These studies will be performed using standard enzyme kinetic methodologies. The purified variant GST-π proteins will be mixed with increasing inhibitor concentrations and at different time points, residual GST activity will be determined in reaction mixtures (25° C.) in 100 mM potassium phosphate buffer, pH 8.3 containing 0–5 mM 1-chloro-2,4-dintrobenzene (CDNB) and 2.5 mM GSH. The change in absorbance will be monitored at 340 nm over two minutes and used to compute reaction rates. The rates of the spontaneous reactions of GSH with CDNB, determined with reaction mixtures in which the GST-π enzyme will be replaced with buffer, will be subtracted from the rates of the enzyme catalyzed reactions. The resulting reaction rates will be used to generate appropriate enzyme kinetic plots, using standard methodology. Inhibitory constants will be computed for the different inhibitors and used in selecting candidates for further analyses of activity in tumor cells and subsequently in vivo.

Synthesis of Isoxazoles. Using the techniques described above, potential GST-π inhibitors such as isoxazoles have been identified. In the synthetic strategy for obtaining isoxazole GST inhibitors, the ring system can be achieved by the usual approach of cyclization between hyroxylamine and three-carbon atom component such as 1,3diketone or an α,β-unsaturated ketone or by a 1,3-dipolar cycloaddition reaction involving nitrile oxides with alkenes or an alkyne (Glichrist, T. L. (1992) *Heterocyclic Chemistry*, 2nd Edn, John Wiley & Sons, New York, Chapter 8, pp.314–316).

2. Results

Based on predicted binding energies for seven essential amino acids in GST-π peptides, a group of related compounds, substituted isoxazoles, were tested for their binding energies with GSTP1a, as shown in Table 14.

TABLE 14

The binding energies of substituted isoxazoles with GSTP1a

General Structure (Substituted Isoxazoles)

| Compound | $R_1$ | X | $R_2$ | $R_3$ | $R_4$ | Binding Energy (kcal/mol) |
|---|---|---|---|---|---|---|
| 1 | H | N | H | H | H | −38 |
| 2 | $NH_2$ | N | H | H | H | −44 |
| 3 | $NH_2$ | N | H | $CH_3$ | H | −45 |
| 4 | $CH_3$ | CH | H | $C_2H_5$ | H | −38 |
| 5 | OH | CH | H | $NHC_2H_5$ | $CH_3$ | −53 |
| 6 | OH | CH | H | $NHCH_2NH_2$ | $CH_3$ | −56 |
| 7 | $NH_2$ | N | H | $CH_3$ | Phenyl | −74 |
| 9 | $NH_2$ | N | H | $CH_3$ | 2-Pyridyl | −84 |

TABLE 15

The binding energies of fused aromatic compounds with GSTP1a

| Compound | Structure | Binding Energy (kcal/mol) |
|---|---|---|
| 9 | (structure with $CH_2ONH_2$) | −34 |
| 10 | (structure with $CH_2OCH_3$) | −41 |

TABLE 15-continued

The binding energies of fused aromatic compounds with GSTP1a

| Compound | Structure | Binding Energy (kcal/mol) |
|---|---|---|
| 11 | (7-methyl-8-quinolinyl with isoxazole) | −94 |
| 12 | (7-methyl-8-cinnolinyl with isoxazole) | −86 |
| 13 | (1,5-naphthyridine with pyrimidine) | −67 |
| 14 | (quinoxaline with pyrazine) | −56 |
| 15 | (8-amino-5-(2-pyridyl)quinoline) | −36 |

TABLE 16

The binding energy for sugar-linked aromatic compounds with GSTP1c

| Ligand Structure | Binding Energy at H-Site (kcal/mol) |
|---|---|
| (cyclohexyl-OCH2-(3-isobutylphenyl)) | −33 |
| (cyclohexyl-pyranose-phenyl with NH2) | −26 |
| (cyclohexyl-O-CH2-phenyl) | −30 |
| (H2N-cyclohexyl-O-CH2-naphthyl) | −29 |
| (pyranose with pyridyl, COOH, OH) | −21 |
| (cyclohexyl-pyranose-naphthyl with NH2) | −31 |

TABLE 17

The binding energy for four compounds with GSTP1c

| Ligand Structure | Binding Energy at H-Site (kcal/mol) |
|---|---|
| (2-thienyl-NH-OH) | −23 |

TABLE 17-continued

The binding energy for four compounds with GSTP1c

| Ligand Structure | Binding Energy at H-Site (kcal/mol) |
|---|---|
| thiophene-CH₂-OH | -33 |
| thiophene-CH(NH-CH₃)-OH | -21 |
| 2-aminopyridine | -22 |

Initial results of the force field docking of chemical fragments and compounds into the active site of the variant GST-π proteins have resulted in the identification of several classes of compounds that are potential GST-π variant protein inhibitors.

The first class of compounds are substituted isoxazoles, with the general structure shown in structures 1–3 (Table 14). The substituted groups in the different compounds are represented by $R_1$, $R_2$, $R_3$, and $R_4$. The substituted groups vary between the different compounds and result in significant changes in binding energies of the compounds in the active site pocket of the GST-π protein. For example, $R_1$ substitutions of either $NH_2$ or OH, cause changes in binding energies of almost 10 kcals/mol. Other important substitutions are the alkyl or aminoalkyl substitutions of $R_3$, and the alkyl, phenyl or 2-pyridyl substitutions of $R_4$, some of which result in changes in binding energies of greater than 10 kcals/mol.

Another group of potential variant GST-π protein inhibitors identified by the strategy described in this invention are the heterocyclic aromatic compounds, whose structures are shown in Table 15. The binding energies range from –34 to –94 kcal/mol, depending upon the type of compound or substitution.

The other groups of inhibitors are aromatic compounds and mono- and disaccharide derivatives of aromatic compounds with or without branched chains. The structures of representative candidates of these GST-π H-site ligands are given in Tables 16 and 17.

The structures shown in Tables 14–17 are only representatives of the structures that will be obtained with the rational design approach described in this application. The binding energies all show that the ligands will bind stably to the H-site of the GST-π protein. The inventors expect, however, to identify additional compounds using the same strategies and to perform additional structural modifications to these and to the other compounds to be obtained. These modifications will be performed to optimize the effectiveness, increase or decrease the solubility and or stability, and/or otherwise enhance the biological and or therapeutic efficacy of the compounds.

K. References

The following references, to the extent that they provide exemplary procedural or other details supplementary to those set forth herein, are specifically incorporated herein by reference:

EPO Application Publication No. 0036776
Ahmad, H., Wilson, D. E., Fritz, R. R., Singh, S. V., Medh, R. D., Singh, S. V., Nagle, G. T., Awasthi, Y. C., and Kurosky, A., *Arch. Biochem. Biophys.*, 278:398448, 1990.
Ali-Osman, F. and Akande O, *Biochimica*, 4:28, 1995.
Ali-Osman, F., Stein,.D and, Renwick, A., *Cancer Res.*, 50:6976–6980, 1990.
Ali-Osman, F., In: *Methods in Molecular Medicine*, Human Cell Culture Protocols, (ed.) G. E. Jones, Human Press Inc., pp. 63–80, 1996.
Baichwal & Sugden, In: *GENE TRANSFER* Kucherlapati, R., ed. New York: Plenum Press, pp. 117–148,1986.
Bangham et al., *J. Mol. Biol.* 13:238–52, 1965.
Benvenisty & Neshif, *Proc. Nat'l Acad. Sci. USA* 83:9551–9555, 1986.
Blaber, M., Zhang, X., and Matthews, B. W., *Science*, 260:1637–1646, 1993.
Board, P. G., Webb, G. C., and Coggan, M., *Ann. Hum. Genet.*, 53:205–213, 1989.
Bolivar et al., *Gene* 2:95, 1977.
Boussif et al., *Proc. Natl. Acad. Sci. USA*, 92:7297–7301, 1995.
Boylan, J. F. and Gudas, L. J., *J. Cell. Biol.*, 112:965–979, 1991.
Boyland, E. and Chasseaud, L. F., *Adv. Enzymol.*, 32:173–219, 1969.
Brutlag et al., *CABIOS*, 6:237–245, 1990.
Burger, P. C., Vogel, F. S., Green, S. B. et al., "Glioblastoma multiforme and anaplastic astrocytoma. Pathologic criterion and prognostic implications. *Cancer*, 56:1106–1111, 1985.
Chang et al. *Nature*, 375:615, 1978.
Chen. B., Johanson, L., Weist, J. S., Anderson, M. W. and You, M., *Proc. Natl. Acad. Sci. USA*, 91:1589–1593, 1994.
Chen & Okayama, *Mol. Cell Biol.*, 7:2745–2752, 1987.
Chomcznski, P and Saachi, N., *Anal. Biochem.*, 162:156–159, 1987.
Chrysogelos, S. A., *Nucleic Acid Res.*, 21:5736, 1993.
Coles, S. and Ketterer, B., CRC *Crit. Rev. Biochem. Mol. Biol.*, 25:47–70, 1980.
Commandeur, J. N., Stijntjes, J. N. M., Verineulen, N. P. E., *Pharmacol Rev.*, 47:271–330, 1995.
Cowell, I. G., Dioxin, K. H., S. E., Ketterer, B., and Taylor, J. B., *Biochem. J.*, 255:79–83, 1988.
Cox, D. R., Regression models and life tables, *J. Stat. Soc. Serv. Bul.*, 34:'87–110, 1972.
Dani, Ch., Blanchard, J. M., Piechaczyk, M., Sabouty, S. E., Marty, I. and Jeanteur, P., *Proc. Natl. Acad. Sci. USA*, 81:7046–7050, 1984.
Daniel, V., *Crit. Rev. Biochem. Mol. Biol.*, 28:173–207, 1993.
Dubensky et al,. *Proc. Nat'lAcad. Sci. USA*, 81:7529–7533, 1984.
Duester, G., Shean, M. L., McBride, M. S., and Stewart, M. J., *Mol. Cell Biol.*, 11: 1638–1646, 1991.
Durand, D., Saunders, M., Leroy, P., Leid, M. and Chambon, P., *Cell*, 71:73–85, 1992.
Fanjui A., Dawson, M. I., Hobbs, P. D., Jong, L. Cameron, J. F., Harlev, E., Graupner, G., Lu, X.-P and Pfahl, M., *Nature*, 372:107–110, 1994.
Favreau, L. V. and Pickett, C. B., *J. Biol. Chem.*, 266:4556–4561, 1990.
Fechheimer et al., *Proc. Nat'l Acad. Sci. USA*, 84:8463–8467, 1987.
Ferkol et al., *FASEB J.*, 7:1081–1091, 1993.
Fetrow & Bryant, *Biotechnology*, 11:479483, 1993.

Fraley et al., *Proc. Nat'l Acad. Sci. USA*, 76:3348–3352, 1979.

Gao et al., *Biochemical and Biophysical Research Communications*, 179(1):280–285, 1991.

Gefter et al., *Somatic Cell Genet.*, 3:231–236, 1977.

Ghosh & Bachhawat, In: Wu G. and C. Wu ed. Liver diseases, targeted diagnosis and therapy using specific receptors and ligands. New York: Marcel Dekker, pp. 87–104, 1991.

Gilbert, L., Elwood, Lori, J., Merino, M., Masood, S., Barnes, R., Steinberg, S. M., Lazarous, D. F., Pierce, L., d'Angelo, T., Moscow, J. A., Townsend, A. J., and Cowan, K. H., *J. Clin. Oncol.*, 11:49–58, 1993.

Glass, C. K., Di Renzo, J., Jurokawa, R., Han, Z., *DNA and Cell Biol.*, 10:623–638, 1991.

Glorioso et al., *Ann. Rev. Microbiol.*, 49:675–710, 1995.

Goeddel et al., *Nature*, 281:544, 1979.

Goeddel et al., *Nucleic Acids Res.*, 8:4057, 1980.

Gopal, Mol. Cell Biol., 5:1188–1190, 1985.

Graham & Van Der Eb, *Virology*, 52:456–467, 1973.

Gregoriadis, *Drug Carriers in Biology and Medicine*, G. Gregoriadis (ed.), 1979 pp. 287–341.

Gubler, U. and Hoffinann, B. J., *Gene* 25:263–267, 1983.

Habig, W. H., Pabst, M. J. and Jacoby, W. B., *J. Biol. Chem.*, 249:7130–7139, 1974.

Hara, A., Yamada, H., Sakai, N., Hirayama, H., Tanaka, T., and Mori, H., *Cancer* 66:2563–2568, 1990.

Harland & Weintraub, *J. Cell Biol.*, 101: 1094–1099, 1985.

Hayes, J. D. and Pulford, D. J., *Crit. Rev. Biochem. and Molec. Biol.*, 30:445–600, 1995.

Hess et al., *J. Adv. Enzyme Reg.*, 7:149, 1968.

Hitzeman et al., *J. Biol. Chem.*, 255:2073, 1980.

Hoffmann, B., Lehmann, J. M., Zhang, X. K., and Pfahl, M., *J. Mol. Endocrin.*, 4:1734–1743, 1990.

Holland et al., *Biochemistry*, 17:4900, 1978.

Hopp, U.S. Pat. No. 4,554,101.

Hupp, T. R., Meek, D. W., Midgely, C. A. and Lane, D. P., *Cell*, 71:875–886, 1992.

Itakura et al., *Science*, 198:1056, 1977.

Jameson & Wolf, *Comput. Appl. Biosci.*, 4(1):181–186, 1988.

Jones, *Genetics*, 85:12, 1977.

Jung, M., Dritschilo, A., Mark, G. and Kasid, U., *Biochem. and Biophy. Res. Comm.*, 190:462–469, 1993.

Kaneda et al., *Science*, 243:375–378, 1989.

Kano, T., Sakai, M., and Muramatsu, M., *Cancer Res.*, 47:5626–5630, 1987.

Kaplan, E. L., Meier, P., Non-parametric estimation from incomplete observations, *J. Amer. Stat. Assoc.*, 53:457–481, 1972.

Kato et al., *J. Biol. Chem.*, 266:3361–3364, 1991.

Ketterer, B. and Sies, H., *Glutathione Conjugation. Mechanisms and biological significance*, Academic Press, London, San Diego, New York, 1987.

Kingsman et al., *Gene*, 7:141., 1979.

Klein et al., *Nature*, 327:70–73, 1987.

Kohler & Milstein, *Nature*, 256:495–497, 1975.

Kohler & Milstein, *Eur. J. Immunol.*, 6:511–519, 1976.

Kyte & Doolittle, *J. Mol. Biol.*, 157(1):105–132, 1982.

Lammie, G. A. and Peters, G., *Cancer Cells*, 3:413–420, 1991.

Lozano, G. and Levine, A. J., *Molec. Carcin.*, 4:3–9, 1991.

Lehmann, J. M., Zhang, X.-K., and Pfahl, M., *Mol. Cell. Biol.*, 12:2976–2985, 1992.

Leroy, P., Nakshastri, H., Chambon, P., *Proc. Natl. Acad. Sci. USA*, 88:10138–10142, 1991.

Li, Y. and Jaiswal, A. K., *J. Biol. Chem.*, 267:15097–15104, 1992.

Lipman, S. M., Kessler, J. F., and Meyskens, F. L., *Cancer Treatment Reports*, 71:391–405, 1987.

Lowry, O., Rosebrough, N. J., Farr, A. L. and Randall, R. J., *J. Biol Chem.*, 193:265–275, 1951.

Mangelsdorf, D. J., Umesono, K., Kliewer, S. A., Borgmeyer, U., Ong, E. S., and Evans, R. M., *Cell*, 66:555–561, 1991.

Mannervik, B. and Danielson, U. G. H., *CRC Crit. Rev. Biochem.*, 23:283–337, 1988.

Mannervik, B., *Adv. Enzymol.*, 57:357–417, 1985.

Mannervik, B., Awasthi, Y. C., Board, P. G., Hayes, J. D., Illio, C. D., Ketterer, B., Listowsky, L., Morgenstern, R., Muramatsu, M., Pearson, W. R., Pickett, C. B., Sato, K., Wildersten, M., and Wolf, C. R., *Biochem. J.*, 282:305–307, 1992.

Maurer, H. R., Maschler, R., Dietrich, R., Goebel, B., *J. Immun. Meth.*, 18:353, 1977.

Morrow, C. S. and Cowan, K. H., *Cancer Cells*, 2:15–22, 1990.

Morrow, C. S., Cowan, K. H., and Goldsmith, M. E., *Gene*, 75:3–11, 1989.

Moscow, J. A., Townsend, A. J., Goldsmith, M. E., Whang-Peng J., Vickers P.J., Legault-Poisson S., Myers C. E. and Cowan K. H., *Proc. Natl. Acad. Sci*, 85:6518–6522, 1988.

Mosmann, *J. Immunol. Methods*, 65:55–63, 1983.

Muramatsu, M., Morimura, S., Suzuki, T., Imagawa, M., and Kitagawa, T., In: *Structure and function of Glutathione transferases*, ed. Tew, Pickett, Mantle, Mannervik, and Hayes, CRC Press, Boca Raton, Ann Arbor, London, Tokyo, 297–308, 1993.

Myers, EPO 0273085.

Nabel et al., *Science* 249:1285–1288.

Nasrin, N., Ercolani, L., Denaro, M., Kong, X. F., Kang, I. and Alexander, M., *Proc. Natl. Acad. Sci. USA*, 87:5273, 1990.

Nelson, J. S., Tsukada, Y., Shoenfeld, D. et al., Necrosis as a prognostic criterion in malignant supratentorial astrocytic gliomas, *Cancer*, 52:550–554, 1983.

Nicolas & Rubenstein, In: *Vectors: A survey of molecular cloning vectors and their uses*, Rodriguez & Denhardt (eds.), Stoneham: Butterworth, pp. 494–513, 1988.

Nicolau & Sene, *Biochem. Biophys. Acta*, 721:185–190, 1982.

Nicolau et al., *Methods Enzymol.*, 149:157–176, 1987.

Perales et al., *Proc. Nat'l Acad. Sci. USA*, 91:4086–4090, 1994.

Pickett, C. B. and Lu, A. Y. H., *Annu. Rev. Biochem.*, 58:743–764, 1989.

Pikarsky, E., Sharir, H., Ben-Shushan, E. and Bergman, Y., *Mol. Cell Biol.*, 14:1026–1038, 1994.

Potter et al., *Proc. Nat'l Acad. Sci. USA*, 81:7161–7165, 1984.

Reindeer, P., Direr, H. W., R., Hubbell, R., Lo, M., G. and Parker, M., *J. Mol. Biol.*, 227:214–226, 1992.

Reinemer, P., Dirr, H. W., and Huber, R., In: *Structure and function of Glutathione transferases*, Tew, K. D, Pickett, C. B., Mantle, T. J., Mannervik, B. and Hayes, J. D., (ed), CRC Press, Boca Raton, Ann Arbor, London, Tokyo, pp. 15–27, 1993.

Ridgeway, In: Rodriguez R L, Denhardt D T, ed. Vectors: A survey of molecular cloning vectors and their uses. Stoneham: Butterworth, pp. 467–492, 1988.

Rippe et al., *Mol. Cell Biol.*, 10:689–695, 1990.

Rubinstein et al., *J. Natl. Cancer Inst.*, 82:1113–1120, 1990.

Saint-Ruf, C., Malfoy, B., Scholl, S., Zafrani, B., and Dutrillaux, B., *Oncogene*, 6:403406, 1991.

Sakai, M, Okuda, A., and Muramatsu, M., *J. Biol. Chem.*, 262:3858–3863, 1987.

Sambrook, J., E. F. Fritsch, and T. Maniatis, *Molecular Cloning—A laboratory manual*, Cold Spring Harbor Laboratory Press, 1989.
Sanger, F., Nicklen, S., and Coulson, A. R., Proc. Natl. Acad. Sci. USA, 74:5463–5467, 1977.
Sato, K., *Advances in Cancer Res.*, 52:205–255, 1989.
Schule, R., Rangarajan, P., Yang, N., Kliewer, S., Ransone, L. J., Bolado, J., Verma,. I. M., and Evans, R. M., *Proc. Nat'l Acad. Sci. USA* 88:6092–6096, 1991.
Segel, I. H., *Biochemical Calculations*, John Wiley and Sons, New York, Chicheter, Brisbane, Singapore, pp. 208–318, 1976.
She, H, Ranganathan S, Kuzmich, S. and Tew K. D., *Biochem. Pharmacol.*, 50:1233–1238, 1995.
Simons, P. C. and Van der Jagt, D. L., In: *Methods in Enzymology*, Jacoby, W. (ed), 77:235–237, 1981.
Smith, W. C., Leroy, P., Nakshastri, H., Leroy, P., Rees, J., Chambon, P., *EMBO J.*, 88:2223–2230, 1991.
Stinchcomb et al., *Nature*, 282:3., 1979.
Stumpo, D. J., Stewart, T. N., Gilman, M. Z. and Blackshear, P. J., *J. Biol. Chem.*, 263:1611–1614, 1988.
Takimoto, Y. and Kuramoto, A., *Jpn J. Can. Res.*, 84:1268–1272, 1993.
Takumi, T. and Lodish, H. F. *Biotechniques*, 17:443–444, 1994.
Taub, R., Roy, A., Dieter, R. and Koontz, J., *J. Biol. Chem.*, 262:10893–10897, 1987.
Temin, In: Kucherlapati R, ed. Gene transfer. New York: Plenum Press, pp. 149–188, 1986.
Tew, K., Cancer Res., 54:4313–4320, 1994.
de The, H., Vivanco-Ruiz, M., Tiollais, P., Stunnenberg, H. and Dejean, A., *Nature*, 343:177–180, 1990.
Tidefelt, U., Elmhom-Rosenberg, A., Paul, C., Hao, X-Y., Mannervik, B., and Erikson, L. C., *Cancer Res.*, 52:3281–3285, 1992.
*Tissue Culture*, 1973
Tschemper et al., *Gene*, 10: 157, 1980.
Tsuchida, S. and Sato, K., *Crit. Rev. Biochem. Mol. Biol.*, 27:337–384, 1992.
Tur-Kaspa et al., "Use of electroporation to introduce biologically active foreign genes into primary rat hepatocytes," *Mol. Cell Biol.*, 6:716–718, 1986.
Vasios, G. W., Mader, J. D., Gold, M., Leid, M., Lutz, Y., Gaub, M.-P., Chambon P., Gudas, L., *Proc. Natl. Acad. Sci. USA*, 86:9091–9103.
Wagner et al., *Science*, 260:1510–1513, 1993.
Waxman, D. J., *Cancer Res.*, 50:6449–6454, 1990.
Weinberger et al., *Science*, 228:740–742, 1985.
Wolf et al., *Comput. Appl. Biosci.*, 4(1):187–191, 1988.
Wong et al., *Gene*, 10:87–94, 1980.
Wu & Wu, *Biochemistry*, 27:887–892, 1988.
Wu & Wu, *J. Biol. Chem*, 262:4429–4432, 1987.
Wu & Wu, *Adv. Drug Delivery Rev.*, 12:159–167, 1993.
Xia, C. L., Cowell, I. G., Dixon, J. H., Pemble, S. E., Ketterer, B., and Taylor, J. B., *Biochem. Biophys. Res. Comm.*, 176–233–240, 1991.
Xia, C., Taylor, B., Spensor, S. R., and Ketterer, B., *Biochem. J.*, 292:845–850, 1993.
Xia, C. L., Hu, J., Ketterer, B., and Taylor, J. B., *Biochem. J.*, 313:155–161, 1996.
Yang et al., *Proc. Nat'l Acad. Sci. USA*, 87:9568–9572, 1990.
Yang-Yen, H.-F., Zang, X.-K., Graupner, G., Tsukerman, J., Sakamoto, B., Karin, M., Pfahl, M., *New Biol.*, 3:1206–1219,
Zelenin et al., *FEBS Lett.*, 280:94–96, 1991.
Zimniak, P, Pikula, S. Bandorowicz-Pikula, J. Singhal, S. S., Srivastava, S. K., Awasthi, S., Awasthi, Y. C., *Eur. J. Biochem*, 224:893–899, 1994.

---

What is claimed is:

1. A method for the identification of a candidate GST-π antisense or ribozyme molecule that inhibits GST-π activity comprising the steps of:

a) contacting a cell expressing a GST-π protein with the antisense or ribozyme molecule; and b) comparing the growth of said cell with the growth of said cell in the absence of the antisense or ribozyme molecule;

wherein a decrease in growth in the presence of said antisense or ribozyme molecule is indicative of the molecule being an inhibitor of GST-π activity.

2. The method of claim 1, wherein said GST-π protein expressed is GSTP*B.

3. The method of claim 1, wherein said GST-π protein expressed is GSTP*C.

4. The method of claim 1, wherein said GST-π protein being expressed is not GSTP*A.

5. The method of claim 1, wherein said GST-π antisense or ribozyme molecule is an antisense molecule to an hGSTP1*B or hGSTP1*C nucleic acid.

6. The method of claim 1, wherein said GST-π antisense or ribozyme molecule is a ribozyme that cleaves an hGSTP1*B or hGSTP1*C nucleic acid under intracellular conditions.

7. A method for the identification of a candidate inhibitor substance that inhibits GST-π expression comprising the steps of:

a) contacting a cell expressing a GST-π protein with a candidate inhibitor substance; and b) comparing the expression of GST-π of said cell with the expression of GST-π of said cell in the absence of said candidate inhibitor substance;

wherein a decrease in the expression of GST-π in the presence of said candidate inhibitor substance is indicative of the substance being an inhibitor of GST-π expression.

8. The method of claim 7, wherein said candidate inhibitor substance is an antisense molecule to an hGSTP1*B or hGSTP1*C nucleic acid.

9. The method of claim 7, wherein said candidate inhibitor substance is a ribozyme that cleaves an hGSTP1*B or hGSTP1*C nucleic acid under intracellular conditions.

10. The method of claim 7, wherein said candidate inhibitor substance is a small molecule inhibitor.

11. The method of claim 10, wherein the small molecule inhibitor is a substituted isoxazole, heterocyclic aromatic compound; or a sugar-linked aromatic compound.

* * * * *

UNITED STATES PATENT AND TRADEMARK OFFICE
CERTIFICATE OF CORRECTION

PATENT NO. : 5,968,737
DATED : October 19, 1999
INVENTOR(S) : Ali-Osman et al.

It is certified that error appears in the above-identified patent and that said Letters Patent is hereby corrected as shown below:

Column 2,
Line 44, please delete "+313 or +341" and insert therefor -- +326 or +354 --.
Line 61, please delete "SEQ ID NO: 4" and insert therefor -- SEQ ID NO:7 --.

Column 3,
Line 2, please delete "+313 or +341" and insert therefor --+326 or +354 --, and please delete "SEQ ID NO:4" and insert therefor -- SEQ ID NO:7 --.
Lines 10 and 11, please delete "SEQ ID NO: 3" and insert therefor -- SEQ ID NO:8 --.
Line 22, please delete "SEQ ID NO:1" and insert therefor -- SEQ ID NO:6 --.
Line 23, please delete "SEQ ID NO:3" and insert therefor -- SEQ ID NO:8 --.
Line 26, please delete "SEQ ID NO:1" and insert therefor -- SEQ ID NO:6 --.
Line 27, please delete "SEQ ID NO:3" and insert therefor -- SEQ ID NO:8 --.
Line 31, please delete "SEQ ID NO:2" and insert therefor -- SEQ ID NO:5 --.
Line 53, please delete "SEQ ID NO:4" and insert therefor -- SEQ ID NO:7 --.
Line 36, please delete "SEQ ID NO:1" and insert therefor -- SEQ ID NO:6 --.
Line 38, please delete "SEQ ID NO:3" and insert therefor -- SEQ ID NO:8 --.
Line 41, please delete "SEQ ID NO:1" and insert therefor -- SEQ ID NO:6 --.
Line 42, please delete "SEQ ID NO:2" and insert therefor -- SEQ ID NO:5 --.
Line 44, please delete "SEQ ID NO:3" and insert therefor -- SEQ ID NO:8 --.
Line 45, please delete "SEQ ID NO:4" and insert therefor -- SEQ ID No:7 --.
Lines 52 and 53 please delete "SEQ ID NO:3" and insert therefor -- SEQ ID NO:8 --.

Column 6,
Line 16, after "313" please insert -- (326 of SEQ ID NO:7) --.
Line 19, after "341" please insert -- (341 of SEQ ID NO:7) --.
Line 45, please delete "cDNAs" and insert therefor -- SEQ ID NO:3 (+326 and +341 of SEQ ID NO7) --.

Column 7,
Line 6, please delete "+313" and insert therefor -- +326 --, and insert -- (SEQ ID NO: 7) -- after *"hGSTPI * B"*.
Line 64, after "+341" please insert -- (+326 and +341 of SEQ ID NO:7) --.

UNITED STATES PATENT AND TRADEMARK OFFICE
CERTIFICATE OF CORRECTION

PATENT NO. : 5,968,737
DATED : October 19, 1999
INVENTOR(S) : Ali-Osman et al.

It is certified that error appears in the above-identified patent and that said Letters Patent is hereby corrected as shown below:

Column 55,
Line 9, after "+313" please insert -- (+326 of SEQ ID NO:7) --.
Line 14, after "+341" please insert -- (+326 and +341 of SEQ ID NO:7) --.

Column 64,
Line 40, after "+341" please insert -- (+326 and +341 of SEQ ID NO:7) --.

Signed and Sealed this

Twenty-fifth Day of September, 2001

Attest:

NICHOLAS P. GODICI
Attesting Officer     Acting Director of the United States Patent and Trademark Office

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
      (A) LENGTH: 3117 base pairs
      (B) TYPE: nucleic acid
      (C) STRANDEDNESS: single
      (D) TOPOLOGY: linear (xi) SEQUENCE DESCRIPTION: SEQ ID NO:1:

```
GCGGCCGCCG GGGCTGGGGC CGGCGGGAGT CCGCGGGACC CTCCAGAAGA GCGGCCGGCG      60

CCGTGACTCA GCACTGGGGC GGAGCGGGGC GGGACCACCC TTATAAGGCT CGGAGGCCGC     120

GAGGCCTTCG CTGGAGTTTC GCCGCCGCAG TCTTCGCCAC CAGTGAGTAC GCGCGGCCCG     180

CGTCCCCGGG GATGGGGCTC AGAGCTCCCA GCATGGGGCC AACCCGCAGC ATCAGGCCCG     240

GGCTCCCGGC AGGGCTCCTC GCCCACCTCG AGACCCGGGA CGGGGGCCTA GGGGACCCAG     300

GACGTCCCCA GTGCCGTTAG CGGCTTTCAG GGGGCCCGGA GCGCCTCGGG GAGGGATGGG     360

ACCCCGGGGG CGGGGAGGGG GGGGCAGGCT GCGCTCACCG CGCCTTGGCA TCCTCCCCCG     420

GGCTCCAGCA AACTTTTCTT TGTTCGCTGC AGTGCCGCCC TACACCGTGG TCTATTTCCC     480

AGTTCGAGGT AGGAGCATGT GTCTGGCAGG GAAGGGAGGC AGGGGCTGGG GCTGCAGCCC     540
```

```
ACAGCCCCTC GCCCACCCGG AGAGATCCGA ACCCCCTTAT CCCTCCGTCG TGTGGCTTTT      600

ACCCCGGGCC TCCTTCCTGT TCCCCGCCTC TCCCGCCATG CCTGCTCCCC GCCCCAGTGT      660

TGTGTGAAAT CTTCGGAGGA ACCTGTTTCC CTGTTCCCTC CCTGCACTCC TGACCCCTCC      720

CCGGGTTGCT GCGAGGCGGA GTCGGCCCGG TCCCCACATC TCGTACTTCT CCCTCCCCGC      780

AGGCCGCTGC GCGGCCCTGC GCATGCTGCT GGCAGATCAG GGCCAGAGCT GGAAGGAGGA      840

GGTGGTGACC GTGGAGACGT GGCAGGAGGG CTCACTCAAA GCCTCCTGCG TAAGTGACCA      900

TGCCCGGGCA AGGGGAGGGG GTGCTGGGCC TTAGGGGGCT GTGACTAGGA TCGGGGACG       960

CCCAAGCTCA GTGCCCCTCC CTGAGCCATG CCTCCCCCAA CAGCTATACG GGCAGCTCCC     1020

CAAGTTCCAG GACGGAGACC TCACCCTGTA CCAGTCCAAT ACCATCCTGC GTCACCTGGG     1080

CCGCACCCTT GGTGAGTCTT GAACCTCCAA GTCCAGGGCA GGCATGGGCA AGCCTCTGCC     1140

CCCGGAGCCC TTTTGTTTAA ATCAGCTGCC CCGCAGCCCT CTGGAGTGGA GGAAACTGAG     1200

ACCCACTGAG GTTACGTAGT TTGCCCAAGG TCAAGCCTGG GTGCCTGCAA TCCTTGCCCT     1260

GTGCCAGGCT GCCTCCCAGG TGTCAGGTGA GCTCTGAGCA CCTGCTGTGT GGCAGTCTCT     1320

CATCCTTCCA CGCACATCCT CTTCCCCTCC TCCCAGGCTG GGGCTCACAG ACAGCCCCCT     1380

GGTTGGCCCA TCCCCAGTGA CTGTGTGTTG ATCAGGCGCC CAGTCACGCG GCCTGCTCCC     1440

CTCCACCCAA CCCCAGGGCT CTATGGGAAG GACCAGCAGG AGGCAGCCCT GGTGGACATG     1500

GTGAATGACG GCGTGGAGGA CCTCCGCTGC AAATACGTCT CCCTCATCTA CACCAACTAT     1560

GTGAGCATCT GCACCAGGGT TGGGCACTGG GGGCTGAACA AAGAAAGGGG CTTCTTGTGC     1620

CCTCACCCCC CTTACCCCTC AGGTGGCTTG GGCTGACCCC TTCTTGGGTC AGGGTGCAGG     1680

GGCTGGGTCA GCTCTGGGCC AGGGGCCCAG GGGCCTGGGA CAAGACACAA CCTGCACCCT     1740

TATTGCCTGG GACATCAACC AGCCAAGTAA CGGGTCATGG GGGCGAGTGC AAGGACAGAG     1800

ACCTCCAGCA ACTGGTGGTT TCTGATCTCC TGGGGTGGCG AGGGCTTCCT GGAGTAGCCA     1860

GAGGTGGAGG AGGATTTGTC GCCAGTTTCT GGATGGAGGT GCTGGCACTT TTAGCTGAGG     1920

AAAATATGCA GACACAGAGC ACATTTGGGG ACCTGGGACC AGTTCAGCAG AGGCAGCGTG     1980

TGTGCGCGTG CGTGTGCGTG TGTGTGCGTG TGTGTGTGTA CGCTTGCATT TGTGTCGGGT     2040

GGGTAAGGAG ATAGAGATGG GCGGGCAGTA GGCCCAGGTC CCGAAGGCCT TGAACCCACT     2100

AGTTTGGAGT CTCCTAAGGG CAATGGGGGC CATTGAGAAG TCTGAACAGG GCTGTGTCTG     2160

AATGTGAGGT CTAGAAGGAT CCTCCAGAGA AGCCAGCTCT AAAGCTTTTG CAATCATCTG     2220

GTGAGAGAAC CCAGCAAGGA TGGACAGGCA GAATGGAATA GAGATGAGTT GGCAGCTGAA     2280

GTGGACAGGA TTTGGTACTA GCCTGGTTGT GGGGAGCAAG CAGAGGAGAA TCTGGGACTC     2340

TGGTGTCTGG CCTGGGGCAG ACGGGGGTGT CTCAGGGGCT GGGAGGGATG AGAGTAGGAT     2400

GATACATGGT GGTGTCTGGC AGGAGGTGGG CAAGGATGAC TATGTGAAGG CACTGCCCGG     2460

GCAACTGAAG CCTTTTGAGA CCCTGCTGTC CCAGAACCAG GGAGGCAAGA CCTTCATTGT     2520

GGGAGACCAG GTGAGCATCT GGCCCCATGC TGTTCCTTCC TCGCCACCCT CTGCTTCCAG     2580

ATGGACACAG GTGTGAGCCA TTTGTTTAGC AAAGCAGAGC AGACCTAGGG GATGGGCTTA     2640

GGCCCTCTGC CCCCAATTCC TCCAGCCTGC TCCCGCTGGC TGAGTCCCTG GTCCCCCTGC     2700

CCTGCAGATC TCCTTCGCTG ACTACAACCT GCTGGACTTG CTGCTGATCC ATGAGGTCCT     2760

AGCCCCTGGC TGCCTGGATG CGTTCCCCCT GCTCTCAGCA TATGTGGGGC GCCTCAGCGC     2820

CCGGCCCAAG CTCAAGGCCT TCCTGGCCTC CCCTGAGTAC GTGAACCTCC CCATCAATGG     2880

CAACGGGAAA CAGTGAGGGT TGGGGGGACT CTGAGCGGGA GGCAGAGTTT GCCTTCCTTT     2940
```

```
CTCCAGGACC AATAAAATTT CTAAGAGAGC TACTATGAGC ACTGTGTTTC CTGGGACGGG    3000

GCTTAGGGGT TCTCAGCCTC GAGGTCGGTG GGAGGGCAGA GCAGAGGACT AGAAAACAGC    3060

TCCTCCAGCA CAGTCAGTGG CTTCCTGGAG CCCTCAGCCT GGCTGTGTTT ACTGAAC      3117
```

(2) INFORMATION FOR SEQ ID NO:2:

(i) SEQUENCE CHARACTERISTICS:
        (A) LENGTH: 210 amino acids
        (B) TYPE: amino acid
        (C) STRANDEDNESS:
        (D) TOPOLOGY: linear (xi) SEQUENCE DESCRIPTION: SEQ ID NO:2:

```
Met Pro Pro Tyr Thr Val Val Tyr Phe Pro Val Arg Gly Arg Cys Ala
1               5                   10                  15

Ala Leu Arg Met Leu Leu Ala Asp Gln Gly Gln Ser Trp Lys Glu Glu
            20                  25                  30

Val Val Thr Val Glu Thr Trp Gln Glu Gly Ser Leu Lys Ala Ser Cys
        35                  40                  45

Leu Tyr Gly Gln Leu Pro Lys Phe Gln Asp Gly Asp Leu Thr Leu Tyr
    50                  55                  60

Gln Ser Asp Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Ile Ser Leu Ile Tyr Thr Asn Tyr
            100                 105                 110

Glu Ala Gly Lys Asp Asp Tyr Val Lys Ala Leu Pro Gly Gln Leu Lys
        115                 120                 125

Pro Phe Glu Thr Leu Leu Ser Gln Asn Gln Gly Gly Lys Thr Phe Ile
    130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
            180                 185                 190

Phe Leu Ala Ser Pro Glu Tyr Val Asn Leu Pro Ile Asn Gly Asn Gly
        195                 200                 205

Lys Gln
    210
```

(2) INFORMATION FOR SEQ ID NO:3:

(i) SEQUENCE CHARACTERISTICS:
        (A) LENGTH: 712 base pairs
        (B) TYPE: nucleic acid
        (C) STRANDEDNESS: single
        (D) TOPOLOGY: linear (xi) SEQUENCE DESCRIPTION: SEQ ID NO:3:

```
TTCGCCACCA TGCCGCCCTA CACCGTGGTC TATTTCCCAG TTCGAGGCCG CTGCGCGGCC    60

CTGCGCATGC TGCTGGCAGA TCAGGGCCAG AGCTGGAAGG AGGAGGTGGT GACCGTGGAG    120

ACGTGGCAGG AGGGCTCACT CAAAGCCTCC TGCCTATACG GGCAGCTCCC CAAGTTCCAG    180

GACGGAGACC TCACCCTGTA CCAGTCCAAT ACCATCCTGC GTCACCTGGG CCGCACCCTT    240

GGGCTCTATG GAAGGACCA GCAGGAGGCA GCCCTGGTGG ACATGGTGAA TGACGGCGTG    300
```

```
GAGGACCTCC GCTGCAAATA CATCTCCCTC ATCTACACCA ACTATGAGGC GGGCAAGGAT      360

GACTATGTGA AGGCACTGCC CGGGCAACTG AAGCCTTTTG AGACCCTGCT GTCCCAGAAC      420

CAGGGAGGCA AGACCTTCAT TGTGGGAGAC CAGATCTCCT TCGCTGACTA CAACCTGCTG      480

GACTTGCTGC TGATCCATGA GGTCCTAGCC CCTGGCTGCC TGGATGCGTT CCCCCTGCTC      540

TCAGCATATG TGGGGCGCCT CAGCGCCCGG CCCAAGCTCA AGGCCTTCCT GGCCTCCCCT      600

GAGTACGTGA ACCTCCCCAT CAATGGCAAC GGGAAACAGT GAGGGTTGGG GGGACTCTGA      660

GCGGGAGGCA GAGTTTGCCT TCCTTTCTCC AGGACCAATA AAATTTCTAA GA              712
```

(2) INFORMATION FOR SEQ ID NO:4:

(i) SEQUENCE CHARACTERISTICS:
  (A) LENGTH: 210 amino acids
  (B) TYPE: amino acid
  (C) STRANDEDNESS:
  (D) TOPOLOGY: linear (xi) SEQUENCE DESCRIPTION: SEQ ID NO:4:

```
Met Pro Pro Tyr Thr Val Val Tyr Phe Pro Val Arg Gly Arg Cys Ala
1               5                   10                  15

Ala Leu Arg Met Leu Leu Ala Asp Gln Gly Gln Ser Trp Lys Glu Glu
            20                  25                  30

Val Val Thr Val Glu Thr Trp Gln Glu Gly Ser Leu Lys Ala Ser Cys
        35                  40                  45

Leu Tyr Gly Gln Leu Pro Lys Phe Gln Asp Gly Asp Leu Thr Leu Tyr
    50                  55                  60

Gln Ser Asn Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Ile Ser Leu Ile Tyr Thr Asn Tyr
            100                 105                 110

Glu Ala Gly Lys Asp Asp Tyr Val Lys Ala Leu Pro Gly Gln Leu Lys
        115                 120                 125

Pro Phe Glu Thr Leu Leu Ser Gln Asn Gln Gly Gly Lys Thr Phe Ile
    130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
            180                 185                 190

Phe Leu Ala Ser Pro Glu Tyr Val Asn Leu Pro Ile Asn Gly Asn Gly
        195                 200                 205

Lys Gln
    210
```

(2) INFORMATION FOR SEQ ID NO:5:

(i) SEQUENCE CHARACTERISTICS:
  (A) LENGTH: 718 base pairs
  (B) TYPE: nucleic acid
  (C) STRANDEDNESS: single
  (D) TOPOLOGY: linear (xi) SEQUENCE DESCRIPTION: SEQ ID NO:5:

```
GTCTTCGCCA CCATGCCGCC CTACACCGTG GTCTATTTCC CAGTTCGAGG CCGCTGCGCG       60
```

```
GCCCTGCGCA TGCTGCTGGC AGATCAGGGC CAGAGCTGGA AGGAGGAGGT GGTGACCGTG      120

GAGACGTGGC AGGAGGGCTC ACTCAAAGCC TCCTGCCTAT ACGGGCAGCT CCCCAAGTTC      180

CAGGACGGAG ACCTCACCCT GTACCAGTCC AATACCATCC TGCGTCACCT GGGCCGCACC      240

CTTGGGCTCT ATGGGAAGGA CCAGCAGGAG GCAGCCCTGG TGGACATGGT GAATGACGGC      300

GTGGAGGACC TCCGCTGCAA ATACGTCTCC CTCATCTACA CCAACTATGA GGCGGGCAAG      360

GATGACTATG TGAAGGCACT GCCCGGGCAA CTGAAGCCTT TTGAGACCCT GCTGTCCCAG      420

AACCAGGGAG GCAAGACCTT CATTGTGGGA GACCAGATCT CCTTCGCTGA CTACAACCTG      480

CTGGACTTGC TGCTGATCCA TGAGGTCCTA GCCCCTGGCT GCCTGGATGC GTTCCCCCTG      540

CTCTCAGCAT ATGTGGGGCG CCTCAGTGCC CGGCCCAAGC TCAAGGCCTT CCTGGCCTCC      600

CCTGAGTACG TGAACCTCCC CATCAATGGC AACGGGAAAC AGTGAGGGTT GGGGGGACTC      660

TGAGCGGGAG GCAGAGTTTG CCTTCCTTTC TCCAGGACCA ATAAAATTTC TAAGAAGC       718
```

(2) INFORMATION FOR SEQ ID NO:6:

(i) SEQUENCE CHARACTERISTICS:
      (A) LENGTH: 210 amino acids
      (B) TYPE: amino acid
      (C) STRANDEDNESS:
      (D) TOPOLOGY: linear (xi) SEQUENCE DESCRIPTION: SEQ ID NO:6:

```
Met Pro Pro Tyr Thr Val Val Tyr Phe Pro Val Arg Gly Arg Cys Ala
1               5                   10                  15

Ala Leu Arg Met Leu Leu Ala Asp Gln Gly Gln Ser Trp Lys Glu Glu
            20                  25                  30

Val Val Thr Val Glu Thr Trp Gln Glu Gly Ser Leu Lys Ala Ser Cys
        35                  40                  45

Leu Tyr Gly Gln Leu Pro Lys Phe Gln Asp Gly Asp Leu Thr Leu Tyr
    50                  55                  60

Gln Ser Asn Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Val Ser Leu Ile Tyr Thr Asn Tyr
            100                 105                 110

Glu Ala Gly Lys Asp Asp Tyr Val Lys Ala Leu Pro Gly Gln Leu Lys
        115                 120                 125

Pro Phe Glu Thr Leu Leu Ser Gln Asn Gln Gly Gly Lys Thr Phe Ile
    130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
            180                 185                 190

Phe Leu Ala Ser Pro Glu Tyr Val Asn Leu Pro Ile Asn Gly Asn Gly
        195                 200                 205

Lys Gln
    210
```

(2) INFORMATION FOR SEQ ID NO:7:

(i) SEQUENCE CHARACTERISTICS:

(A) LENGTH: 722 base pairs
        (B) TYPE: nucleic acid
        (C) STRANDEDNESS: single
        (D) TOPOLOGY: linear (xi) SEQUENCE DESCRIPTION: SEQ ID NO:7:

```
AGTCTTCGCC ACCATGCCGC CCTACACCGT GGTCTATTTC CCAGTTCGAG GCCGCTGCGC     60

GGCCCTGCGC ATGCTGCTGG CAGATCAGGG CCAGAGCTGG AAGGAGGAGG TGGTGACCGT    120

GGAGACGTGG CAGGAGGGCT CACTCAAAGC CTCCTGCCTA TACGGGCAGC TCCCCAAGTT    180

CCAGGACGGA GACCTCACCC TGTACCAGTC CAATACCATC CTGCGTCACC TGGGCCGCAC    240

CCTTGGGCTC TATGGGAAGG ACCAGCAGGA GGCAGCCCTG GTGGACATGG TGAATGACGG    300

CGTGGAGGAC CTCCGCTGCA AATACGTCTC CCTCATCTAC ACCAACTATG AGGTGGGCAA    360

GGATGACTAT GTGAAGGCAC TGCCCGGGCA ACTGAAGCCT TTTGAGACCC TGCTGTCCCA    420

GAACCAGGGA GGCAAGACCT TCATTGTGGG AGACCAGATC TCCTTCGCTG ACTACAACCT    480

GCTGGACTTG CTGCTGATCC ATGAGGTCCT AGCCCCTGGC TGCCTGGATG CGTTCCCCCT    540

GCTCTCAGCA TATGTGGGGC GCCTCAGCGC CCGGCCCAAG CTCAAGGCCT TCCTGGCCTC    600

CCCTGAGTAC GTGAACCTCC CCATCAATGG CAACGGGAAA CAGTGAGGGT TGGGGGGACT    660

CTGAGCGGGA GGCAGAGTTT GCCTTCCTTT CTCCAGGACC AATAAAATTT CTAAGAAGCT    720

AC                                                                  722
```

(2) INFORMATION FOR SEQ ID NO:8:

(i) SEQUENCE CHARACTERISTICS:
        (A) LENGTH: 210 amino acids
        (B) TYPE: amino acid
        (C) STRANDEDNESS:
        (D) TOPOLOGY: linear (xi) SEQUENCE DESCRIPTION: SEQ ID NO:8:

```
Met Pro Pro Tyr Thr Val Val Tyr Phe Pro Val Arg Gly Arg Cys Ala
1               5                  10                  15

Ala Leu Arg Met Leu Leu Ala Asp Gln Gly Gln Ser Trp Lys Glu Glu
            20                  25                  30

Val Val Thr Val Glu Thr Trp Gln Glu Gly Ser Leu Lys Ala Ser Cys
        35                  40                  45

Leu Tyr Gly Gln Leu Pro Lys Phe Gln Asp Gly Asp Leu Thr Leu Tyr
    50                  55                  60

Gln Ser Asn Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

Val Glu Asp Leu Arg Cys Lys Tyr Val Ser Leu Ile Tyr Thr Asn Tyr
            100                 105                 110

Glu Val Gly Lys Asp Asp Tyr Val Lys Ala Leu Pro Gly Gln Leu Lys
        115                 120                 125

Pro Phe Glu Thr Leu Leu Ser Gln Asn Gln Gly Gly Lys Thr Phe Ile
    130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
            180                 185                 190
```

```
Phe Leu Ala Ser Pro Glu Tyr Val Asn Leu Pro Ile Asn Gly Asn Gly
    195                 200                 205

Lys Gln
    210
```

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:9:

CGCAAGCTTC GCCACCATGC CGCCCTACAC CG                    32

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:10:

GGAGGCTTTG AGTGAGCCCT C                              21

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:11:

AGATCAGGGC CAGAGCTGGA AG                           22

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:12:

CTGGTTCTGG GACAGGGTCT C                              21

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

CTCTGGTCTA GAGGAAGCGA                              20

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:14:

TCTTCCTCTT CTAGTTTGTG AGG                                           23

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:15:

TCTTTGTTCG GACCATGCCG CCC                                           23

(2) INFORMATION FOR SEQ ID NO:16:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:16:

CAGAGTCCCC CCAACCCTCA CTGTTT                                        26

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:17:

CAGCCCTGGT GGACATGGTG AATGAC                                        26

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:18:

CTGGTTCTGG GACAGCAGCT C                                             21

(2) INFORMATION FOR SEQ ID NO:19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:19:

TGGCAGCTGA AGTGGACAGG ATT                                           23

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:20:

```
GATCAGCAGC AAGTCCAGCA G                                                    21

(2) INFORMATION FOR SEQ ID NO:21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:21:

GTGAGCATCT GCACCAGG                                                        18

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:22:

GGCTGGTTGA TGATGTCCCA GG                                                   22

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:23:

ACGTGGCAGG AGGGCTCACT C                                                    21

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:24:

TACTCAGGGG AGGCCAGCAA                                                      20

(2) INFORMATION FOR SEQ ID NO:25:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:25:

CATCTCCCTC ATCTACACCA ACTATGAGGC G                                         31

(2) INFORMATION FOR SEQ ID NO:26:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 3
        (D) OTHER INFORMATION: /mod_base= OTHER
```

/note= "N = C, T, A or G"

(xi) SEQUENCE DESCRIPTION: SEQ ID NO:26:

CGNTCTCCCT CATCTACACC AACTATGAGG CG                                32

(2) INFORMATION FOR SEQ ID NO:27:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ix) FEATURE:
      (A) NAME/KEY: modified_base
      (B) LOCATION: 3..32
      (D) OTHER INFORMATION: /mod_base= OTHER
          /note= "N = C, T, A or G"

(xi) SEQUENCE DESCRIPTION: SEQ ID NO:27:

CGNTCTCCCT CATCTACACC AACTATGAGG TNG                               33

(2) INFORMATION FOR SEQ ID NO:28:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (xi) SEQUENCE DESCRIPTION: SEQ ID NO:28:

CCAGGCTGGG GCTCACAGAC AGC                                          23

(2) INFORMATION FOR SEQ ID NO:29:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (xi) SEQUENCE DESCRIPTION: SEQ ID NO:29:

GGTCAGCCCA AGCCACCTGA GG                                           22

(2) INFORMATION FOR SEQ ID NO:30:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (xi) SEQUENCE DESCRIPTION: SEQ ID NO:30:

TGGCAGCTGA AGTGGACAGG ATT                                          23

(2) INFORMATION FOR SEQ ID NO:31:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (xi) SEQUENCE DESCRIPTION: SEQ ID NO:31:

ATGGCTCACA CCTGTGTCCA TCT                                          23

(2) INFORMATION FOR SEQ ID NO:32:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:32:

GTGACAAAGC                                                              10

(2) INFORMATION FOR SEQ ID NO:33:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (xi) SEQUENCE DESCRIPTION: SEQ ID NO:33:

GTGACTCAGC                                                              10

(2) INFORMATION FOR SEQ ID NO:34:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ix) FEATURE:
            (A) NAME/KEY: modified_base
            (B) LOCATION: 4..12
            (D) OTHER INFORMATION: /mod_base= OTHER
                /note= "N = A, T, C, or G"

(xi) SEQUENCE DESCRIPTION: SEQ ID NO:34:

CCANNNNNNN NNTGG                                                        15

(2) INFORMATION FOR SEQ ID NO:35:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:35:

GGTGTAGGGC GGCAT                                                        15

(2) INFORMATION FOR SEQ ID NO:36:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:36:

ATGCCGCCCT ACACC                                                        15

(2) INFORMATION FOR SEQ ID NO:37:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:37:

CACGCTCCAT CGCCA                                                        15

```
(2) INFORMATION FOR SEQ ID NO:38:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:38:

GGTGTGAGGC GGCAT                                                          15

(2) INFORMATION FOR SEQ ID NO:39:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:39:

GGGAGATGTA TTTGC                                                          15

(2) INFORMATION FOR SEQ ID NO:40:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:40:

GGGAGACGTA TTTGC                                                          15

(2) INFORMATION FOR SEQ ID NO:41:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:41:

TTGCCCGCCT CATAG                                                          15

(2) INFORMATION FOR SEQ ID NO:42:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:42:

TTGCCCACCT CATAG                                                          15
```